United States Patent
Strings-Ufombah et al.

(10) Patent No.: US 11,142,765 B2
(45) Date of Patent: *Oct. 12, 2021

(54) REAGENTS FOR TREATMENT OF OCULOPHARYNGEAL MUSCULAR DYSTROPHY (OPMD) AND USE THEREOF

(71) Applicant: Benitec Biopharma Limited, North Sydney (AU)

(72) Inventors: Vanessa Strings-Ufombah, Hayward, CA (US); David Suhy, Hayward, CA (US)

(73) Assignee: Benitec IP Holdings, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/469,992

(22) PCT Filed: Dec. 14, 2017

(86) PCT No.: PCT/AU2017/051385
§ 371 (c)(1),
(2) Date: Jun. 14, 2019

(87) PCT Pub. No.: WO2018/107228
PCT Pub. Date: Jun. 21, 2018

(65) Prior Publication Data
US 2019/0330629 A1 Oct. 31, 2019

Related U.S. Application Data

(60) Provisional application No. 62/434,312, filed on Dec. 14, 2016.

(51) Int. Cl.
*C12N 15/113* (2010.01)

(52) U.S. Cl.
CPC ...... *C12N 15/113* (2013.01); *C12N 2310/141* (2013.01); *C12N 2310/531* (2013.01); *C12N 2330/51* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 2010/0199379 A1* | 8/2010 | Sanz Molinero | C12N 15/8261 800/278 |
| 2011/0207224 A1* | 8/2011 | Zamore | A61P 7/06 435/455 |
| 2012/0171686 A1* | 7/2012 | Delfour | C12N 15/113 435/6.12 |
| 2020/0138849 A1* | 5/2020 | Suhy | C07K 14/47 |

FOREIGN PATENT DOCUMENTS

| | | | |
|---|---|---|---|
| WO | WO-2010105372 A1 * | 9/2010 | ......... C12N 15/1131 |
| WO | 2017/177277 A1 | 10/2017 | |
| WO | 2018/107228 A1 | 6/2018 | |

OTHER PUBLICATIONS

"International Search Report and Written Opinion of the International Searching Authority," Int'l Application No. PCT/AU2017/051385, dated Mar. 1, 2018, 13 pages.
Klein, P. et al., "Gene Therapy Strategy for Oculopharyngeal Muscular Dystrophy (OPMD)," Journal of Neuromuscular Diseases, 2014, vol. 1, Suppl. 1, pp. S222, p. S220/#515.
Dickson et al., "Gene Therapy Rescues Disease Phenotype in the Oculopharyngeal Muscular Dystrophy Mouse Model," Molecular Therapy, 2016, vol. 24, Supp. 1, p. S199.
Anvar et al., "A Decline in PABPN1 Induces Progressive Muscle Weakness in Oculopharyngeal Muscle Dystrophy and in Muscle Again," Aging, 2013, vol. 5, No. 6, pp. 412-426.
Apponi et al., "Loss of Nuclear Poly(A)-binding Protein 1 Causes Defects in Myogenesis and mRNA Biogenesis," Human Molecular Genetics, 2010, vol. 19, No. 6, pp. 1058-1065.
Fellmann et al., "An Optimized MicroRNA Backbone for Effective Single-Copy RNAi," Cell Reports, 2013, vol. 5, pp. 1704-1713.
Boden et al., "Enhanced Gene Silencing of HIV-1 Specific siRNA Using MicroRNA Designed Hairpins," Nucleic Acids Research, 2004, vol. 32, No. 3, pp. 1154-1158.
Fowler et al., "Improved Knockdown from Artificial MicroNRAs in an Enhanced miR-155 Backbone: A Designer's Guide to Potent Multi-Target RNAi,", Nucleic Acids Research, 2016, vol. 44, No. 5:e48.
Malerba et al., "PABPN1 Gene therapy for Oculopharyngeal Muscular Dystophy," Nature Communications, Mar. 31, 2017, pp. 1-14.
Malerba et al., "Established PABPN1 Intranuclear Inclusions in OPMD Muscle can be Efficiently Reversed by AAV-Mediated Knockdown and Replacement of Mutant Expanded PABPN1," Human Molecular Genetics, 2019, vol. 28, No. 19, pp. 3301-3308.
Riaz et al., "PABPN1-Dependent mRNA Processing Induces Muscle Wasting," PLOS Genetics 12(5): May 6, 2016, 19 pages.

* cited by examiner

*Primary Examiner* — Brian Whiteman
(74) *Attorney, Agent, or Firm* — Goodwin Procter LLP

(57) ABSTRACT

The present disclosure relates to RNA interference (RNAi) reagents, such as short hairpin microRNA (shmiR) and short hairpin RNA (shRNA), for treatment of oculopharyngeal muscular dystrophy (OPMD), compositions comprising same, and use thereof to treat individuals suffering from OPMD or which are predisposed thereto. The present disclosure also relates to the use of the RNAi reagents in combination with PABPN1 replacement reagents, such as constructs which encode functional PABPN1 protein, for treatment of OPMD, compositions comprising same, and use thereof to treat individuals suffering from OPMD or which are predisposed thereto.

27 Claims, 14 Drawing Sheets
Specification includes a Sequence Listing.

shmiR2 (SEQ ID NO: 43)

SEQUENCE LISTING

```
<160> NUMBER OF SEQ ID NOS: 86

<210> SEQ ID NO 1
<211> LENGTH: 28
<212> TYPE: RNA
<213> ORGANISM: Homo sapiens

<400> SEQUENCE: 1
gagaagcaga ugaauaugag uccaccuc                                      28

<210> SEQ ID NO 2
<211> LENGTH: 28
<212> TYPE: RNA
<213> ORGANISM: Homo sapiens

<400> SEQUENCE: 2
gaacgaggua gagaagcaga ugaauaug                                      28

<210> SEQ ID NO 3
<211> LENGTH: 28
<212> TYPE: RNA
<213> ORGANISM: Homo sapiens

<400> SEQUENCE: 3
gaagcugaga agcuaaagga gcuacaga                                      28

<210> SEQ ID NO 4
```

```
<211> LENGTH: 28
<212> TYPE: RNA
<213> ORGANISM: Homo sapiens

<400> SEQUENCE: 4
gggcuagagc gacaucaugg uauucccc                                              28

<210> SEQ ID NO 5
<211> LENGTH: 28
<212> TYPE: RNA
<213> ORGANISM: Homo sapiens

<400> SEQUENCE: 5
cugugugaca aauuuagugg ccauccca                                              28

<210> SEQ ID NO 6
<211> LENGTH: 28
<212> TYPE: RNA
<213> ORGANISM: Homo sapiens

<400> SEQUENCE: 6
gacuauggug caacagcaga agagcugg                                              28

<210> SEQ ID NO 7
<211> LENGTH: 28
<212> TYPE: RNA
<213> ORGANISM: Homo sapiens

<400> SEQUENCE: 7
cgagguagag aagcagauga auaugagu                                              28

<210> SEQ ID NO 8
<211> LENGTH: 28
<212> TYPE: RNA
<213> ORGANISM: Homo sapiens

<400> SEQUENCE: 8
cagugguuuu aacagcaggc cccggggu                                              28

<210> SEQ ID NO 9
<211> LENGTH: 28
<212> TYPE: RNA
<213> ORGANISM: Homo sapiens

<400> SEQUENCE: 9
agagcgacau caugguauuc cccuuacu                                              28

<210> SEQ ID NO 10
<211> LENGTH: 28
<212> TYPE: RNA
<213> ORGANISM: Homo sapiens

<400> SEQUENCE: 10
gguagagaag cagaugaaua ugagucca                                              28

<210> SEQ ID NO 11
<211> LENGTH: 28
<212> TYPE: RNA
<213> ORGANISM: Homo sapiens

<400> SEQUENCE: 11
auugaggaga agauggaggc ugaugccc                                              28
```

```
<210> SEQ ID NO 12
<211> LENGTH: 28
<212> TYPE: RNA
<213> ORGANISM: Homo sapiens

<400> SEQUENCE: 12
ggaggaagaa gcugagaagc uaaaggag                                    28

<210> SEQ ID NO 13
<211> LENGTH: 28
<212> TYPE: RNA
<213> ORGANISM: Homo sapiens

<400> SEQUENCE: 13
aacgagguag agaagcagau gaauauga                                    28

<210> SEQ ID NO 14
<211> LENGTH: 20
<212> TYPE: RNA
<213> ORGANISM: Artificial sequence
<220> FEATURE:
<223> OTHER INFORMATION: Effector sequence for shmiR2

<400> SEQUENCE: 14
agcagaugaa uaugagucca                                             20

<210> SEQ ID NO 15
<211> LENGTH: 21
<212> TYPE: RNA
<213> ORGANISM: Artificial sequence
<220> FEATURE:
<223> OTHER INFORMATION: Effector complement sequence for shmiR2

<400> SEQUENCE: 15
uggacucaua uucaucugcu u                                           21

<210> SEQ ID NO 16
<211> LENGTH: 20
<212> TYPE: RNA
<213> ORGANISM: Artificial sequence
<220> FEATURE:
<223> OTHER INFORMATION: Effector sequence for shmiR3

<400> SEQUENCE: 16
gagguagaga agcagaugaa                                             20

<210> SEQ ID NO 17
<211> LENGTH: 21
<212> TYPE: RNA
<213> ORGANISM: Artificial sequence
<220> FEATURE:
<223> OTHER INFORMATION: Effector complement sequence for shmiR3

<400> SEQUENCE: 17
uucaucugcu ucucuaccuc g                                           21

<210> SEQ ID NO 18
<211> LENGTH: 20
<212> TYPE: RNA
<213> ORGANISM: Artificial sequence
<220> FEATURE:
<223> OTHER INFORMATION: Effector sequence for shmiR4

<400> SEQUENCE: 18
cugagaagcu aaaggagcua                                             20
```

```
<210> SEQ ID NO 19
<211> LENGTH: 21
<212> TYPE: RNA
<213> ORGANISM: Artificial sequence
<220> FEATURE:
<223> OTHER INFORMATION: Effector complement sequence for shmiR4

<400> SEQUENCE: 19
uagcuccuuu agcuucucag c                                              21

<210> SEQ ID NO 20
<211> LENGTH: 20
<212> TYPE: RNA
<213> ORGANISM: Artificial sequence
<220> FEATURE:
<223> OTHER INFORMATION: Effector sequence for shmiR5

<400> SEQUENCE: 20
uagagcgaca ucaugguauu                                                20

<210> SEQ ID NO 21
<211> LENGTH: 21
<212> TYPE: RNA
<213> ORGANISM: Artificial sequence
<220> FEATURE:
<223> OTHER INFORMATION: Effector complement sequence for shmiR5

<400> SEQUENCE: 21
aauaccauga ugucgcucua g                                              21

<210> SEQ ID NO 22
<211> LENGTH: 20
<212> TYPE: RNA
<213> ORGANISM: Artificial sequence
<220> FEATURE:
<223> OTHER INFORMATION: Effector sequence for shmiR6

<400> SEQUENCE: 22
gugacaaauu uaguggccau                                                20

<210> SEQ ID NO 23
<211> LENGTH: 21
<212> TYPE: RNA
<213> ORGANISM: Artificial sequence
<220> FEATURE:
<223> OTHER INFORMATION: Effector complement sequence for shmiR6

<400> SEQUENCE: 23
auggccacua aauuugucac a                                              21

<210> SEQ ID NO 24
<211> LENGTH: 20
<212> TYPE: RNA
<213> ORGANISM: Artificial sequence
<220> FEATURE:
<223> OTHER INFORMATION: Effector sequence for shmiR7

<400> SEQUENCE: 24
auggugcaac agcagaagag                                                20

<210> SEQ ID NO 25
<211> LENGTH: 21
<212> TYPE: RNA
<213> ORGANISM: Artificial sequence
<220> FEATURE:
<223> OTHER INFORMATION: Effector complement sequence for shmiR7
```

-continued

```
<400> SEQUENCE: 25
cucuucugcu guugcaccau a                                              21

<210> SEQ ID NO 26
<211> LENGTH: 20
<212> TYPE: RNA
<213> ORGANISM: Artificial sequence
<220> FEATURE:
<223> OTHER INFORMATION: Effector sequence for shmiR9

<400> SEQUENCE: 26
guagagaagc agaugaauau                                                20

<210> SEQ ID NO 27
<211> LENGTH: 21
<212> TYPE: RNA
<213> ORGANISM: Artificial sequence
<220> FEATURE:
<223> OTHER INFORMATION: Effector complement sequence for shmiR9

<400> SEQUENCE: 27
auauucaucu gcuucucuac c                                              21

<210> SEQ ID NO 28
<211> LENGTH: 20
<212> TYPE: RNA
<213> ORGANISM: Artificial sequence
<220> FEATURE:
<223> OTHER INFORMATION: Effector sequence for shmiR11

<400> SEQUENCE: 28
gguuuuaaca gcaggccccg                                                20

<210> SEQ ID NO 29
<211> LENGTH: 21
<212> TYPE: RNA
<213> ORGANISM: Artificial sequence
<220> FEATURE:
<223> OTHER INFORMATION: Effector complement sequence for shmiR11

<400> SEQUENCE: 29
cggggccugc uguuaaaacc a                                              21

<210> SEQ ID NO 30
<211> LENGTH: 20
<212> TYPE: RNA
<213> ORGANISM: Artificial sequence
<220> FEATURE:
<223> OTHER INFORMATION: Effector sequence for shmiR13

<400> SEQUENCE: 30
cgacaucaug guauuccccu                                                20

<210> SEQ ID NO 31
<211> LENGTH: 21
<212> TYPE: RNA
<213> ORGANISM: Artificial sequence
<220> FEATURE:
<223> OTHER INFORMATION: Effector complement sequence for shmiR13

<400> SEQUENCE: 31
aggggaauac caugaugucg c                                              21

<210> SEQ ID NO 32
```

```
<211> LENGTH: 20
<212> TYPE: RNA
<213> ORGANISM: Artificial sequence
<220> FEATURE:
<223> OTHER INFORMATION: Effector sequence for shmiR14

<400> SEQUENCE: 32
gagaagcaga ugaauaugag                                          20

<210> SEQ ID NO 33
<211> LENGTH: 21
<212> TYPE: RNA
<213> ORGANISM: Artificial sequence
<220> FEATURE:
<223> OTHER INFORMATION: Effector complement sequence for shmiR14

<400> SEQUENCE: 33
cucauauuca ucugcuucuc u                                        21

<210> SEQ ID NO 34
<211> LENGTH: 20
<212> TYPE: RNA
<213> ORGANISM: Artificial sequence
<220> FEATURE:
<223> OTHER INFORMATION: Effector sequence for shmiR15

<400> SEQUENCE: 34
aggagaagau ggaggcugau                                          20

<210> SEQ ID NO 35
<211> LENGTH: 21
<212> TYPE: RNA
<213> ORGANISM: Artificial sequence
<220> FEATURE:
<223> OTHER INFORMATION: Effector complement sequence for shmiR15

<400> SEQUENCE: 35
aucagccucc aucuucuccu c                                        21

<210> SEQ ID NO 36
<211> LENGTH: 20
<212> TYPE: RNA
<213> ORGANISM: Artificial sequence
<220> FEATURE:
<223> OTHER INFORMATION: Effector sequence for shmiR16

<400> SEQUENCE: 36
gaagaagcug agaagcuaaa                                          20

<210> SEQ ID NO 37
<211> LENGTH: 21
<212> TYPE: RNA
<213> ORGANISM: Artificial sequence
<220> FEATURE:
<223> OTHER INFORMATION: Effector complement sequence for shmiR16

<400> SEQUENCE: 37
uuuagcuucu cagcuucuuc c                                        21

<210> SEQ ID NO 38
<211> LENGTH: 20
<212> TYPE: RNA
<213> ORGANISM: Artificial sequence
<220> FEATURE:
<223> OTHER INFORMATION: Effector sequence for shmiR17

<400> SEQUENCE: 38
```
agguagagaa gcagaugaau                                                      20

<210> SEQ ID NO 39
<211> LENGTH: 21
<212> TYPE: RNA
<213> ORGANISM: Artificial sequence
<220> FEATURE:
<223> OTHER INFORMATION: Effector complement sequence for shmiR17

<400> SEQUENCE: 39
auucaucugc uucucuaccu c                                                    21

<210> SEQ ID NO 40
<211> LENGTH: 18
<212> TYPE: RNA
<213> ORGANISM: Artificial sequence
<220> FEATURE:
<223> OTHER INFORMATION: Stem loop

<400> SEQUENCE: 40
acugugaagc agaugggu                                                        18

<210> SEQ ID NO 41
<211> LENGTH: 26
<212> TYPE: RNA
<213> ORGANISM: Artificial sequence
<220> FEATURE:
<223> OTHER INFORMATION: 5' flanking sequence of the pri-miRNA backbone
<220> FEATURE:
<221> NAME/KEY: misc_feature
<222> LOCATION: (26)..(26)
<223> OTHER INFORMATION: n is u or a

<400> SEQUENCE: 41
gguauauugc uguugacagu gagcgn                                               26

<210> SEQ ID NO 42
<211> LENGTH: 22
<212> TYPE: RNA
<213> ORGANISM: Artificial sequence
<220> FEATURE:
<223> OTHER INFORMATION: 3' flanking sequence of the pri-miRNA backbone

<400> SEQUENCE: 42
cgccuacugc cucggacuuc aa                                                   22

<210> SEQ ID NO 43
<211> LENGTH: 107
<212> TYPE: RNA
<213> ORGANISM: Artificial sequence
<220> FEATURE:
<223> OTHER INFORMATION: RNA sequence encoding shmiR2

<400> SEQUENCE: 43
gguauauugc uguugacagu gagcguagca gaugaauaug aguccaacug ugaagcagau          60
ggguuggacu cauauucauc ugcuucgccu acugccucgg acuucaa                       107

<210> SEQ ID NO 44
<211> LENGTH: 107
<212> TYPE: RNA
<213> ORGANISM: Artificial sequence
<220> FEATURE:
<223> OTHER INFORMATION: RNA sequence encoding shmiR3

<400> SEQUENCE: 44

```
gguauauugc uguugacagu gagcgagagg uagagaagca gaugaaacug ugaagcagau        60
ggguuucauc ugcuucucua ccucgcgccu acugccucgg acuucaa                    107
```

<210> SEQ ID NO 45
<211> LENGTH: 107
<212> TYPE: RNA
<213> ORGANISM: Artificial sequence
<220> FEATURE:
<223> OTHER INFORMATION: RNA sequence encoding shmiR4

<400> SEQUENCE: 45

```
gguauauugc uguugacagu gagcgacuga gaagcuaaag gagcuaacug ugaagcagau        60
ggguuagcuc cuuuagcuuc ucagccgccu acugccucgg acuucaa                    107
```

<210> SEQ ID NO 46
<211> LENGTH: 107
<212> TYPE: RNA
<213> ORGANISM: Artificial sequence
<220> FEATURE:
<223> OTHER INFORMATION: RNA sequence encoding shmiR5

<400> SEQUENCE: 46

```
gguauauugc uguugacagu gagcgauaga gcgacaucau gguauuacug ugaagcagau        60
ggguaauacc augaugucgc ucuagcgccu acugccucgg acuucaa                    107
```

<210> SEQ ID NO 47
<211> LENGTH: 107
<212> TYPE: RNA
<213> ORGANISM: Artificial sequence
<220> FEATURE:
<223> OTHER INFORMATION: RNA sequence encoding shmiR6

<400> SEQUENCE: 47

```
gguauauugc uguugacagu gagcgaguga caaauuuagu ggccauacug ugaagcagau        60
ggguauggcc acuaaauuug ucacacgccu acugccucgg acuucaa                    107
```

<210> SEQ ID NO 48
<211> LENGTH: 107
<212> TYPE: RNA
<213> ORGANISM: Artificial sequence
<220> FEATURE:
<223> OTHER INFORMATION: RNA sequence encoding shmiR7

<400> SEQUENCE: 48

```
gguauauugc uguugacagu gagcgaaugg ugcaacagca gaagagacug ugaagcagau        60
gggucucuuc ugcuguugca ccauacgccu acugccucgg acuucaa                    107
```

<210> SEQ ID NO 49
<211> LENGTH: 107
<212> TYPE: RNA
<213> ORGANISM: Artificial sequence
<220> FEATURE:
<223> OTHER INFORMATION: RNA sequence encoding shmiR9

<400> SEQUENCE: 49

```
gguauauugc uguugacagu gagcgaguag agaagcagau gaauauacug ugaagcagau        60
ggguauauuc aucugcuucu cuacccgccu acugccucgg acuucaa                    107
```

<210> SEQ ID NO 50
<211> LENGTH: 107
<212> TYPE: RNA
<213> ORGANISM: Artificial sequence

```
<220> FEATURE:
<223> OTHER INFORMATION: RNA sequence encoding shmiR11

<400> SEQUENCE: 50
gguauauugc uguugacagu gagcgagguu uuaacagcag gccccgacug ugaagcagau      60
gggucggggc cugcuguuaa aaccacgccu acugccucgg acuucaa                  107

<210> SEQ ID NO 51
<211> LENGTH: 107
<212> TYPE: RNA
<213> ORGANISM: Artificial sequence
<220> FEATURE:
<223> OTHER INFORMATION: RNA sequence encoding shmiR13

<400> SEQUENCE: 51
gguauauugc uguugacagu gagcgacgac aucaugguau uccccuacug ugaagcagau      60
ggguagggga auaccaugau gucgccgccu acugccucgg acuucaa                  107

<210> SEQ ID NO 52
<211> LENGTH: 107
<212> TYPE: RNA
<213> ORGANISM: Artificial sequence
<220> FEATURE:
<223> OTHER INFORMATION: RNA sequence encoding shmiR14

<400> SEQUENCE: 52
gguauauugc uguugacagu gagcgugaga agcagaugaa uaugagacug ugaagcagau      60 ggguucucaua uucaucugcu ucucucgccu acugccucgg acuucaa                 107

<210> SEQ ID NO 53
<211> LENGTH: 107
<212> TYPE: RNA
<213> ORGANISM: Artificial sequence
<220> FEATURE:
<223> OTHER INFORMATION: RNA sequence encoding shmiR15

<400> SEQUENCE: 53
gguauauugc uguugacagu gagcgaagga gaagauggag gcugauacug ugaagcagau      60
ggguaucagc cuccaucuuc uccuccgccu acugccucgg acuucaa                  107

<210> SEQ ID NO 54
<211> LENGTH: 107
<212> TYPE: RNA
<213> ORGANISM: Artificial sequence
<220> FEATURE:
<223> OTHER INFORMATION: RNA sequence encoding shmiR16

<400> SEQUENCE: 54
gguauauugc uguugacagu gagcgagaag aagcugagaa gcuaaaacug ugaagcagau      60
ggguuuuagc uucucagcuu cuucccgccu acugccucgg acuucaa                  107

<210> SEQ ID NO 55
<211> LENGTH: 107
<212> TYPE: RNA
<213> ORGANISM: Artificial sequence
<220> FEATURE:
<223> OTHER INFORMATION: RNA sequence encoding shmiR17

<400> SEQUENCE: 55
gguauauugc uguugacagu gagcgaaggu agagaagcag augaauacug ugaagcagau      60
ggguauucau cugcuucucu accuccgccu acugccucgg acuucaa                  107
```

-continued

<210> SEQ ID NO 56
<211> LENGTH: 107
<212> TYPE: DNA
<213> ORGANISM: Artificial sequence
<220> FEATURE:
<223> OTHER INFORMATION: DNA sequence encoding shmiR2

<400> SEQUENCE: 56
ggtatattgc tgttgacagt gagcgtagca gatgaatatg agtccaactg tgaagcagat    60
gggttggact catattcatc tgcttcgcct actgcctcgg acttcaa    107

<210> SEQ ID NO 57
<211> LENGTH: 107
<212> TYPE: DNA
<213> ORGANISM: Artificial sequence
<220> FEATURE:
<223> OTHER INFORMATION: DNA sequence encoding shmiR3

<400> SEQUENCE: 57
ggtatattgc tgttgacagt gagcgagagg tagagaagca gatgaaactg tgaagcagat    60
gggtttcatc tgcttctcta cctcgcgcct actgcctcgg acttcaa    107

<210> SEQ ID NO 58
<211> LENGTH: 107
<212> TYPE: DNA
<213> ORGANISM: Artificial sequence
<220> FEATURE:
<223> OTHER INFORMATION: DNA sequence encoding shmiR4

<400> SEQUENCE: 58
ggtatattgc tgttgacagt gagcgactga gaagctaaag gagctaactg tgaagcagat    60
gggttagctc ctttagcttc tcagccgcct actgcctcgg acttcaa    107

<210> SEQ ID NO 59
<211> LENGTH: 107
<212> TYPE: DNA
<213> ORGANISM: Artificial sequence
<220> FEATURE:
<223> OTHER INFORMATION: DNA sequence encoding shmiR5

<400> SEQUENCE: 59
ggtatattgc tgttgacagt gagcgataga gcgacatcat ggtattactg tgaagcagat    60
gggtaatacc atgatgtcgc tctagcgcct actgcctcgg acttcaa    107

<210> SEQ ID NO 60
<211> LENGTH: 107
<212> TYPE: DNA
<213> ORGANISM: Artificial sequence
<220> FEATURE:
<223> OTHER INFORMATION: DNA sequence encoding shmiR6

<400> SEQUENCE: 60
ggtatattgc tgttgacagt gagcgagtga caaatttagt ggccatactg tgaagcagat    60
gggtatggcc actaaatttg tcacacgcct actgcctcgg acttcaa    107

<210> SEQ ID NO 61
<211> LENGTH: 107
<212> TYPE: DNA
<213> ORGANISM: Artificial sequence
<220> FEATURE:
<223> OTHER INFORMATION: DNA sequence encoding shmiR7

<400> SEQUENCE: 61

```
ggtatattgc tgttgacagt gagcgaatgg tgcaacagca aaagagactg tgaagcagat      60
gggtctcttc tgctgttgca ccatacgcct actgcctcgg acttcaa                  107
```

<210> SEQ ID NO 62
<211> LENGTH: 107
<212> TYPE: DNA
<213> ORGANISM: Artificial sequence
<220> FEATURE:
<223> OTHER INFORMATION: DNA sequence encoding shmiR9

<400> SEQUENCE: 62

```
ggtatattgc tgttgacagt gagcgagtag agaagcagat gaatatactg tgaagcagat      60
gggtatattc atctgcttct ctacccgcct actgcctcgg acttcaa                  107
```

<210> SEQ ID NO 63
<211> LENGTH: 107
<212> TYPE: DNA
<213> ORGANISM: Artificial sequence
<220> FEATURE:
<223> OTHER INFORMATION: DNA sequence encoding shmiR11

<400> SEQUENCE: 63

```
ggtatattgc tgttgacagt gagcgaggtt ttaacagcag cccccgactg tgaagcagat      60
gggtcggggc ctgctgttaa aaccacgcct actgcctcgg acttcaa                  107
```

<210> SEQ ID NO 64
<211> LENGTH: 107
<212> TYPE: DNA
<213> ORGANISM: Artificial sequence
<220> FEATURE:
<223> OTHER INFORMATION: DNA sequence encoding shmiR13

<400> SEQUENCE: 64

```
ggtatattgc tgttgacagt gagcgacgac atcatggtat tcccctactg tgaagcagat      60
gggtagggga ataccatgat gtcgccgcct actgcctcgg acttcaa                  107
```

<210> SEQ ID NO 65
<211> LENGTH: 107
<212> TYPE: DNA
<213> ORGANISM: Artificial sequence
<220> FEATURE:
<223> OTHER INFORMATION: DNA sequence encoding shmiR14

<400> SEQUENCE: 65

```
ggtatattgc tgttgacagt gagcgtgaga agcagatgaa tatgagactg tgaagcagat      60
gggtctcata ttcatctgct tctctcgcct actgcctcgg acttcaa                  107
```

<210> SEQ ID NO 66
<211> LENGTH: 107
<212> TYPE: DNA
<213> ORGANISM: Artificial sequence
<220> FEATURE:
<223> OTHER INFORMATION: DNA sequence encoding shmiR15

<400> SEQUENCE: 66

```
ggtatattgc tgttgacagt gagcgaagga gaagatggag gctgatactg tgaagcagat      60
gggtatcagc ctccatcttc tcctccgcct actgcctcgg acttcaa                  107
```

<210> SEQ ID NO 67
<211> LENGTH: 107
<212> TYPE: DNA

```
<213> ORGANISM: Artificial sequence
<220> FEATURE:
<223> OTHER INFORMATION: DNA sequence encoding shmiR16

<400> SEQUENCE: 67
ggtatattgc tgttgacagt gagcgagaag aagctgagaa gctaaaactg tgaagcagat      60
gggttttagc ttctcagctt cttcccgcct actgcctcgg acttcaa                  107

<210> SEQ ID NO 68
<211> LENGTH: 107
<212> TYPE: DNA
<213> ORGANISM: Artificial sequence
<220> FEATURE:
<223> OTHER INFORMATION: DNA sequence encoding shmiR17

<400> SEQUENCE: 68
ggtatattgc tgttgacagt gagcgaaggt agagaagcag atgaatactg tgaagcagat      60
gggtattcat ctgcttctct acctccgcct actgcctcgg acttcaa                  107

<210> SEQ ID NO 69
<211> LENGTH: 2532
<212> TYPE: DNA
<213> ORGANISM: Artificial sequence
<220> FEATURE:
<223> OTHER INFORMATION: Double expression construct version 1 coding
      for shmiR3, shmiR14 and codon optimized PABPN1

<400> SEQUENCE: 69
cgatcgcgcg cagatctgtc atgatgatcc tagcatgctg cccatgtaag gaggcaaggc      60
ctggggacac ccgagatgcc tggttataat taacccagac atgtggctgc ccccccccc     120 ccaacacctg ctgcctctaa aaataaccct gcatgccatg ttcccggcga agggccagct    180
gtcccccgcc agctagactc agcacttagt ttaggaacca gtgagcaagt cagcccttgg    240
ggcagcccat acaaggccat ggggctgggc aagctcacg cctgggtccg ggtgggcac     300 ggtgcccggg caacgagctg aaagctcatc tgctctcagg ggcccctccc tggggacagc    360
ccctcctggc tagtcacacc ctgtaggctc tctatataa cccaggggca caggggctgc     420
cctcattcta ccaccacctc cacagcacag acagacactc aggagccagc cagcgtcgat    480
cattgaagtt actattccga agttcctatt ctctagaatt cgccaccacg cgtggtatat    540
tgctgttgac agtgagcgag aggtagagaa gcagatgaaa ctgtgaagca gatgggtttc    600
atctgcttct ctacctcgcg cctactgcct cggacttcaa atcatctact ccatggccct    660
ctgcgtttgc tgaagacaga accgcaaagc aggacccgac aggattctcc ccgcctcttc    720
agagactatg tttacaagat atcggtatat tgctgttgac agtgagcgtg agaagcagat    780
gaatatgaga ctgtgaagca gatgggtctc atattcatct gcttctctcg cctactgcct    840
cggacttcaa gtcgacgcta gcaataaagg atcctttatt ttcattggat ccgtgtgttg    900
gttttttgtg tgcggttaat taaggtaccc gagctccacc gcggtggcgg ccgtccgccc    960
tcggcaccat cctcacgaca cccaaatatg gcgacgggtg aggaatggtg gggagttatt   1020
tttagagcgg tgaggaaggt gggcaggcag caggtgttgg cgctctaaaa ataactcccg   1080
ggagttattt ttagagcgga ggaatggtgg acacccaaat atggcgacgg ttcctcaccc   1140
gtcgccatat ttgggtgtcc gccctcggcc ggggccgcat tcctgggggc cgggcggtgc   1200
tcccgcccgc tcgataaaa ggctccgggg ccggcggcgg cccacgagct acccggagga   1260
gcgggaggcg ccaagctcta gaactagtgg atccccgggg ctgcaggaat tcgatgccac   1320
```

```
catggccgct gccgccgctg ctgctgccgc agccggcgct gccggcggaa gaggcagcgg    1380
ccctggcaga cggcggcatc tggtccctgg cgccggaggg gaggccggcg aaggcgcccc    1440
tggcggagcc ggcgactacg gcaacggcct ggaaagcgag gaactggaac ccgaggaact    1500
gctgctggaa cctgagcccg agccagagcc cgaggaagag cccctaggc caagagcccc    1560 ccctggcgcc ccaggaccag gaccaggctc tggggcacca ggctctcagg aagaggaaga    1620
agagcccggc ctcgtcgagg gagacccagg cgatggcgct atcgaagatc cgagctgga    1680 agccatcaag gccagagtgc gggagatgga agaggaggcc gaaaaattga aagagctgca    1740
gaacgaagtc gaaaaacaaa tgaacatgtc ccccctcct ggaaatgctg ccctgtgat    1800 catgagcatc gaggaaaaga tggaagccga cgcccggtct atctacgtgg caacgtgga    1860 ctacggcgcc accgccgaag aactggaagc ccactttcac ggctgtggca gcgtgaaccg    1920
ggtgaccatc ctgtgcgaca gttcagcgg ccaccccaag ggcttcgcct acatcgagtt    1980
cagcgacaaa gaaagcgtgc ggacctctct ggctctcgac gagtctctgt tcaggggaag    2040
gcagatcaag gtcatcccca gcggaccaa caggcccggc atcagcacca ccgacagagg    2100
cttccctagg gctaggtaca gagcccggac caccaactac aacagcagca gaagccggtt    2160
ctacagcggc ttcaattctc ggcctagagg cagagtgtac cggggcaggg ccagggccac    2220
ctcctggtac agcccctacg aacagaagct gatcagcgag gaagatctgt gatgagatat    2280
ctgatgacat atgacgcgtt taattaactg tgccttctag ttgccagcca tctgttgttt    2340
gcccctcccc cgtgccttcc ttgaccctgg aaggtgccac tcccactgtc ctttcctaat    2400
aaaatgagga aattgcatcg cattgtctga gtaggtgtca ttctattctg ggggtgggg    2460 tggggcagga cagcaagggg gaggattggg aagacaatag caggcatgct ggggatgcgg    2520
tgggctctat gg                                                        2532
```

<210> SEQ ID NO 70
<211> LENGTH: 2532
<212> TYPE: DNA
<213> ORGANISM: Artificial sequence
<220> FEATURE:
<223> OTHER INFORMATION: Double expression construct version 1 coding
      for shmiR17, shmiR13 and codon optimized PABPN1

<400> SEQUENCE: 70

```
cgatcgcgcg cagatctgtc atgatgatcc tagcatgctg cccatgtaag gaggcaaggc      60
ctggggacac ccgagatgcc tggttataat taacccagac atgtggctgc cccccccccc     120
ccaacacctg ctgcctctaa aaataaccct gcatgccatg ttcccggcga agggccagct     180
gtcccccgcc agctagactc agcacttagt ttaggaacca gtgagcaagt cagcccttgg     240
ggcagcccat acaaggccat ggggctgggc aagctgcacg cctgggtccg gggtgggcac     300
ggtgcccggg caacgagctg aaagctcatc tgctctcagg ggcccctccc tggggacagc     360
ccctcctggc tagtcacacc ctgtaggctc tctatataa cccaggggca caggggctgc     420
cctcattcta ccaccacctc cacagcacag acagacactc aggagccagc cagcgtcgat     480
cattgaagtt actattccga agttcctatt ctctagaatt cgccaccacg cgtggtatat     540
tgctgttgac agtgagcgaa ggtagagaag cagatgaata ctgtgaagca gatgggtatt     600
catctgcttc tctacctccg cctactgcct cggacttcaa atcatctact ccatggccct     660
ctgcgtttgc tgaagacaga accgcaaagc aggacccgac aggattctcc ccgcctcttc     720
agagactatg tttacaagat atcggtatat tgctgttgac agtgagcgac gacatcatgg     780
```

```
tattccccta ctgtgaagca gatgggtagg ggaataccat gatgtcgccg cctactgcct    840
cggacttcaa gtcgacgcta gcaataaagg atcctttatt ttcattggat ccgtgtgttg    900
gttttttgtg tgcggttaat taaggtaccc gagctccacc gcggtggcgg ccgtccgccc    960
tcggcaccat cctcacgaca cccaaatatg gcgacgggtg aggaatggtg gggagttatt   1020
tttagagcgg tgaggaaggt gggcaggcag caggtgttgg cgctctaaaa ataactcccg   1080
ggagttattt ttagagcgga ggaatggtgg acacccaaat atggcgacgg ttcctcaccc   1140
gtcgccatat ttgggtgtcc gccctcggcc ggggccgcat tcctggggc cgggcggtgc    1200 tcccgcccgc ctcgataaaa ggctccgggg ccggcggcgg cccacgagct acccggagga   1260
gcgggaggcg ccaagctcta gaactagtgg atccccgggg ctgcaggaat tcgatgccac   1320
catggccgct gccgccgctg ctgctgccgc agccggcgct gccggcgaa gaggcagcgg    1380 ccctggcaga cggcggcatc tggtccctgg cgccggaggg gaggccggcg aaggcgcccc   1440
tggcggagcc ggcgactacg gcaacggcct ggaaagcgag gaactggaac ccgaggaact   1500
gctgctggaa cctgagcccg agccagagcc cgaggaagag cccctaggc caagagcccc    1560 ccctggcgcc ccaggaccag gaccaggctc tggggcacca ggctctcagg aagaggaaga   1620
agagcccggc ctcgtcgagg gagacccagg cgatggcgct atcgaagatc ccgagctgga   1680
agccatcaag gccagagtgc gggagatgga agaggaggcc gaaaaattga agagctgca    1740 gaacgaagtc gaaaaacaaa tgaacatgtc ccccctcct ggaaatgctg ccctgtgat    1800 catgagcatc gaggaaaaga tggaagccga cgcccggtct atctacgtgg caacgtgga    1860 ctacggcgca accgccgaag aactggaagc ccactttcac ggctgtggca gcgtgaaccg   1920
ggtgaccatc ctgtgcgaca gttcagcgg ccaccccaag ggcttcgcct acatcgagtt    1980
cagcgacaaa gaaagcgtgc ggacctctct ggctctcgac gagtctctgt tcaggggaag   2040
gcagatcaag gtcatcccca gcggaccaa caggcccggc atcagcacca ccgacagagg    2100
cttccctagg gctaggtaca gagcccggac caccaactac aacagcagca gaagccggtt   2160
ctacagcggc ttcaattctc ggcctagagg cagagtgtac cggggcaggg ccagggccac   2220
ctcctggtac agcccctacg aacagaagct gatcagcgag gaagatctgt gatgagatat   2280
ctgatgacat atgacgcgtt taattaactg tgccttctag ttgccagcca tctgttgttt   2340
gccccctccc cgtgccttcc ttgacccctgg aaggtgccac tcccactgtc ctttcctaat   2400
aaaatgagga aattgcatcg cattgtctga gtaggtgtca ttctattctg gggggtgggg   2460
tggggcagga cagcaagggg gaggattggg aagacaatag caggcatgct ggggatgcgg   2520
tgggctctat gg                                                      2532
```

<210> SEQ ID NO 71
<211> LENGTH: 1943
<212> TYPE: DNA
<213> ORGANISM: Artificial sequence
<220> FEATURE:
<223> OTHER INFORMATION: Double expression construct version 2 coding
      for shmiR3, shmiR14 and codon optimized PABPN1

<400> SEQUENCE: 71

```
cgagctccac cgcggtggcg gccgtccgcc ctcggcacca cctcacgac acccaaatat    60 ggcgacgggt gaggaatggt ggggagttat ttttagagcg gtgaggaagg tgggcaggca   120
gcaggtgttg gcgctctaaa ataactcccg ggagttattt ttagagcgg aggaatggtg   180 gacacccaaa tatggcgacg gttcctcacc cgtcgccata tttgggtgtc cgccctcggc    240
```

```
cggggccgca ttcctggggg ccgggcggtg ctcccgcccg cctcgataaa aggctccggg    300
gccggcggcg gcccacgagc tacccggagg agcgggaggc gccaagctct agaactagtg    360 gatccccccgg gctgcaggaa ttcgatgcca ccatggccgc tgccgccgct gctgctgccg    420
cagccggcgc tgccggcgga agaggcagcg gccctggcag acggcggcat ctggtccctg    480
gcgccggagg ggaggccggc gaaggcgccc ctggcggagc cggcgactac ggcaacggcc    540
tggaaagcga ggaactggaa cccgaggaac tgctgctgga acctgagccc gagccagagc    600
ccgaggaaga gcccctagg ccaagagccc ccctggcgc cccaggacca ggaccaggct    660
ctggggcacc aggctctcag gaagaggaag aagagcccgg cctcgtcgag ggagacccag    720
gcgatggcgc tatcgaagat cccgagctgg aagccatcaa ggccagagtg cgggagatgg    780
aagaggaggc cgaaaaattg aaagagctgc agaacgaagt cgaaaaacaa atgaacatgt    840 cccccccctcc tggaaatgct ggccctgtga tcatgagcat cgaggaaaag atggaagccg    900
acgcccggtc tatctacgtg ggcaacgtgg actacggcgc caccgccgaa gaactggaag    960
cccactttca cggctgtggc agcgtgaacc gggtgaccat cctgtgcgac aagttcagcg   1020 gccacccccaa gggcttcgcc tacatcgagt tcagcgacaa agaaagcgtg cggacctctc   1080
tggctctcga cgagtctctg ttcagggaa ggcagatcaa ggtcatcccc aagcggacca   1140
acaggcccgg catcagcacc accgacagag gcttccctag gctaggtac agagcccgga   1200 ccaccaacta caacagcagc agaagccggt tctacagcgg cttcaattct cggcctagag   1260
gcagagtgta ccggggcagg gccagggcca cctcctggta cagcccctac tgatgacata   1320
tgacgcgtgg tatattgctg ttgacagtga gcgagaggta gagaagcaga tgaaactgtg   1380
aagcagatgg gtttcatctg cttctctacc tcgcgcctac tgcctcggac ttcaaatcat   1440
ctactccatg gccctctgcg tttgctgaag acagaaccgc aaagcaggac ccgacaggat   1500
tctccccgcc tcttcagaga ctatgtttac aagatatcgg tatattgctg ttgacagtga   1560
gcgtgagaag cagatgaata tgagactgtg aagcagatgg gtctcatatt catctgcttc   1620
tctcgcctac tgcctcggac ttcaagtcga cgctagcaat aaaggatcct ttattttcat   1680
tggatccgtg tgttggtttt tgtgtgcgg ttaattaact gtgccttcta gttgccagcc   1740
atctgttgtt tgcccctccc ccgtgccttc cttgaccctg gaaggtgcca ctcccactgt   1800
cctttcctaa taaaatgagg aaattgcatc gcattgtctg agtaggtgtc attctattct   1860
ggggggtggg gtggggcagg acagcaaggg ggaggattgg gaagacaata gcaggcatgc   1920
tggggatgcg gtgggctcta tgg                                          1943
```

<210> SEQ ID NO 72
<211> LENGTH: 1943
<212> TYPE: DNA
<213> ORGANISM: Artificial sequence
<220> FEATURE:
<223> OTHER INFORMATION: Double expression construct version 2 coding
      for shmiR17, shmiR13 and codon optimized PABPN1

<400> SEQUENCE: 72

```
cgagctccac cgcggtggcg gccgtccgcc ctcggcacca tcctcacgac acccaaatat     60
ggcgacgggt gaggaatggt ggggagttat tttagagcg gtgaggaagg tgggcaggca    120
gcaggtgttg gcgctctaaa ataactcccc gggagttatt tttagagcgg aggaatggtg    180
gacacccaaa tatggcgacg gttcctcacc cgtcgccata tttgggtgtc cgccctcggc    240
cggggccgca ttcctggggg ccgggcggtg ctcccgcccg cctcgataaa aggctccggg    300
```

```
gccggcggcg gcccacgagc tacccggagg agcgggaggc gccaagctct agaactagtg    360
gatccccgg  gctgcaggaa ttcgatgcca ccatggccgc tgccgccgct gctgctgccg    420
cagccggcgc tgccggcgga agaggcagcg gccctggcag acggcggcat ctggtccctg    480
gcgccggagg ggaggccggc gaaggcgccc ctggcggagc cggcgactac ggcaacggcc    540
tggaaagcga ggaactggaa cccgaggaac tgctgctgga acctgagccc gagccagagc    600
ccgaggaaga gcccctaggc caagagcccc ccctggcgc  ccaggaccag gaccaggct    660
ctggggcacc aggctctcag aagaggaag  aagagcccgg cctcgtcgag ggagacccag    720
gcgatggcgc tatcgaagat cccgagctgg aagccatcaa ggccagagtg cgggagatgg    780
aagaggaggc cgaaaaattg aaagagctgc agaacgaagt cgaaaaacaa atgaacatgt    840
ccccccctcc tggaaatgct ggccctgtga tcatgagcat cgaggaaaag atggaagccg    900
acgcccggtc tatctacgtg ggcaacgtgg actacggcgc caccgccgaa gaactggaag    960
cccactttca cggctgtggc agcgtgaacc gggtgaccat cctgtgcgac aagttcagcg   1020
gccacccaa  gggcttcgcc tacatcgagt tcagcgacaa agaaagcgtg cggacctctc   1080
tggctctcga cgagtctctg ttcagggaa  ggcagatcaa ggtcatcccc aagcggacca   1140
acaggcccgg catcagcacc accgacagag gcttccctag gctaggtac  agagcccgga   1200
ccaccaacta caacagcagc agaagccggt tctacagcgg cttcaattct cggcctagag   1260
gcagagtgta ccggggcagg gccagggcca cctcctggta cagcccctac tgatgacata   1320
tgacgcgtgg tatattgctg ttgacagtga gcgaaggtag agaagcagat gaatactgtg   1380
aagcagatgg gtattcatct gcttctctac ctccgcctac tgcctcggac ttcaaatcat   1440
ctactccatg gccctctgcg tttgctgaag acagaaccgc aaagcaggac ccgacaggat   1500
tctccccgcc tcttcagaga ctatgtttac aagtatcgg  tatattgctg ttgacagtga   1560
gcgacgacat catggtattc ccctactgtg aagcagatgg tagggaat  accatgatgt   1620
cgccgcctac tgcctcggac ttcaagtcga cgctagcaat aaaggatcct ttattttcat   1680
tggatccgtg tgttggtttt tgtgtgcgg  ttaattaact gtgccttcta gttgccagcc   1740
atctgttgtt tgcccctccc ccgtgccttc cttgaccctg gaaggtgcca ctcccactgt   1800
cctttcctaa taaaatgagg aaattgcatc gcattgtctg agtaggtgtc attctattct   1860
ggggggtggg gtggggcagg acagcaaggg ggaggattgg aagacaata  gcaggcatgc   1920
tggggatgcg gtgggctcta tgg                                           1943
```

<210> SEQ ID NO 73
<211> LENGTH: 921
<212> TYPE: DNA
<213> ORGANISM: Artificial sequence
<220> FEATURE:
<223> OTHER INFORMATION: Human codon-optimized PABPN1 cDNA sequence

<400> SEQUENCE: 73

```
atggccgctg ccgccgctgc tgctgccgca gccggcgctg ccggcggaag aggcagcggc     60
cctggcagac ggcggcatct ggtccctggc gccgaggggg aggccggcga aggcgcccct    120
ggcggagccg cgactacgg  caacggcctg aaagcgagg  aactggaacc cgaggaactg    180
ctgctggaac ctgagcccga gccagagccc gaggaagagc ccctaggcc  aagagccccc    240
ctggcgccc  aggaccagg  accaggctct ggggcaccag gctctcagga agaggaagaa    300
gagcccggc  tcgtcgaggg agacccaggc gatggcgcta tcgaagatcc cgagctggaa    360
gccatcaagg ccagagtgcg ggagatggaa gaggaggccg aaaaattgaa agagctgcag    420
```

```
aacgaagtcg aaaaacaaat gaacatgtcc cccctcctg gaaatgctgg ccctgtgatc      480
atgagcatcg aggaaaagat ggaagccgac gcccggtcta tctacgtggg caacgtggac      540
tacggcgcca ccgccgaaga actggaagcc cactttcacg gctgtggcag cgtgaaccgg      600
gtgaccatcc tgtgcgacaa gttcagcggc cacccaagg gcttcgccta catcgagttc      660
agcgacaaag aaagcgtgcg gacctctctg gctctcgacg agtctctgtt caggggaagg      720
cagatcaagg tcatcccccaa gcggaccaac aggcccggca tcagcaccac cgacagaggc      780
ttccctaggg ctaggtacag agcccggacc accaactaca acagcagcag aagccggttc      840
tacagcggct tcaattctcg gcctagaggc agagtgtacc ggggcagggc cagggccacc      900
tcctggtaca gcccctactg a                                                921
```

```
<210> SEQ ID NO 74
<211> LENGTH: 306
<212> TYPE: PRT
<213> ORGANISM: Artificial sequence
<220> FEATURE:
<223> OTHER INFORMATION: Human wildtype PABPN1 amino acid sequence

<400> SEQUENCE: 74

Met Ala Ala Ala Ala Ala Ala Ala Ala Ala Gly Ala Ala Gly Gly
1               5                   10                  15

Arg Gly Ser Gly Pro Gly Arg Arg His Leu Val Pro Gly Ala Gly
                20                  25                  30

Gly Glu Ala Gly Glu Gly Ala Pro Gly Gly Ala Gly Asp Tyr Gly Asn
                35                  40                  45

Gly Leu Glu Ser Glu Glu Leu Glu Pro Glu Glu Leu Leu Leu Glu Pro
        50                  55                  60

Glu Pro Glu Pro Glu Pro Glu Glu Pro Arg Pro Arg Ala Pro
65                  70                  75                  80

Pro Gly Ala Pro Gly Pro Gly Pro Gly Ser Gly Ala Pro Gly Ser Gln
                85                  90                  95

Glu Glu Glu Glu Glu Pro Gly Leu Val Glu Gly Asp Pro Gly Asp Gly
                100                 105                 110

Ala Ile Glu Asp Pro Glu Leu Glu Ala Ile Lys Ala Arg Val Arg Glu
            115                 120                 125

Met Glu Glu Glu Ala Glu Lys Leu Lys Glu Leu Gln Asn Glu Val Glu
        130                 135                 140

Lys Gln Met Asn Met Ser Pro Pro Gly Asn Ala Gly Pro Val Ile
145                 150                 155                 160

Met Ser Ile Glu Glu Lys Met Glu Ala Asp Ala Arg Ser Ile Tyr Val
                165                 170                 175

Gly Asn Val Asp Tyr Gly Ala Thr Ala Glu Glu Leu Glu Ala His Phe
            180                 185                 190

His Gly Cys Gly Ser Val Asn Arg Val Thr Ile Leu Cys Asp Lys Phe
        195                 200                 205

Ser Gly His Pro Lys Gly Phe Ala Tyr Ile Glu Phe Ser Asp Lys Glu
    210                 215                 220

Ser Val Arg Thr Ser Leu Ala Leu Asp Glu Ser Leu Phe Arg Gly Arg
225                 230                 235                 240

Gln Ile Lys Val Ile Pro Lys Arg Thr Asn Arg Pro Gly Ile Ser Thr
                245                 250                 255

Thr Asp Arg Gly Phe Pro Arg Ala Arg Tyr Arg Ala Arg Thr Thr Asn
            260                 265                 270
```

Tyr Asn Ser Ser Arg Ser Arg Phe Tyr Ser Gly Phe Asn Ser Arg Pro
            275                 280                 285

Arg Gly Arg Val Tyr Arg Gly Arg Ala Arg Ala Thr Ser Trp Tyr Ser
    290                 295                 300

Pro Tyr
305

<210> SEQ ID NO 75
<211> LENGTH: 314
<212> TYPE: PRT
<213> ORGANISM: Artificial sequence
<220> FEATURE:
<223> OTHER INFORMATION: Human wildtype PABPN1 amino acid sequence (with
      FLAG tag)

<400> SEQUENCE: 75

Met Ala Ala Ala Ala Ala Ala Ala Ala Gly Ala Ala Gly Gly
1               5                   10                  15

Arg Gly Ser Gly Pro Gly Arg Arg Arg His Leu Val Pro Gly Ala Gly
                20                  25                  30

Gly Glu Ala Gly Glu Gly Ala Pro Gly Gly Ala Gly Asp Tyr Gly Asn
            35                  40                  45

Gly Leu Glu Ser Glu Glu Leu Glu Pro Glu Glu Leu Leu Leu Glu Pro
        50                  55                  60

Glu Pro Glu Pro Glu Pro Glu Glu Pro Pro Arg Pro Arg Ala Pro
65                  70                  75                  80

Pro Gly Ala Pro Gly Pro Gly Pro Gly Ser Gly Ala Pro Gly Ser Gln
                85                  90                  95

Glu Glu Glu Glu Glu Pro Gly Leu Val Glu Gly Asp Pro Gly Asp Gly
            100                 105                 110

Ala Ile Glu Asp Pro Glu Leu Glu Ala Ile Lys Ala Arg Val Arg Glu
        115                 120                 125

Met Glu Glu Glu Ala Glu Lys Leu Lys Glu Leu Gln Asn Glu Val Glu
    130                 135                 140

Lys Gln Met Asn Met Ser Pro Pro Pro Gly Asn Ala Gly Pro Val Ile
145                 150                 155                 160

Met Ser Ile Glu Glu Lys Met Glu Ala Asp Ala Arg Ser Ile Tyr Val
                165                 170                 175

Gly Asn Val Asp Tyr Gly Ala Thr Ala Glu Glu Leu Glu Ala His Phe
            180                 185                 190

His Gly Cys Gly Ser Val Asn Arg Val Thr Ile Leu Cys Asp Lys Phe
        195                 200                 205

Ser Gly His Pro Lys Gly Phe Ala Tyr Ile Glu Phe Ser Asp Lys Glu
    210                 215                 220

Ser Val Arg Thr Ser Leu Ala Leu Asp Glu Ser Leu Phe Arg Gly Arg
225                 230                 235                 240

Gln Ile Lys Val Ile Pro Lys Arg Thr Asn Arg Pro Gly Ile Ser Thr
                245                 250                 255

Thr Asp Arg Gly Phe Pro Arg Ala Arg Tyr Arg Ala Arg Thr Thr Asn
            260                 265                 270

Tyr Asn Ser Ser Arg Ser Arg Phe Tyr Ser Gly Phe Asn Ser Arg Pro
        275                 280                 285

Arg Gly Arg Val Tyr Arg Gly Arg Ala Arg Ala Thr Ser Trp Tyr Ser
    290                 295                 300

Pro Tyr Asp Tyr Lys Asp Asp Asp Asp Lys

<210> SEQ ID NO 76
<211> LENGTH: 314
<212> TYPE: PRT
<213> ORGANISM: Artificial sequence
<220> FEATURE:
<223> OTHER INFORMATION: Human codon-optimized PABPN1 amino acid
      sequence (with FLAG-tag)

<400> SEQUENCE: 76

```
Met Ala Ala Ala Ala Ala Ala Ala Ala Gly Ala Ala Gly Gly
1               5                   10                  15

Arg Gly Ser Gly Pro Gly Arg Arg His Leu Val Pro Gly Ala Gly
            20                  25                  30

Gly Glu Ala Gly Glu Gly Ala Pro Gly Gly Ala Gly Asp Tyr Gly Asn
            35                  40                  45

Gly Leu Glu Ser Glu Glu Leu Glu Pro Glu Glu Leu Leu Glu Pro
        50                  55                  60

Glu Pro Glu Pro Glu Pro Glu Glu Pro Arg Pro Arg Ala Pro
65                  70                  75                  80

Pro Gly Ala Pro Gly Pro Gly Pro Ser Gly Ala Pro Gly Ser Gln
                85                  90                  95

Glu Glu Glu Glu Glu Pro Gly Leu Val Glu Gly Asp Pro Gly Asp Gly
            100                 105                 110

Ala Ile Glu Asp Pro Glu Leu Glu Ala Ile Lys Ala Arg Val Arg Glu
            115                 120                 125

Met Glu Glu Glu Ala Glu Lys Leu Lys Glu Leu Gln Asn Glu Val Glu
130                 135                 140

Lys Gln Met Asn Met Ser Pro Pro Gly Asn Ala Gly Pro Val Ile
145                 150                 155                 160

Met Ser Ile Glu Glu Lys Met Glu Ala Asp Ala Arg Ser Ile Tyr Val
                165                 170                 175

Gly Asn Val Asp Tyr Gly Ala Thr Ala Glu Glu Leu Glu Ala His Phe
            180                 185                 190

His Gly Cys Gly Ser Val Asn Arg Val Thr Ile Leu Cys Asp Lys Phe
        195                 200                 205

Ser Gly His Pro Lys Gly Phe Ala Tyr Ile Glu Phe Ser Asp Lys Glu
    210                 215                 220

Ser Val Arg Thr Ser Leu Ala Leu Asp Glu Ser Leu Phe Arg Gly Arg
225                 230                 235                 240

Gln Ile Lys Val Ile Pro Lys Arg Thr Asn Arg Pro Gly Ile Ser Thr
                245                 250                 255

Thr Asp Arg Gly Phe Pro Arg Ala Arg Tyr Arg Ala Arg Thr Thr Asn
            260                 265                 270

Tyr Asn Ser Ser Arg Ser Arg Phe Tyr Ser Gly Phe Asn Ser Arg Pro
        275                 280                 285

Arg Gly Arg Val Tyr Arg Gly Arg Ala Arg Ala Thr Ser Trp Tyr Ser
    290                 295                 300

Pro Tyr Asp Tyr Lys Asp Asp Asp Lys
305                 310
```

<210> SEQ ID NO 77
<211> LENGTH: 20
<212> TYPE: DNA
<213> ORGANISM: Artificial sequence
<220> FEATURE:

<223> OTHER INFORMATION: wtPABPN1-Fwd primer

<400> SEQUENCE: 77
atggtgcaac agcagaagag                                              20

<210> SEQ ID NO 78
<211> LENGTH: 20
<212> TYPE: DNA
<213> ORGANISM: Artificial sequence
<220> FEATURE:
<223> OTHER INFORMATION: wtPABPN1-Rev primer

<400> SEQUENCE: 78
ctttgggatg gccactaaat                                              20

<210> SEQ ID NO 79
<211> LENGTH: 23
<212> TYPE: DNA
<213> ORGANISM: Artificial sequence
<220> FEATURE:
<223> OTHER INFORMATION: wtPABPN1-Probe

<400> SEQUENCE: 79
cggttgactg aaccacagcc atg                                          23

<210> SEQ ID NO 80
<211> LENGTH: 19
<212> TYPE: DNA
<213> ORGANISM: Artificial sequence
<220> FEATURE:
<223> OTHER INFORMATION: optPABPN1-For primer

<400> SEQUENCE: 80
accgacagag gcttcccta                                               19

<210> SEQ ID NO 81
<211> LENGTH: 21
<212> TYPE: DNA
<213> ORGANISM: Artificial sequence
<220> FEATURE:
<223> OTHER INFORMATION: optPABPN1-Rev primer

<400> SEQUENCE: 81
ttctgctgct gttgtagttg g                                            21

<210> SEQ ID NO 82
<211> LENGTH: 23
<212> TYPE: DNA
<213> ORGANISM: Artificial sequence
<220> FEATURE:
<223> OTHER INFORMATION: optPABPN1-Probe

<400> SEQUENCE: 82
tggtccgggc tctgtaccta gcc                                          23

<210> SEQ ID NO 83
<211> LENGTH: 21
<212> TYPE: DNA
<213> ORGANISM: Artificial sequence
<220> FEATURE:
<223> OTHER INFORMATION: shmiR3-Fwd primer

<400> SEQUENCE: 83
ttcatctgct tctctacctc g                                            21

```
<210> SEQ ID NO 84
<211> LENGTH: 21
<212> TYPE: DNA
<213> ORGANISM: Artificial sequence
<220> FEATURE:
<223> OTHER INFORMATION: shmiR13-Fwd primer

<400> SEQUENCE: 84
aggggaatac catgatgtcg c                                          21

<210> SEQ ID NO 85
<211> LENGTH: 21
<212> TYPE: DNA
<213> ORGANISM: Artificial sequence
<220> FEATURE:
<223> OTHER INFORMATION: shmiR14-Fwd primer

<400> SEQUENCE: 85
ctcatattca tctgcttctc t                                          21

<210> SEQ ID NO 86
<211> LENGTH: 21
<212> TYPE: DNA
<213> ORGANISM: Artificial sequence
<220> FEATURE:
<223> OTHER INFORMATION: shmiR17-Fwd primer

<400> SEQUENCE: 86
attcatctgc ttctctacct c                                          21
```

REAGENTS FOR TREATMENT OF OCULOPHARYNGEAL MUSCULAR DYSTROPHY (OPMD) AND USE THEREOF

CROSS-REFERENCE TO RELATED APPLICATIONS

This application is a U.S. National Phase Application of international application number PCT/AU2017/051385, filed on Dec. 14, 2017, which claims the right of priority to U.S. Provisional No. 62/434,312, filed 14 Dec. 2016, the complete contents of which is incorporated by reference herein in its entirety.

SEQUENCE LISTING

The instant application contains a Sequence Listing which has been submitted via EFS-Web and is hereby incorporated by reference in its entirety. Said ASCII copy, created on Jun. 13, 2019, is named FBB-030_CRF_sequencelisting.txt, and is 39,903 bytes in size.

TECHNICAL FIELD

The present disclosure relates to RNA interference (RNAi) reagents for treatment of oculopharyngeal muscular dystrophy (OPMD), compositions comprising same, and use thereof to treat individuals suffering from OPMD or which are predisposed thereto.

BACKGROUND

OPMD is an autosomal dominant inherited, slow progressing, late-onset degenerative muscle disorder. The disease is mainly characterised by progressive eyelid drooping (ptosis) and swallowing difficulties (dysphagia). The pharyngeal and cricopharyngeal muscles are specific targets in OPMD. Proximal limb weakness tends to follow at a later stage of disease progression. The mutation that causes the disease is an abnormal expansion of a (GCN)n trinucleotide repeat in the coding region of the poly(A) binding protein nuclear 1 (PABPN1) gene. This expansion leads to an expanded polyalanine tract at the N-terminal of the PABPN1 protein: 10 alanines are present in the normal protein, expanded to 11 to 18 alanines in the mutant form (expPA-BPN1). The main pathological hallmark of the disease is nuclear aggregates of expPABPN1. A misfolding of expanded PABPN1 results in the accumulation of insoluble polymeric fibrillar aggregates inside nuclei of affected cells. PABPN1 is an aggregation prone protein and mutant alanine-expanded PABPN1 in OPMD has a higher aggregation rate than that of the wild type normal protein. However, it is still unclear whether the nuclear aggregates in OPMD have a pathological function or a protective role as a consequence of a cellular defence mechanism.

No treatment, pharmacological or otherwise, is presently available for OPMD, Symptomatic surgical interventions can partly correct ptosis and improve swallowing in moderate to severely affected individuals. For example, the cricopharyngeal myotomy is at present the only possible treatment available to improve swallowing in these patients. However, this does not correct the progressive degradation of the pharyngeal musculature, which often leads to death following swallowing difficulties and choking.

Accordingly, there remains a need for therapeutic agents to treat OPMD in patients suffering therefrom and/or who are predisposed thereto.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

SUMMARY

The present disclosure is based, in part, on the recognition by the inventors that no therapeutic agents currently exist for the treatment of OPMD. The present disclosure therefore provides RNAi reagents targeting regions of the PABPN1 mRNA transcript which is causative of OPMD. The inventors have shown that these RNAi reagents are effective for post-transcriptional suppression of PABPN1 mRNA transcripts, including transcript variants which would otherwise be translated into the mutant PABPN1 protein causative of OPMD i.e., those PABPN1 proteins comprising an expanded polyalanine tract. For example, it has been shown that exemplary RNAi reagents of the disclosure inhibit or reduce expression of PABPN1 protein in vitro. Furthermore, the present disclosure provides reagents for expression of wild-type human PABPN1 protein having a mRNA transcript which is not targeted by the RNAi reagents of the disclosure (hereinafter "PABPN1 replacement reagents"). The inventors have shown that when expressed in conjunction with the RNAi reagents of the disclosure, the PABPN1 replacement reagents are capable of producing a PABPN1 transcript which is resistant to the RNAi reagents and which is capable of being translated into functional PABPN1 protein. These findings by the inventors provide reagents which may have therapeutic applications in the treatment of OPMD.

Accordingly, the present disclosure provides a nucleic acid comprising a DNA sequence which encodes a short hairpin micro-RNA (shmiR), said shmiR comprising:
 an effector sequence of at least 17 nucleotides in length;
 an effector complement sequence;
 a stemloop sequence; and
 a primary micro RNA (pri-miRNA) backbone;
wherein the effector sequence is substantially complementary to a region of corresponding length in an RNA transcript set forth in any one of SEQ ID NOs: 1-13. Preferably, the effector sequence will be less than 30 nucleotides in length. For example, a suitable effector sequence may be in the range of 17-29 nucleotides in length. Preferably, the effector sequence will be 20 nucleotides in length. More preferably, the effector sequence will be 21 nucleotides in length and the effector complement sequence will be 20 nucleotides in length.

The effector sequence may comprise 4 base pair mismatches relative to a region of corresponding length in an RNA transcript set forth in any one of SEQ ID NOs: 1-13 to which the effector sequence is substantially complementary. In another example, the effector sequence comprises 3 base pair mismatches relative to a region of corresponding length in an RNA transcript set forth in any one of SEQ ID NOs: 1-13 to which the effector sequence is substantially complementary. In another example, the effector sequence comprises 2 base pair mismatches relative to a region of corresponding length in an RNA transcript set forth in any one of SEQ ID NOs: 1-13 to which the effector sequence is substantially complementary. In another example, the effector sequence comprises 1 base pair mismatch relative to a region of corresponding length in an RNA transcript set forth in any one of SEQ ID NOs: 1-13 to which the effector sequence is substantially complementary. In yet another example, the effector sequence is 100% complementary to a region of corresponding length in an RNA transcript set forth in any one of SEQ ID NOs: 1-13. Where mismatches are present, it is preferred that they are not located within the region corresponding to the seed region of the shmiR i.e., nucleotides 2-8 of the effector sequence.

Exemplary shmiRs comprising an effector sequence which is substantially complementary to a region of corresponding length in an RNA transcript set forth in SEQ ID NO: 1 are described herein (hereinafter referred to as "shmiR2").

Exemplary shmiRs comprising an effector sequence which is substantially complementary to a region of corresponding length in an RNA transcript set forth in SEQ ID NO: 2 are described herein (hereinafter referred to as "shmiR3").

Exemplary shmiRs comprising an effector sequence which is substantially complementary to a region of corresponding length in an RNA transcript set forth in SEQ ID NO: 3 are described herein (hereinafter referred to as "shmiR4").

Exemplary shmiRs comprising an effector sequence which is substantially complementary to a region of corresponding length in an RNA transcript set forth in SEQ ID NO: 4 are described herein (hereinafter referred to as "shmiR5").

Exemplary shmiRs comprising an effector sequence which is substantially complementary to a region of corresponding length in an RNA transcript set forth in SEQ ID NO: 5 are described herein (hereinafter referred to as "shmiR6").

Exemplary shmiRs comprising an effector sequence which is substantially complementary to a region of corresponding length in an RNA transcript set forth in SEQ ID NO: 6 are described herein (hereinafter referred to as "shmiR7").

Exemplary shmiRs comprising an effector sequence which is substantially complementary to a region of corresponding length in an RNA transcript set forth in SEQ ID NO: 7 are described herein (hereinafter referred to as "shmiR9").

Exemplary shmiRs comprising an effector sequence which is substantially complementary to a region of corresponding length in an RNA transcript set forth in SEQ ID NO: 8 are described herein (hereinafter referred to as "shmiR11").

Exemplary shmiRs comprising an effector sequence which is substantially complementary to a region of corresponding length in an RNA transcript set forth in SEQ ID NO: 9 are described herein (hereinafter referred to as "shmiR13").

Exemplary shmiRs comprising an effector sequence which is substantially complementary to a region of corresponding length in an RNA transcript set forth in SEQ ID NO: 10 are described herein (hereinafter referred to as "shmiR14").

Exemplary shmiRs comprising an effector sequence which is substantially complementary to a region of corresponding length in an RNA transcript set forth in SEQ ID NO: 11 are described herein (hereinafter referred to as "shmiR15").

Exemplary shmiRs comprising an effector sequence which is substantially complementary to a region of corresponding length in an RNA transcript set forth in SEQ ID NO: 12 are described herein (hereinafter referred to as "shmiR16").

Exemplary shmiRs comprising an effector sequence which is substantially complementary to a region of corresponding length in an RNA transcript set forth in SEQ ID NO: 13 are described herein (hereinafter referred to as "shmiR17").

In one example, the nucleic acid described herein may comprise a DNA sequence encoding a shmiR selected from the group consisting of:

a shmiR comprising: (i) an effector sequence which is substantially complementary to the sequence set forth in SEQ ID NO:14 with the exception of 1, 2, 3 or 4 base mismatches, provided that the effector sequence is capable of forming a duplex with a sequence set forth in SEQ ID NO: 14; and (ii) an effector complement sequence comprising a sequence which is substantially complementary to the effector sequence (shmiR2);

a shmiR comprising: (i) an effector sequence which is substantially complementary to the sequence set forth in SEQ ID NO:16 with the exception of 1, 2, 3 or 4 base mismatches, provided that the effector sequence is capable of forming a duplex with a sequence set forth in SEQ ID NO: 16; and (ii) an effector complement sequence comprising a sequence which is substantially complementary to the effector sequence (shmiR3);

a shmiR comprising: (i) an effector sequence which is substantially complementary to the sequence set forth in SEQ ID NO:18 with the exception of 1, 2, 3 or 4 base mismatches, provided that the effector sequence is capable of forming a duplex with a sequence set forth in SEQ ID NO:18; and (ii) an effector complement sequence comprising a sequence which is substantially complementary to the effector sequence (shmiR4);

a shmiR comprising: (i) an effector sequence which is substantially complementary to the sequence set forth in SEQ ID NO:20 with the exception of 1, 2, 3 or 4 base mismatches, provided that the effector sequence is capable of forming a duplex with a sequence set forth in SEQ ID NO:20; and (ii) an effector complement sequence comprising a sequence which is substantially complementary to the effector sequence (shmiR5);

a shmiR comprising: (i) an effector sequence which is substantially complementary to the sequence set forth in SEQ ID NO:22 with the exception of 1, 2, 3 or 4 base mismatches, provided that the effector sequence is capable of forming a duplex with a sequence set forth in SEQ ID NO:22; and (ii) an effector complement sequence comprising a sequence which is substantially complementary to the effector sequence (shmiR6);

a shmiR comprising: (i) an effector sequence which is substantially complementary to the sequence set forth in SEQ ID NO:24 with the exception of 1, 2, 3 or 4 base mismatches, provided that the effector sequence is capable of forming a duplex with a sequence set forth in SEQ ID NO:24; and (ii) an effector complement sequence comprising a sequence which is substantially complementary to the effector sequence (shmiR7);

a shmiR comprising: (i) an effector sequence which is substantially complementary to the sequence set forth in SEQ ID NO:26 with the exception of 1, 2, 3 or 4 base mismatches, provided that the effector sequence is capable of forming a duplex with a sequence set forth in SEQ ID NO:26; and (ii) an effector complement sequence comprising a sequence which is substantially complementary to the effector sequence (shmiR9);

a shmiR comprising: (i) an effector sequence which is substantially complementary to the sequence set forth in SEQ ID NO:28 with the exception of 1, 2, 3 or 4 base mismatches, provided that the effector sequence is capable of forming a duplex with a sequence set forth in SEQ ID NO:28; and (ii) an effector complement sequence comprising a sequence which is substantially complementary to the effector sequence (shmiR11);

a shmiR comprising: (i) an effector sequence which is substantially complementary to the sequence set forth in SEQ ID NO:30 with the exception of 1, 2, 3 or 4 base mismatches, provided that the effector sequence is capable of forming a duplex with a sequence set forth in SEQ ID NO:30; and (ii) an effector complement sequence comprising a sequence which is substantially complementary to the effector sequence (shmiR13);

a shmiR comprising: (i) an effector sequence which is substantially complementary to the sequence set forth in SEQ ID NO:32 with the exception of 1, 2, 3 or 4 base mismatches, provided that the effector sequence is capable of forming a duplex with a sequence set forth in SEQ ID NO:32; and (ii) an effector complement sequence comprising a sequence which is substantially complementary to the effector sequence (shmiR14);

a shmiR comprising: (i) an effector sequence which is substantially complementary to the sequence set forth in SEQ ID NO:34 with the exception of 1, 2, 3 or 4 base mismatches, provided that the effector sequence is capable of forming a duplex with a sequence set forth in SEQ ID NO:34; and (ii) an effector complement sequence comprising a sequence which is substantially complementary to the effector sequence (shmiR15);

a shmiR comprising: (i) an effector sequence which is substantially complementary to the sequence set forth in SEQ ID NO:36 with the exception of 1, 2, 3 or 4 base mismatches, provided that the effector sequence is capable of forming a duplex with a sequence set forth in SEQ ID NO:36; and (ii) an effector complement sequence comprising a sequence which is substantially complementary to the effector sequence (shmiR16); and a shmiR comprising: (i) an effector sequence which is substantially complementary to the sequence set forth in SEQ ID NO:38 with the exception of 1, 2, 3 or 4 base mismatches, provided that the effector sequence is capable of forming a duplex with a sequence set forth in SEQ ID NO:38; and (ii) an effector complement sequence comprising a sequence which is substantially complementary to the effector sequence (shmiR17).

In another example, the nucleic acid described herein may comprise a DNA sequence encoding a shmiR selected from the group consisting of:

a shmiR comprising an effector sequence set forth in SEQ ID NO:15 and an effector complement sequence which is substantially complementary to the sequence set forth in SEQ ID NO: 15 and capable of forming a duplex therewith (shmiR2);

a shmiR comprising an effector sequence set forth in SEQ ID NO:17 and an effector complement sequence which is substantially complementary to the sequence set forth in SEQ ID NO:17 and capable of forming a duplex therewith (shmiR3);

a shmiR comprising an effector sequence set forth in SEQ ID NO:19 and an effector complement sequence which is substantially complementary to the sequence set forth in SEQ ID NO: 19 and capable of forming a duplex therewith (shmiR4);

a shmiR comprising an effector sequence set forth in SEQ ID NO:21 and an effector complement sequence which is substantially complementary to the sequence set forth in SEQ ID NO:21 and capable of forming a duplex therewith (shmiR5);

a shmiR comprising an effector sequence set forth in SEQ ID NO:23 and an effector complement sequence which is substantially complementary to the sequence set forth in SEQ ID NO:23 and capable of forming a duplex therewith (shmiR6);

a shmiR comprising an effector sequence set forth in SEQ ID NO:25 and an effector complement sequence which is substantially complementary to the sequence set forth in SEQ ID NO:25 and capable of forming a duplex therewith (shmiR7);

a shmiR comprising an effector sequence set forth in SEQ ID NO:27 and an effector complement sequence which is substantially complementary to the sequence set forth in SEQ ID NO:27 and capable of forming a duplex therewith (shmiR9);

a shmiR comprising an effector sequence set forth in SEQ ID NO:29 and an effector complement sequence which is substantially complementary to the sequence set forth in SEQ ID NO:29 and capable of forming a duplex therewith (shmiR11);

a shmiR comprising an effector sequence set forth in SEQ ID NO:31 and an effector complement sequence which is substantially complementary to the sequence set forth in SEQ ID NO:31 and capable of forming a duplex therewith (shmiR13);

a shmiR comprising an effector sequence set forth in SEQ ID NO:33 and an effector complement sequence which is substantially complementary to the sequence set forth in SEQ ID NO:33 and capable of forming a duplex therewith (shmiR14);

a shmiR comprising an effector sequence set forth in SEQ ID NO:35 and an effector complement sequence which is substantially complementary to the sequence set forth in SEQ ID NO:35 and capable of forming a duplex therewith (shmiR15);

a shmiR comprising an effector sequence set forth in SEQ ID NO:37 and an effector complement sequence which is substantially complementary to the sequence set forth in SEQ ID NO:37 and capable of forming a duplex therewith (shmiR16); and a shmiR comprising an effector sequence set forth in SEQ ID NO:39 and an effector complement sequence which is substantially complementary to the sequence set forth in SEQ ID NO:39 and capable of forming a duplex therewith (shmiR17).

For example, the shmiR encoded by the nucleic acid described herein may comprise an effector complement sequence comprising 1, 2, 3 or 4 mismatches relative to the corresponding effector sequence, provided that the cognate effector and effector complement sequences are capable of forming a duplex region.

In another example, the nucleic acid described herein may comprise a DNA sequence encoding a shmiR selected from the group consisting of:

a shmiR comprising an effector sequence set forth in SEQ ID NO: 15 and an effector complement sequence set forth in SEQ ID NO: 14 (shmiR2);

a shmiR comprising an effector sequence set forth in SEQ ID NO: 17 and an effector complement sequence set forth in SEQ ID NO: 16 (shmiR3);

a shmiR comprising an effector sequence set forth in SEQ ID NO: 19 and an effector complement sequence set forth in SEQ ID NO: 18 (shmiR4);

a shmiR comprising an effector sequence set forth in SEQ ID NO: 21 and an effector complement sequence set forth in SEQ ID NO: 20 (shmiR5);

a shmiR comprising an effector sequence set forth in SEQ ID NO: 23 and an effector complement sequence set forth in SEQ ID NO: 22 (shmiR6);

a shmiR comprising an effector sequence set forth in SEQ ID NO: 25 and an effector complement sequence set forth in SEQ ID NO: 24 (shmiR7);

a shmiR comprising an effector sequence set forth in SEQ ID NO: 27 and an effector complement sequence set forth in SEQ ID NO: 26 (shmiR9);

a shmiR comprising an effector sequence set forth in SEQ ID NO: 29 and an effector complement sequence set forth in SEQ ID NO: 28 (shmiR11);

a shmiR comprising an effector sequence set forth in SEQ ID NO: 31 and an effector complement sequence set forth in SEQ ID NO: 30 (shmiR13);

a shmiR comprising an effector sequence set forth in SEQ ID NO: 33 and an effector complement sequence set forth in SEQ ID NO: 32 (shmiR14);

a shmiR comprising an effector sequence set forth in SEQ ID NO: 35 and an effector complement sequence set forth in SEQ ID NO: 34 (shmiR15);

a shmiR comprising an effector sequence set forth in SEQ ID NO: 37 and an effector complement sequence set forth in SEQ ID NO: 36 (shmiR16); and a shmiR comprising an effector sequence set forth in SEQ ID NO: 39 and an effector complement sequence set forth in SEQ ID NO: 38 (shmiR17).

The shmiR encoded by the nucleic acid of the disclosure may comprise, in a 5' to 3' direction:
 a 5' flanking sequence of the pri-miRNA backbone;
 the effector complement sequence;
 the stemloop sequence;
 the effector sequence; and
 a 3' flanking sequence of the pri-miRNA backbone.

The shmiR encoded by the nucleic acid of the disclosure may comprise, in a 5' to 3' direction:
 a 5' flanking sequence of the pri-miRNA backbone;
 the effector sequence;
 the stemloop sequence;
 the effector complement sequence; and
 a 3' flanking sequence of the pri-miRNA backbone.

Suitable loop sequences may be selected from those known in the art. However, an exemplary stemloop sequence is set forth in SEQ ID NO: 40.

Suitable primary micro RNA (pri-miRNA or pri-R) backbones for use in a nucleic acid of the disclosure may be selected from those known in the art. For example, the pri-miRNA backbone may be selected from a pri-miR-30a backbone, a pri-miR-155 backbone, a pri-miR-21 backbone and a pri-miR-136 backbone. Preferably, however, the pri-miRNA backbone is a pri-miR-30a backbone. In accordance with an example in which the pri-miRNA backbone is a pri-miR-30a backbone, the 5' flanking sequence of the pri-miRNA backbone is set forth in SEQ ID NO: 41 and the 3' flanking sequence of the pri-miRNA backbone is set forth in SEQ ID NO: 42.

In one example, the nucleic acid described herein comprises a DNA sequence selected from the sequence set forth in any one of SEQ ID NOs: 56-68. In accordance with this example, a shmiR encoded by the nucleic acid of the disclosure may comprise a sequence set forth in any one of SEQ ID NOs: 43-55.

It will be understood by a person of skill in the art that a nucleic acid in accordance with the present disclosure may be combined or used in conjunction with other therapeutic agents for treating OPMD e.g., such as other RNAi agents targeting RNA transcripts corresponding to a PABPN1 protein which is causative of OPMD. Accordingly, the present disclosure provides a nucleic acid comprising a DNA sequence encoding a shmiR as described herein in combination with one or more other RNAi agents for treating OPMD. In one example, a plurality of nucleic acids are provided comprising:

(a) at least one nucleic acid as described herein; and
(b) at least one further nucleic acid selected from:
 (i) a nucleic acid in accordance with the nucleic acids described herein; or
 (ii) a nucleic acid comprising a DNA sequence encoding a shmiR or short hairpin RNA (shRNA) comprising an effector sequence of at least 17 nucleotides in length and a effector complement sequence, wherein the effector sequence is substantially complementary to a RNA transcript corresponding to a PABPN1 protein which is causative of oculopharyngeal muscular dystrophy (OPMD);

wherein the shmiR encoded by the nucleic acid at (a) and the shmiR or shRNA encoded by the nucleic acid at (b) comprise different effector sequences.

In one example, the effector sequence of the shmiR or shRNA at (b)(ii) is substantially complementary to a region of corresponding length in an RNA transcript set forth in any one of SEQ ID NOs: 1-13. Preferably, the effector sequence of the shmiR or shRNA at (b)(ii) which is substantially complementary to a region of corresponding length in an RNA transcript set forth in any one of SEQ ID NOs: 1-13 will be less than 30 nucleotides in length. For example, a suitable effector sequence of the shmiR or shRNA may be in the range of 17-29 nucleotides in length.

In one example, at least one of the nucleic acids in the plurality comprises a DNA sequence encoding shmiR2 as described herein.

In one example, at least one of the nucleic acids in the plurality comprises a DNA sequence encoding shmiR3 as described herein.

In one example, at least one of the nucleic acids in the plurality comprises a DNA sequence encoding shmiR4 as described herein.

In one example, at least one of the nucleic acids in the plurality comprises a DNA sequence encoding shmiR5 as described herein.

In one example, at least one of the nucleic acids in the plurality comprises a DNA sequence encoding shmiR6 as described herein.

In one example, at least one of the nucleic acids in the plurality comprises a DNA sequence encoding shmiR7 as described herein.

In one example, at least one of the nucleic acids in the plurality comprises a DNA sequence encoding shmiR9 as described herein.

In one example, at least one of the nucleic acids in the plurality comprises a DNA sequence encoding shmiR11 as described herein.

In one example, at least one of the nucleic acids in the plurality comprises a DNA sequence encoding shmiR13 as described herein.

In one example, at least one of the nucleic acids in the plurality comprises a DNA sequence encoding shmiR14 as described herein.

In one example, at least one of the nucleic acids in the plurality comprises a DNA sequence encoding shmiR15 as described herein.

In one example, at least one of the nucleic acids in the plurality comprises a DNA sequence encoding shmiR16 as described herein.

In one example, at least one of the nucleic acids in the plurality comprises a DNA sequence encoding shmiR17 as described herein.

A plurality of nucleic acids in accordance with the present disclosure may comprise up to 10 nucleic acids, each encoding a shmiR as described herein i.e., shmiR2-7, shmiR9, shmiR11, and shmiR13-17, such as two nucleic acids or three nucleic acids or four nucleic acids or five nucleic acids or six nucleic acids or seven nucleic acids or eight nucleic acids or nine nucleic acids or ten nucleic acids. In one example, the plurality of nucleic acids comprises two nucleic acids of the disclosure, each encoding a shmiR as described herein. In another example, the plurality of nucleic acids comprises three nucleic acids of the disclosure, each encoding a shmiR as described herein. In one example, the plurality of nucleic acids comprises four nucleic acids of the disclosure, each encoding a shmiR as described herein. In one example, the plurality of nucleic acids comprises five nucleic acids of the disclosure, each encoding a shmiR as described herein. In one example, the plurality of nucleic acids comprises six nucleic acids of the disclosure, each encoding a shmiR as described herein. In one example, the plurality of nucleic acids comprises seven nucleic acids of the disclosure, each encoding a shmiR as described herein. In one example, the plurality of nucleic acids comprises eight nucleic acids of the disclosure, each encoding a shmiR as described herein. In one example, the plurality of nucleic acids comprises nine nucleic acids of the disclosure, each encoding a shmiR as described herein. In one example, the plurality of RNAs comprises ten nucleic acids of the disclosure, each encoding a shmiR as described herein. In accordance with any of the examples described herein, one or more of the nucleic acids in the plurality may encode a shRNA as described herein.

In one example, the plurality of nucleic acids of the disclosure comprises at least two nucleic acids, each comprising a DNA sequence encoding a shmiR selected from the group consisting of shmiR2, shmiR3, shmiR5, shmiR9, shmiR13, shmiR14 and shmiR17 as described herein.

One exemplary plurality of nucleic acids of the disclosure comprises one nucleic acid comprising a DNA sequence encoding shmiR13 as described herein and another nucleic acid comprising a DNA sequence encoding shmiR17 as described herein.

Another exemplary plurality of nucleic acids of the disclosure comprises one nucleic acid comprising a DNA sequence encoding shmiR3 as described herein and another nucleic acid comprising a DNA sequence encoding shmiR14 as described herein.

In accordance with an example in which a plurality of nucleic acids is provided, two or more of the nucleic acids may form separate parts of the same polynucleotide. In another example, two or more of the nucleic acids in the plurality form parts of different polynucleotides, respectively.

The or each nucleic acid in accordance with the present disclosure may comprise, or be in operable linkage with, one or more transcriptional terminator sequences. For example, the or each nucleic acid may comprise a transcriptional terminator sequence at the 3' terminus of the sequence encoding the shmiR. Such sequences will depend on the choice of promoter and will be known to a person of skill in the art. However, suitable choices of promoter and transcriptional terminator sequences for use in accordance with a nucleic acid of the disclosure or plurality thereof are described herein.

Alternatively, or in addition, the or each nucleic acid in accordance with the present disclosure may comprise, or be in operable linkage with, a transcription initiator sequence. For example, the or each nucleic acid may comprise a transcription initiator sequence at the 5' terminus of the sequence encoding the shmiR. Such sequences will be known to a person of skill in the art.

Alternatively, or in addition, the or each nucleic acid in accordance with the present disclosure may comprise one or more restriction sites e.g., to facilitate cloning of the nucleic acid(s) into cloning or expression vectors. For example, the nucleic acids described herein may include a restriction site upstream and/or downstream of the sequence encoding a shmiR of the disclosure. Suitable restriction enzyme recognition sequences will be known to a person of skill in the art.

A nucleic acid in accordance with the present disclosure, or a plurality of nucleic acids as described herein, may also be provided in the form of, or be comprised in, a DNA-directed RNA interference (ddRNAi) construct which is capable of expressing one or more shmiRs which is/are encoded by the nucleic acid(s) of the present disclosure.

In one example, the ddRNAi construct comprises at least two nucleic acids of the disclosure, such that the ddRNAi construct encodes at least two shmiRs targeting a RNA transcript corresponding to a PABPN1 protein which is causative of OPMD, each of which is different to one another.

In one example, each of the at least two nucleic acids in the ddRNAi construct encode a shmiR comprising an effector sequence which is substantially complementary to a region of corresponding length in an RNA transcript set forth in one of SEQ ID NOs: 1, 2, 4, 7, 9, 10 and 13. Thus, a ddRNAi construct in accordance with this example encodes two shmiRs selected from shmiR2, shmiR3, shmiR5, shmiR9, shmiR13, shmiR14 and shmiR17 as described herein.

One example of a ddRNAi construct of the disclosure comprises at least two nucleic acids selected from the group consisting of:

a nucleic acid comprising or consisting of a DNA sequence encoding a shmiR comprising an effector sequence set forth in SEQ ID NO: 15 and an effector complement sequence which is substantially complementary to SEQ ID NO: 15 and capable of forming a duplex therewith e.g., an effector complement sequence set forth in SEQ ID NO: 14 (shmiR2);

a nucleic acid comprising or consisting of a DNA sequence encoding a shmiR comprising an effector sequence set forth in SEQ ID NO: 17 and an effector complement sequence which is substantially complementary to SEQ ID NO: 17 and capable of forming a duplex therewith e.g., an effector complement sequence set forth in SEQ ID NO: 16 (shmiR3);

a nucleic acid comprising or consisting of a DNA sequence encoding a shmiR comprising an effector sequence set forth in SEQ ID NO: 21 and an effector complement sequence which is substantially complementary to SEQ ID NO: 21 and capable of forming a duplex therewith e.g., an effector complement sequence set forth in SEQ ID NO: 20 (shmiR5);

a nucleic acid comprising or consisting of a DNA sequence encoding a shmiR comprising an effector sequence set forth in SEQ ID NO: 27 and an effector complement sequence which is substantially complementary to SEQ ID NO: 27 and capable of forming a duplex therewith e.g., an effector complement sequence set forth in SEQ ID NO: 26 (shmiR9);

a nucleic acid comprising or consisting of a DNA sequence encoding a shmiR comprising an effector sequence set forth in SEQ ID NO: 31 and an effector complement sequence which is substantially complementary to SEQ ID NO: 31 and capable of forming a duplex therewith e.g., an effector complement sequence set forth in SEQ ID NO: 30 (shmiR13);

a nucleic acid comprising or consisting of a DNA sequence encoding a shmiR comprising an effector sequence set forth in SEQ ID NO: 33 and an effector complement sequence which is substantially complementary to SEQ ID NO: 33 and capable of forming a duplex therewith e.g., an effector complement sequence set forth in SEQ ID NO: 32 (shmiR14); and a nucleic acid comprising or consisting of a DNA sequence encoding a shmiR comprising an effector sequence set forth in SEQ ID NO: 39 and an effector complement sequence which is substantially complementary to SEQ ID NO: 39 and capable of forming a duplex therewith e.g., an effector complement sequence set forth in SEQ ID NO: 38 (shmiR17).

In one example, the ddRNAi construct comprises at least two nucleic acids selected from the group consisting of:

a nucleic acid comprising or consisting of a DNA sequence set forth in SEQ ID NO: 56 (shmiR2);

a nucleic acid comprising or consisting of a DNA sequence set forth in SEQ ID NO: 57 (shmiR3);

a nucleic acid comprising or consisting of a DNA sequence set forth in SEQ ID NO: 59 (shmiR5);

a nucleic acid comprising or consisting of a DNA sequence set forth in SEQ ID NO: 62 (shmiR9);

a nucleic acid comprising or consisting of a DNA sequence set forth in SEQ ID NO: 64 (shmiR13);

a nucleic acid comprising or consisting of a DNA sequence set forth in SEQ ID NO: 65 (shmiR14); and a nucleic acid comprising or consisting of a DNA sequence set forth in SEQ ID NO: 68 (shmiR17).

In one example, each of the at least two nucleic acids in the ddRNAi construct encode a shmiR comprising an effector sequence which is substantially complementary to a region of corresponding length in an RNA transcript set forth in one of SEQ ID NOs: 2, 9, 10 and 13. Thus, a ddRNAi construct in accordance with this example encodes two shmiRs selected from shmiR3, shmiR13, shmiR14 and shmiR17 as described herein.

One example of a ddRNAi construct of the disclosure comprises at least two nucleic acids selected from the group consisting of:

a nucleic acid comprising or consisting of a DNA sequence encoding a shmiR comprising an effector sequence set forth in SEQ ID NO: 17 and an effector complement sequence which is substantially complementary to SEQ ID NO: 17 and capable of forming a duplex therewith e.g., an effector complement sequence set forth in SEQ ID NO: 16 (shmiR3);

a nucleic acid comprising or consisting of a DNA sequence encoding a shmiR comprising an effector sequence set forth in SEQ ID NO: 31 and an effector complement sequence which is substantially complementary to SEQ ID NO: 31 and capable of forming a duplex therewith e.g., an effector complement sequence set forth in SEQ ID NO: 30 (shmiR13);

a nucleic acid comprising or consisting of a DNA sequence encoding a shmiR comprising an effector sequence set forth in SEQ ID NO: 33 and an effector complement sequence which is substantially complementary to SEQ ID NO: 33 and capable of forming a duplex therewith e.g., an effector complement sequence set forth in SEQ ID NO: 32 (shmiR14); and a nucleic acid comprising or consisting of a DNA sequence encoding a shmiR comprising an effector sequence set forth in SEQ ID NO: 39 and an effector complement sequence which is substantially complementary to SEQ ID NO: 39 and capable of forming a duplex therewith e.g., an effector complement sequence set forth in SEQ ID NO: 38 (shmiR17).

In one example, the ddRNAi construct comprises at least two nucleic acids selected from the group consisting of:

a nucleic acid comprising or consisting of a DNA sequence set forth in SEQ ID NO: 57 (shmiR3);

a nucleic acid comprising or consisting of a DNA sequence set forth in SEQ ID NO: 64 (shmiR13);

a nucleic acid comprising or consisting of a DNA sequence set forth in SEQ ID NO: 65 (shmiR14); and a nucleic acid comprising or consisting of a DNA sequence set forth in SEQ ID NO: 68 (shmiR17).

One exemplary ddRNAi construct of the disclosure comprises:

(a) a nucleic acid comprising or consisting of a DNA sequence encoding a shmiR comprising an effector sequence set forth in SEQ ID NO: 31 and an effector complement sequence set forth in SEQ ID NO: 30 (shmiR13); and (b) a nucleic acid comprising or consisting of a DNA sequence encoding a shmiR comprising an effector sequence set forth in SEQ ID NO: 39 and an effector complement sequence set forth in SEQ ID NO: 38 (shmiR17).

A ddRNAi construct in accordance with this example may comprise:

(a) a nucleic acid comprising or consisting of the DNA sequence set forth in SEQ ID NO: 64 (shmiR13); and (b) a nucleic acid comprising or consisting of the DNA sequence set forth in SEQ ID NO: 68 (shmiR17).

Another exemplary ddRNAi construct of the disclosure comprises:

(a) a nucleic acid comprising or consisting of a DNA sequence encoding a shmiR comprising an effector sequence set forth in SEQ ID NO: 17 and an effector complement sequence set forth in SEQ ID NO: 16 (shmiR3); and (b) a nucleic acid comprising or consisting of a DNA sequence encoding a shmiR comprising an effector sequence set forth in SEQ ID NO: 33 and an effector complement sequence set forth in SEQ ID NO: 32 (shmiR14).

A ddRNAi construct in accordance with this example may comprise:

(a) a nucleic acid comprising or consisting of the sequence set forth in SEQ ID NO:57 (shmiR3); and (b) a nucleic acid comprising or consisting of the sequence set forth in SEQ ID NO:65 (shmiR14).

In one example, a ddRNAi construct as described herein comprises a single promoter which is operably-linked to the or each nucleic acid encoding a shmiR of the disclosure. In another example, each nucleic acid encoding a shmiR of the disclosure is operably-linked to a separate promoter. For example, the promoter(s) is (are) positioned upstream of the respective nucleic acid(s) encoding the shmiR(s).

In accordance with an example in which the ddRNAi construct comprises multiple promoters, the promoters may be the same or different. Exemplary promoters which may be employed are muscle-specific promoters, such as for example, Spc512 and CK8. Other promoters which may be employed are RNA pol III promoters, such as for example, the U6 and H1 promoters. Exemplary U6 promoters are U6-1, U6-8 and U6-9 promoters.

A plurality of nucleic acids as described herein may also be provided in the form of, or be comprised in, a plurality of ddRNAi constructs, each capable of expressing one or more shmiRs which is/are encoded by the nucleic acid(s) of the present disclosure. For example, each nucleic acid in the plurality of nucleic acids may be provided in the form of, or be comprised in, a separate ddRNAi construct.

In one example, the plurality of ddRNAi constructs comprises at least two ddRNAi constructs, each comprising a nucleic acid of the plurality of nucleic acids described herein, such that collectively, the ddRNAi constructs encode at least two shmiRs targeting a RNA transcript corresponding to a PABPN1 protein which is causative of OPMD, each of which is different to one another.

In one example, each of the at least two ddRNAi constructs encodes a shmiR comprising an effector sequence which is substantially complementary to a region of corresponding length in an RNA transcript set forth in one of SEQ ID NOs: 1, 2, 4, 7, 9, 10 and 13. Thus, a plurality of ddRNAi constructs in accordance with this example collectively encode two shmiRs selected from shmiR2, shmiR3, shmiR5, shmiR9, shmiR13, shmiR14 and shmiR17 as described herein.

One example of a plurality of ddRNAi constructs of the disclosure comprises at least two ddRNAi constructs selected from the group consisting of:

a ddRNAi construct comprising a nucleic acid comprising or consisting of a DNA sequence encoding a shmiR comprising an effector sequence set forth in SEQ ID NO: 15 and an effector complement sequence which is substantially complementary to SEQ ID NO: 15 and capable of forming a duplex therewith e.g., an effector complement sequence set forth in SEQ ID NO: 14 (shmiR2);

a ddRNAi construct comprising a nucleic acid comprising or consisting of a DNA sequence encoding a shmiR comprising an effector sequence set forth in SEQ ID NO: 17 and an effector complement sequence which is substantially complementary to SEQ ID NO: 17 and capable of forming a duplex therewith e.g., an effector complement sequence set forth in SEQ ID NO: 16 (shmiR3);

a ddRNAi construct comprising a nucleic acid comprising or consisting of a DNA sequence encoding a shmiR comprising an effector sequence set forth in SEQ ID NO: 21 and an effector complement sequence which is substantially complementary to SEQ ID NO: 21 and capable of forming a duplex therewith e.g., an effector complement sequence set forth in SEQ ID NO: 20 (shmiR5);

a ddRNAi construct comprising a nucleic acid comprising or consisting of a DNA sequence encoding a shmiR comprising an effector sequence set forth in SEQ ID NO: 27 and an effector complement sequence which is substantially complementary to SEQ ID NO: 27 and capable of forming a duplex therewith e.g., an effector complement sequence set forth in SEQ ID NO: 26 (shmiR9);

a ddRNAi construct comprising a nucleic acid comprising or consisting of a DNA sequence encoding a shmiR comprising an effector sequence set forth in SEQ ID NO: 31 and an effector complement sequence which is substantially complementary to SEQ ID NO: 31 and capable of forming a duplex therewith e.g., an effector complement sequence set forth in SEQ ID NO: 30 (shmiR13);

a ddRNAi construct comprising a nucleic acid comprising or consisting of a DNA sequence encoding a shmiR comprising an effector sequence set forth in SEQ ID NO: 33 and an effector complement sequence which is substantially complementary to SEQ ID NO: 33 and capable of forming a duplex therewith e.g., an effector complement sequence set forth in SEQ ID NO: 32 (shmiR14); and a ddRNAi construct comprising a nucleic acid comprising or consisting of a DNA sequence encoding a shmiR comprising an effector sequence set forth in SEQ ID NO: 39 and an effector complement sequence which is substantially complementary to SEQ ID NO: 39 and capable of forming a duplex therewith e.g., an effector complement sequence set forth in SEQ ID NO: 38 (shmiR17).

In one example, the plurality of ddRNAi constructs comprises at least ddRNAi constructs selected from the group consisting of:

a ddRNAi construct comprising a nucleic acid comprising or consisting of a DNA sequence set forth in SEQ ID NO: 56 (shmiR2);

a ddRNAi construct comprising a nucleic acid comprising or consisting of a DNA sequence set forth in SEQ ID NO: 57 (shmiR3);

a ddRNAi construct comprising a nucleic acid comprising or consisting of a DNA sequence set forth in SEQ ID NO: 59 (shmiR5);

a ddRNAi construct comprising a nucleic acid comprising or consisting of a DNA sequence set forth in SEQ ID NO: 62 (shmiR9);

a ddRNAi construct comprising a nucleic acid comprising or consisting of a DNA sequence set forth in SEQ ID NO: 64 (shmiR13);

a ddRNAi construct comprising a nucleic acid comprising or consisting of a DNA sequence set forth in SEQ ID NO: 65 (shmiR14); and a ddRNAi construct comprising a nucleic acid comprising or consisting of a DNA sequence set forth in SEQ ID NO: 68 (shmiR17).

In one example, each of the at least two ddRNAi constructs encodes a shmiR comprising an effector sequence which is substantially complementary to a region of corresponding length in an RNA transcript set forth in one of SEQ ID NOs: 2, 9, 10 and 13. Thus, a plurality of ddRNAi constructs in accordance with this example collectively encodes two shmiRs selected from shmiR3, shmiR13, shmiR14 and shmiR17 as described herein.

One example of a plurality of ddRNAi constructs of the disclosure comprises at least two ddRNAi constructs selected from the group consisting of:

a ddRNAi construct comprising a nucleic acid comprising or consisting of a DNA sequence encoding a shmiR comprising an effector sequence set forth in SEQ ID NO: 17 and an effector complement sequence which is substantially complementary to SEQ ID NO: 17 and capable of forming a duplex therewith e.g., an effector complement sequence set forth in SEQ ID NO: 16 (shmiR3);

a ddRNAi construct comprising a nucleic acid comprising or consisting of a DNA sequence encoding a shmiR comprising an effector sequence set forth in SEQ ID NO: 31 and an effector complement sequence which is substantially complementary to SEQ ID NO: 31 and capable of forming a duplex therewith e.g., an effector complement sequence set forth in SEQ ID NO: 30 (shmiR13);

a ddRNAi construct comprising a nucleic acid comprising or consisting of a DNA sequence encoding a shmiR comprising an effector sequence set forth in SEQ ID NO: 33 and an effector complement sequence which is substantially complementary to SEQ ID NO: 33 and capable of forming a duplex therewith e.g., an effector complement sequence set forth in SEQ ID NO: 32 (shmiR14); and a ddRNAi construct comprising a nucleic acid comprising or consisting of a DNA sequence encoding a shmiR comprising an effector sequence set forth in SEQ ID NO: 39 and an effector complement sequence which is substantially complementary to SEQ ID NO: 39 and capable of forming a duplex therewith e.g., an effector complement sequence set forth in SEQ ID NO: 38 (shmiR17).

In one example, the at least two ddRNAi constructs is selected from the group consisting of:

a ddRNAi construct comprising a nucleic acid comprising or consisting of a DNA sequence set forth in SEQ ID NO: 57 (shmiR3);

a ddRNAi construct comprising a nucleic acid comprising or consisting of a DNA sequence set forth in SEQ ID NO: 64 (shmiR13);

a ddRNAi construct comprising a nucleic acid comprising or consisting of a DNA sequence set forth in SEQ ID NO: 65 (shmiR14); and a ddRNAi construct comprising a nucleic acid comprising or consisting of a DNA sequence set forth in SEQ ID NO: 68 (shmiR17).

One exemplary plurality of ddRNAi constructs of the disclosure comprises:

(a) a ddRNAi construct comprising a nucleic acid comprising or consisting of a DNA sequence encoding a shmiR comprising an effector sequence set forth in SEQ ID NO: 31 and an effector complement sequence set forth in SEQ ID NO: 30 (shmiR13); and (b) a ddRNAi construct comprising a nucleic acid comprising or consisting of a DNA sequence encoding a shmiR comprising an effector sequence set forth in SEQ ID NO: 39 and an effector complement sequence set forth in SEQ ID NO: 38 (shmiR17).

A plurality of ddRNAi constructs in accordance with this example may comprise:

(a) a ddRNAi construct comprising a nucleic acid comprising or consisting of the DNA sequence set forth in SEQ ID NO: 64 (shmiR13); and (b) a ddRNAi construct comprising a nucleic acid comprising or consisting of the DNA sequence set forth in SEQ ID NO: 68 (shmiR17).

Another exemplary plurality of ddRNAi constructs of the disclosure comprises:

(a) a ddRNAi construct comprising a nucleic acid comprising or consisting of a DNA sequence encoding a shmiR comprising an effector sequence set forth in SEQ ID NO: 17 and an effector complement sequence set forth in SEQ ID NO: 16 (shmiR3); and (b) a ddRNAi construct comprising a nucleic acid comprising or consisting of a DNA sequence encoding a shmiR comprising an effector sequence set forth in SEQ ID NO: 33 and an effector complement sequence set forth in SEQ ID NO: 32 (shmiR14).

A plurality of ddRNAi constructs in accordance with this example may comprise:

(a) a ddRNAi construct comprising a nucleic acid comprising or consisting of the sequence set forth in SEQ ID NO:57 (shmiR3); and (b) a ddRNAi construct comprising a nucleic acid comprising or consisting of the sequence set forth in SEQ ID NO:65 (shmiR14).

Each ddRNAi construct in the plurality of ddRNAi constructs as described herein comprises a single promoter which is operably-linked to the or each nucleic acid encoding a shmiR comprised therein. Where a ddRNAi construct in the plurality of ddRNAi constructs comprises more than one nucleic acid encoding a shmiR, each nucleic acid may be operably linked to the same promoter or be operably-linked to a separate promoter. In each of the foregoing examples describing a plurality of ddRNAi constructs, the promoter(s) is(are) positioned upstream of the respective nucleic acid(s) encoding the shmiR(s).

Exemplary promoters which may be employed are muscle-specific promoters, such as for example, Spc512 and CK8. Other promoters which may be employed are RNA pol III promoters, such as for example, the U6 and H1 promoters. Exemplary U6 promoters are U6-1, U6-8 and U6-9 promoters. The promoters comprised in the respective ddRNAi constructs of the plurality of ddRNAi constructs may be the same or different.

The present disclosure also provides a DNA construct comprising:

(a) a ddRNAi construct as described herein; and (b) a PABPN1 construct comprising a DNA sequence encoding a functional PABPN1 protein having a mRNA transcript which is not targeted by the shmiR(s) encoded by the ddRNAi construct. Preferably, the DNA sequence encoding the functional PABPN1 protein is codon optimised such that its mRNA transcript is not targeted by the shmiRs of the ddRNAi construct. In one example, functional PABPN1 protein is a wild-type human PABPN1 protein e.g., having a sequence set forth in SEQ ID NO: 74. In one example a codon optimised DNA sequence encoding the functional PABPN1 protein is set forth in SEQ ID NO: 73.

The DNA construct may comprise one or more promoters. Exemplary promoters for use in the DNA constructs of the disclosure are muscle-specific promoter, such as for example, Spc512 and CK8.

According to one example, the DNA construct comprises a promoter which is operably-linked to the PABPN1 construct and the ddRNAi construct, wherein the promoter is positioned upstream of the PABPN1 construct and the ddRNAi construct.

In one example, the DNA construct comprises, in a 5' to 3' direction:

(a) a muscle-specific promoter e.g., Spc512;

(b) a PABPN1 construct as described herein comprising a DNA sequence encoding a functional PABPN1 protein having a mRNA transcript which is not targeted by the shmiRs encoded by the ddRNAi construct; and (c) a ddRNAi construct of the disclosure comprising a nucleic acid comprising a DNA sequence encoding shmiR13 as described herein and a nucleic acid comprising a DNA sequence encoding shmiR17 as described herein.

In another example, the DNA construct comprises:

(a) a muscle-specific promoter e.g., Spc512;

(b) a PABPN1 construct as described herein comprising a DNA sequence encoding a functional PABPN1 protein having a mRNA transcript which is not targeted by the shmiRs encoded by the ddRNAi construct; and (c) a ddRNAi construct of the disclosure comprising a nucleic acid comprising a DNA sequence encoding shmiR3 as described herein and a nucleic acid comprising a DNA sequence encoding shmiR14 as described herein.

In another example, the PABPN1 construct and the ddRNAi construct are each operably-linked to separate promoters within the DNA construct. For example, the promoter which is in operable linkage with the PABPN1 construct will be operably linked to the DNA sequence encoding a functional PABPN1 protein comprised therein. The or each promoter which is in operable linkage with the ddRNAi construct will be operably-linked with one or more nucleic acids encoding a shmiR of the disclosure comprised in the ddRNAi construct. Exemplary promoters for use in the DNA constructs of the disclosure are muscle-specific promoter, such as for example, Spc512 and CK8.

One DNA construct in accordance with this example comprises, in a 5' to 3' direction:
(a) a muscle-specific promoter e.g., CK8 promoter, positioned upstream of a ddRNAi construct of the disclosure comprising a nucleic acid comprising a DNA sequence encoding shmiR13 as described herein and a nucleic acid comprising a DNA sequence encoding shmiR17 as described herein; and
(b) a muscle-specific promoter e.g., Spc512 promoter, positioned upstream of a PABPN1 construct as described herein comprising a DNA sequence encoding a functional PABPN1 protein having a mRNA transcript which is not targeted by the shmiRs encoded by the ddRNAi construct.

Another DNA construct in accordance with this example comprises, in a 5' to 3' direction:
(a) a muscle-specific promoter e.g., CK8 promoter, positioned upstream of a ddRNAi construct of the disclosure comprising a nucleic acid comprising a DNA sequence encoding shmiR3 as described herein and a nucleic acid comprising a DNA sequence encoding shmiR14 as described herein; and
(b) a muscle-specific promoter e.g., Spc512 promoter, positioned upstream of a PABPN1 construct as described herein comprising a DNA sequence encoding a functional PABPN1 protein having a mRNA transcript which is not targeted by the shmiRs encoded by the ddRNAi construct.

An exemplary ddRNAi construct encoding shmiR13 and shmiR17 for inclusion in a DNA construct of the disclosure may comprise a nucleic acid comprising or consisting of a DNA sequence encoding a shmiR comprising an effector sequence set forth in SEQ ID NO: 31 and an effector complement sequence which is substantially complementary to the sequence set forth in SEQ ID NO: 31 e.g., an effector complement sequence set forth in SEQ ID NO: 30 (shmiR13), and a nucleic acid comprising or consisting of a DNA sequence encoding a shmiR comprising an effector sequence set forth in SEQ ID NO: 39 and an effector complement sequence which is substantially complementary to the sequence set forth in SEQ ID NO: 39 e.g., an effector complement sequence set forth in SEQ ID NO: 38 (shmiR17). For example, the ddRNAi construct in accordance with this example of the DNA construct may comprise a nucleic acid comprising or consisting of the DNA sequence set forth in SEQ ID NO: 64 (shmiR13), and a nucleic acid comprising or consisting of the DNA sequence set forth in SEQ ID NO: 68 (shmiR17).

An exemplary ddRNAi construct encoding shmiR3 and shmiR14 for inclusion in a DNA construct of the disclosure may comprise a nucleic acid comprising or consisting of a DNA sequence encoding a shmiR comprising an effector sequence set forth in SEQ ID NO: 17 and an effector complement sequence which is substantially complementary to the sequence set forth in SEQ ID NO: 17 e.g., an effector complement sequence set forth in SEQ ID NO: 16 (shmiR3), and a nucleic acid comprising or consisting of a DNA sequence encoding a shmiR comprising an effector sequence set forth in SEQ ID NO: 33 and an effector complement sequence which is substantially complementary to the sequence set forth in SEQ ID NO: 33 e.g., an effector complement sequence set forth in SEQ ID NO: 34 (shmiR14). For example, the ddRNAi construct in accordance with this example of the DNA construct may comprise a nucleic acid comprising or consisting of the DNA sequence set forth in SEQ ID NO: 57 (shmiR3), and a nucleic acid comprising or consisting of the DNA sequence set forth in SEQ ID NO: 65 (shmiR14).

The present disclosure also provides an expression vector, comprising a ddRNAi construct of the disclosure, or a plurality of ddRNAi constructs of the disclosure or a DNA construct of the disclosure.

The present disclosure also provides plurality of expression vectors each of which comprises a ddRNAi construct of the disclosure. For example, one or more of the plurality of expression vectors comprises a plurality of ddRNAi constructs as disclosed herein. In another example, each expression vector in the plurality of expression vectors comprises a plurality of ddRNAi constructs as disclosed herein. In a further example, each expression vector in the plurality of expression vectors comprises a single ddRNAi construct as described herein. In any of the foregoing ways in this paragraph, the plurality of expression vectors may collectively express a plurality of shmiRs in accordance with the present disclosure.

The present disclosure also provides plurality of expression vectors comprising:
(a) an expression vector comprising one or more ddRNAi constructs of the disclosure; and
(b) an expression vector comprising a PABPN1 construct comprising a DNA sequence encoding a functional PABPN1 protein having a mRNA transcript which is not targeted by the shmiR(s) encoded by the ddRNAi construct.

Preferably, the DNA sequence encoding the functional PABPN1 protein is codon optimised such that its mRNA transcript is not targeted by the shmiRs of the ddRNAi construct. In one example, functional PABPN1 protein is a wild-type human PABPN1 protein e.g., having a sequence set forth in SEQ ID NO: 74. In one example, a codon optimised DNA sequence encoding the functional PABPN1 protein is set forth in SEQ ID NO: 73.

In one example, the DNA sequence encoding the functional PABPN1 protein may be operably-linked to a promoter comprised within the PABPN1 construct and positioned upstream of the DNA sequence encoding the functional PABPN1 protein. In another example, the expression vector comprising the PABPN1 construct comprises a promoter upstream of the PABPN1 construct and in operable-linkage with the DNA sequence encoding the functional PABPN1 protein. Exemplary promoters for use in the expression vector(s) of the disclosure are muscle-specific promoter, such as for example, Spc512 and CK8.

In one example, the or each expression vector is a plasmid or a minicircle.

In one example, the plasmid or minicircle or expression vector or ddRNAi construct is complexed with a cationic DNA binding polymer e.g., polyethylenimine.

In another example, the or each expression vector is a viral vector. For example, the viral vector is selected from the group consisting of an adeno-associated viral (AAV) vector, a retroviral vector, an adenoviral vector (AdV) and a lentiviral (LV) vector.

The present disclosure also provides a composition comprising a ddRNAi construct and/or a plurality of ddRNAi constructs and/or expression vector and/or a plurality of expression vectors as described herein. In one example, the composition may also comprise one or more pharmaceutically acceptable carriers and/or diluents.

The present disclosure also provides a method of inhibiting expression of a PABPN1 protein which is causative of OPMD in a subject, said method comprising administering to the subject a nucleic acid, a plurality of nucleic acids, a ddRNAi construct, a plurality of ddRNAi constructs, a DNA construct, an expression vector, a plurality of expression vector, or a composition described herein.

The present disclosure also provides a method of treating OPMD in a subject suffering therefrom, the method comprising administering to the subject a nucleic acid, a plurality of nucleic acids, a ddRNAi construct, a plurality of ddRNAi constructs, a DNA construct, an expression vector, a plurality of expression vectors, or a composition described herein. The method may comprise administering the plurality of expression vectors to the subject together, simultaneously or consecutively.

The present disclosure also provides a kit comprising:
(a) one or more agents for inhibiting expression of a PABPN1 protein which is causative of OPMD, said agent(s) being selected from a nucleic acid, a plurality of nucleic acids, a ddRNAi construct, a plurality of ddRNAi constructs, a DNA construct, an expression vector, a plurality of expression vectors, or a composition described herein; and
(b) an expression vector comprising a DNA sequence encoding a functional PABPN1 protein having a mRNA transcript which is not targeted by shmiRs expressed by the agent at (a).

Preferably, the DNA sequence encoding the functional PABPN1 protein is codon optimised such that its mRNA transcript is not targeted by the shmiRs encoded by the agent at (a). In one example, functional PABPN1 protein is a wild-type human PABPN1 protein e.g., having a sequence set forth in SEQ ID NO: 74. In one example, the codon optimised DNA sequence encoding the functional PABPN1 protein is set forth in SEQ ID NO: 73.

The DNA sequence encoding the functional PABPN1 protein may be operably-linked to a promoter comprised within the expression vector at (b) and positioned upstream of the DNA sequence encoding the functional PABPN1 protein. An exemplary promoter for use in the expression vector at (b) is a muscle-specific promoter, such as for example, a Spc512 or CK8 promoter.

The present disclosure also provides a kit comprising the plurality of expression vectors described herein packaged as separate components.

The present disclosure also provides a kit comprising a nucleic acid, a plurality of nucleic acids, a ddRNAi construct, a plurality of ddRNAi constructs, a DNA construct, an expression vector, a plurality of expression vectors, or a composition described herein, packaged with instruction for use in a method of the disclosure.

In one example, the kit as described herein is for use in treating OPMD according to a method described herein.

The present disclosure also provides use of a nucleic acid, a plurality of nucleic acids, a ddRNAi construct, a plurality of ddRNAi constructs, a DNA construct, an expression vector, a plurality of expression vectors, and/or a composition described herein in the preparation of a medicament, e.g., for treating OPMD in a subject and/or in a method disclosed herein.

The present disclosure also provides nucleic acid, a plurality of nucleic acids, a ddRNAi construct, a plurality of ddRNAi constructs, a DNA construct, an expression vector, a plurality of expression vectors, and/or a composition described herein for use in therapy. For example, the nucleic acid, the plurality of nucleic acids, the ddRNAi construct, the plurality of ddRNAi constructs, the DNA construct, the expression vector, the plurality of expression vectors and/or the composition may be for use in treating OPMD in a subject suffering therefrom or predisposed thereto and/or in a method disclosed herein.

KEY TO THE SEQUENCE LISTING

Figure 1:
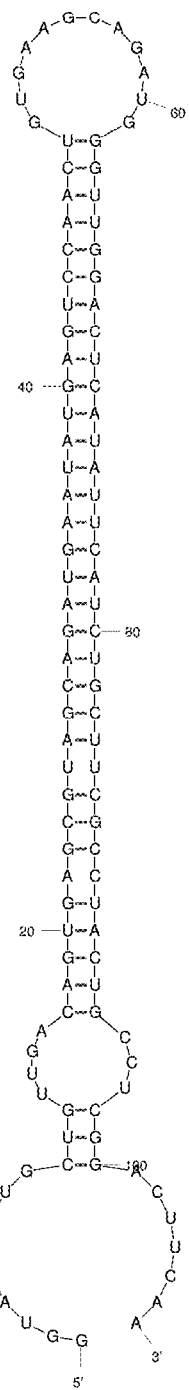
FIG. 1 illustrates the predicted secondary structure of a representative shmiR construct comprising a 5' flanking region, a siRNA sense strand; a stem/loop junction sequence, an siRNA anti-sense strand, and a 3' flanking region.

SEQ ID NO: 1: RNA sequence for region within mRNA transcript corresponding to PABPN1 protein designated PABPN1 mRNA Region 2.
SEQ ID NO: 2: RNA sequence for region within mRNA transcript corresponding to PABPN1 protein designated PABPN1 mRNA Region 3.
SEQ ID NO: 3: RNA sequence for region within mRNA transcript corresponding to PABPN1 protein designated PABPN1 mRNA Region 4.
SEQ ID NO: 4: RNA sequence for region within mRNA transcript corresponding to PABPN1 protein designated PABPN1 mRNA Region 5.
SEQ ID NO: 5: RNA sequence for region within mRNA transcript corresponding to PABPN1 protein designated PABPN1 mRNA Region 6.
SEQ ID NO: 6: RNA sequence for region within mRNA transcript corresponding to PABPN1 protein designated PABPN1 mRNA Region 7.
SEQ ID NO: 7: RNA sequence for region within mRNA transcript corresponding to PABPN1 protein designated PABPN1 mRNA Region 9.
SEQ ID NO: 8: RNA sequence for region within mRNA transcript corresponding to PABPN1 protein designated PABPN1 mRNA Region 11.
SEQ ID NO: 9: RNA sequence for region within mRNA transcript corresponding to PABPN1 protein designated PABPN1 mRNA Region 13.
SEQ ID NO: 10: RNA sequence for region within mRNA transcript corresponding to PABPN1 protein designated PABPN1 mRNA Region 14.
SEQ ID NO: 11: RNA sequence for region within mRNA transcript corresponding to PABPN1 protein designated PABPN1 mRNA Region 15.
SEQ ID NO: 12: RNA sequence for region within mRNA transcript corresponding to PABPN1 protein designated PABPN1 mRNA Region 16.
SEQ ID NO: 13: RNA sequence for region within mRNA transcript corresponding to PABPN1 protein designated PABPN1 mRNA Region 17.
SEQ ID NO: 14: RNA effector complement sequence for shmiR designated shmiR2.

SEQ ID NO: 15: RNA effector sequence for shmiR designated shmiR2.
SEQ ID NO: 16: RNA effector complement sequence for shmiR designated shmiR3.
SEQ ID NO: 17: RNA effector sequence for shmiR designated shmiR3.
SEQ ID NO: 18: RNA effector complement sequence for shmiR designated shmiR4.
SEQ ID NO: 19: RNA effector sequence for shmiR designated shmiR4.
SEQ ID NO: 20: RNA effector complement sequence for shmiR designated shmiR5.
SEQ ID NO: 21: RNA effector sequence for shmiR designated shmiR5.
SEQ ID NO: 22: RNA effector complement sequence for shmiR designated shmiR6.
SEQ ID NO: 23: RNA effector sequence for shmiR designated shmiR6.
SEQ ID NO: 24: RNA effector complement sequence for shmiR designated shmiR7.
SEQ ID NO: 25: RNA effector sequence for shmiR designated shmiR7.
SEQ ID NO: 26: RNA effector complement sequence for shmiR designated shmiR9.
SEQ ID NO: 27: RNA effector sequence for shmiR designated shmiR9.
SEQ ID NO: 28: RNA effector complement sequence for shmiR designated shmiR11.
SEQ ID NO: 29: RNA effector sequence for shmiR designated shmiR11.
SEQ ID NO: 30: RNA effector complement sequence for shmiR designated shmiR13.
SEQ ID NO: 31: RNA effector sequence for shmiR designated shmiR13.
SEQ ID NO: 32: RNA effector complement sequence for shmiR designated shmiR14.
SEQ ID NO: 33: RNA effector sequence for shmiR designated shmiR14.
SEQ ID NO: 34: RNA effector complement sequence for shmiR designated shmiR15.
SEQ ID NO: 35: RNA effector sequence for shmiR designated shmiR15.
SEQ ID NO: 36: RNA effector complement sequence for shmiR designated shmiR16.
SEQ ID NO: 37: RNA effector sequence for shmiR designated shmiR16.
SEQ ID NO: 38: RNA effector complement sequence for shmiR designated shmiR17.
SEQ ID NO: 39: RNA effector sequence for shmiR designated shmiR17.
SEQ ID NO: 40: RNA stem loop sequence for shmiRs
SEQ ID NO: 41: 5' flanking sequence of the pri-miRNA backbone.
SEQ ID NO: 42: 3' flanking sequence of the pri-miRNA backbone
SEQ ID NO: 43: RNA sequence for shmiR designated shmiR2.
SEQ ID NO: 44: RNA sequence for shmiR designated shmiR3.
SEQ ID NO: 45: RNA sequence for shmiR designated shmiR4.
SEQ ID NO: 46: RNA sequence for shmiR designated shmiR5.
SEQ ID NO: 47: RNA sequence for shmiR designated shmiR6.
SEQ ID NO: 48: RNA sequence for shmiR designated shmiR7.
SEQ ID NO: 49: RNA sequence for shmiR designated shmiR9.
SEQ ID NO: 50: RNA sequence for shmiR designated shmiR11.
SEQ ID NO: 51: RNA sequence for shmiR designated shmiR13.
SEQ ID NO: 52: RNA sequence for shmiR designated shmiR14.
SEQ ID NO: 53: RNA sequence for shmiR designated shmiR15.
SEQ ID NO: 54: RNA sequence for shmiR designated shmiR16.
SEQ ID NO: 55: RNA sequence for shmiR designated shmiR17.
SEQ ID NO: 56: DNA sequence coding for shmiR designated shmiR2.
SEQ ID NO: 57: DNA sequence coding for shmiR designated shmiR3.
SEQ ID NO: 58: DNA sequence coding for shmiR designated shmiR4.
SEQ ID NO: 59: DNA sequence coding for shmiR designated shmiR5.
SEQ ID NO: 60: DNA sequence coding for shmiR designated shmiR6.
SEQ ID NO: 61: DNA sequence coding for shmiR designated shmiR7.
SEQ ID NO: 62: DNA sequence coding for shmiR designated shmiR9.
SEQ ID NO: 63: DNA sequence coding for shmiR designated shmiR11.
SEQ ID NO: 64: DNA sequence coding for shmiR designated shmiR13.
SEQ ID NO: 65: DNA sequence coding for shmiR designated shmiR14.
SEQ ID NO: 66: DNA sequence coding for shmiR designated shmiR15.
SEQ ID NO: 67: DNA sequence coding for shmiR designated shmiR16.
SEQ ID NO: 68: DNA sequence coding for shmiR designated shmiR17.
SEQ ID NO: 69: DNA sequence for double construct version 1 coding for shmiR3 and shmiR14 under control of the muscle specific CK8 promoter and codon optimized PABPN1 under control of Spc512
SEQ ID NO: 70: DNA sequence for double construct version 1 coding for shmiR17 and shmiR13 under control of the muscle specific CK8 promoter and codon optimized PABPN1 under control of Spc512
SEQ ID NO: 71: DNA sequence for double construct version 2 coding for coPABPN1 and shmiRs designated shmiR3 and shmiR14, under control of Spc512.
SEQ ID NO: 72: DNA sequence for double construct version 2 coding for coPABPN1 and shmiRs designated shmiR17 and shmiR13 under control of Spc512.
SEQ ID NO: 73 DNA sequence for Human codon-optimized PABPN1 cDNA sequence.
SEQ ID NO: 74 Amino acid sequence for codon-optimised human PABPN1 protein.
SEQ ID NO: 75 Amino acid sequence for wildtype human PABPN1 protein with FLAG-tag.
SEQ ID NO: 76 Amino acid sequence for codon-optimised human PABPN1 protein with FLAG-tag.
SEQ ID NO: 77 DNA sequence for primer designated wtPABPN1-Fwd.
SEQ ID NO: 78 DNA sequence for primer designated wtPABPN1-Rev SEQ ID NO: 79 DNA sequence for probe designated wtPABPN1-Probe
SEQ ID NO: 80 DNA sequence for primer designated optPABPN1-Fwd
SEQ ID NO: 81 DNA sequence for primer designated optPABPN1-Rev
SEQ ID NO: 82 DNA sequence for probe designated opt-PABPN1-Probe
SEQ ID NO: 83 DNA sequence for primer designated shmiR3-FWD
SEQ ID NO: 84 DNA sequence for primer designated shmiR13-FWD
SEQ ID NO: 85 DNA sequence for primer designated shmiR14-FWD
SEQ ID NO: 86 DNA sequence for primer designated shmiR17-FWD

DETAILED DESCRIPTION

General

Throughout this specification, unless specifically stated otherwise or the context requires otherwise, reference to a single step, feature, composition of matter, group of steps or group of features or compositions of matter shall be taken to encompass one and a plurality (i.e. one or more) of those steps, features, compositions of matter, groups of steps or groups of features or compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the present disclosure.

Any example of the present disclosure herein shall be taken to apply mutatis mutandis to any other example of the disclosure unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant DNA, recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbor Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbor Laboratory, (1988), and J. E. Coligan et al. (editors) Current Protocols in Immunology, John Wiley & Sons (including all updates until present).

Throughout this specification, unless the context requires otherwise, the word "comprise", or variations such as "comprises" or "comprising", is understood to imply the inclusion of a stated step or element or integer or group of steps or elements or integers but not the exclusion of any other step or element or integer or group of elements or integers.

The term "and/or", e.g., "X and/or Y" shall be understood to mean either "X and Y" or "X or Y" and shall be taken to provide explicit support for both meanings or for either meaning.

Selected Definitions

By "RNA" is meant a molecule comprising at least one ribonucleotide residue. By "ribonucleotide" is meant a nucleotide with a hydroxyl group at the 2' position of a β-D-ribo-furanose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siNA or internally, for example at one or more nucleotides of the RNA. Nucleotides in the RNA molecules of the instant disclosure can also comprise non-standard nucleotides, such as non-naturally occurring nucleotides or chemically synthesized nucleotides or deoxynucleotides. These altered RNAs can be referred to as analogs or analogs of naturally-occurring RNA.

The term "RNA interference" or "RNAi" refers generally to RNA-dependent silencing of gene expression initiated by double stranded RNA (dsRNA) molecules in a cell's cytoplasm. The dsRNA molecule reduces or inhibits transcription products of a target nucleic acid sequence, thereby silencing the gene or reducing expression of that gene.

As used herein, the term "double stranded RNA" or "dsRNA" refers to a RNA molecule having a duplex structure and comprising an effector sequence and an effector complement sequence which are of similar length to one another. The effector sequence and the effector complement sequence can be in a single RNA strand or in separate RNA strands. The "effector sequence" (often referred to as a "guide strand") is substantially complementary to a target sequence, which in the present case, is a region of a PABPN1 mRNA transcript. The "effector sequence" can also be referred to as the "antisense sequence". The "effector complement sequence" will be of sufficient complementary to the effector sequence such that it can anneal to the effector sequence to form a duplex. In this regard, the effector complement sequence will be substantially homologous to a region of target sequence. As will be apparent to the skilled person, the term "effector complement sequence" can also be referred to as the "complement of the effector sequence" or the sense sequence.

As used herein, the term "duplex" refers to regions in two complementary or substantially complementary nucleic acids (e.g., RNAs), or in two complementary or substantially complementary regions of a single-stranded nucleic acid (e.g., RNA), that form base pairs with one another, either by Watson-Crick base pairing or any other manner that allows for a stabilized duplex between the nucleotide sequences that are complementary or substantially complementary. It will be understood by the skilled person that within a duplex region, 100% complementarity is not required; substantial complementarity is allowable. Substantial complementarity includes may include 79% or greater complementarity. For example, a single mismatch in a duplex region consisting of 19 base pairs (i.e., 18 base pairs and one mismatch) results in 94.7% complementarity, rendering the duplex region substantially complementary. In another example, two mismatches in a duplex region consisting of 19 base pairs (i.e., 17 base pairs and two mismatches) results in 89.5% complementarity, rendering the duplex region substantially complementary. In yet another example, three mismatches in a duplex region consisting of 19 base pairs (i.e., 16 base pairs and three mismatches) results in 84.2% complementarity, rendering the duplex region substantially complementary, and so on.

The dsRNA may be provided as a hairpin or stem loop structure, with a duplex region comprised of an effector sequence and effector complement sequence linked by at least 2 nucleotide sequence which is termed a stem loop. When a dsRNA is provided as a hairpin or stem loop structure it can be referred to as a "hairpin RNA" or "short hairpin RNAi agent" or "shRNA". Other dsRNA molecules provided in, or which give rise to, a hairpin or stem loop structure include primary miRNA transcripts (pri-miRNA) and precursor microRNA (pre-miRNA). Pre-miRNA shRNAs can be naturally produced from pri-miRNA by the action of the enzymes Drosha and Pasha which recognize and release regions of the primary miRNA transcript which form a stem-loop structure. Alternatively, the pri-miRNA transcript can be engineered to replace the natural stem-loop structure with an artificial/recombinant stem-loop structure. That is, an artificial/recombinant stem-loop structure may be inserted or cloned into a pri-miRNA backbone sequence which lacks its natural stem-loop structure. In the case of stemloop sequences engineered to be expressed as part of a pri-miRNA molecule, Drosha and Pasha recognize and release the artificial shRNA. dsRNA molecules produced using this approach are known as "shmiRNAs", "shmiRs" or "microRNA framework shRNAs".

As used herein, the term "complementary" with regard to a sequence refers to a complement of the sequence by Watson-Crick base pairing, whereby guanine (G) pairs with cytosine (C), and adenine (A) pairs with either uracil (U) or thymine (T). A sequence may be complementary to the entire length of another sequence, or it may be complementary to a specified portion or length of another sequence. One of skill in the art will recognize that U may be present in RNA, and that T may be present in DNA. Therefore, an A within either of a RNA or DNA sequence may pair with a U in a RNA sequence or T in a DNA sequence.

As used herein, the term "substantially complementary" is used to indicate a sufficient degree of complementarity or precise pairing such that stable and specific binding occurs between nucleic acid sequences e.g., between the effector sequence and the effector complement sequence or between the effector sequence and the target sequence. It is understood that the sequence of a nucleic acid need not be 100% complementary to that of its target or complement. The term encompasses a sequence complementary to another sequence with the exception of an overhang. In some cases, the sequence is complementary to the other sequence with the exception of 1-2 mismatches. In some cases, the sequences are complementary except for 1 mismatch. In some cases, the sequences are complementary except for 2 mismatches. In other cases, the sequences are complementary except for 3 mismatches. In yet other cases, the sequences are complementary except for 4 mismatches.

The term "encoded", as used in the context of a shRNA or shmiR of the disclosure, shall be understood to mean a shRNA or shmiR which is capable of being transcribed from a DNA template. Accordingly, a nucleic acid that encodes, or codes for, a shRNA or shmiR of the disclosure will comprise a DNA sequence which serves as a template for transcription of the respective shRNA or shmiR.

The term "DNA-directed RNAi construct" or "ddRNAi construct" refers to a nucleic acid comprising DNA sequence which, when transcribed produces a shRNA or shmiR molecule (preferably a shmiR) which elicits RNAi. The ddRNAi construct may comprise a nucleic acid which is transcribed as a single RNA that is capable of self-annealing into a hairpin structure with a duplex region linked by a stem loop of at least 2 nucleotides i.e., shRNA or shmiR, or as a single RNA with multiple shRNAs or shmiRs, or as multiple RNA transcripts each capable of folding as a single shRNA or shmiR respectively. The ddRNAi construct may be provided within a larger "DNA construct" comprising one or more additional DNA sequences. For example, the ddRNAi construct may be provided in a DNA construct comprising a further DNA sequence coding for functional PABPN1 protein which has been codon optimised such that its mRNA transcript is not targeted by shmiRs of the ddRNAi construct. The ddRNAi construct and/or the DNA construct comprising same may be within an expression vector e.g., operably linked to a promoter.

As used herein, the term "operably-linked" or "operable linkage" (or similar) means that a coding nucleic acid sequence is linked to, or in association with, a regulatory sequence, e.g., a promoter, in a manner which facilitates expression of the coding sequence. Regulatory sequences include promoters, enhancers, and other expression control elements that are art-recognized and are selected to direct expression of the coding sequence.

A "vector" will be understood to mean a vehicle for introducing a nucleic acid into a cell. Vectors include, but are not limited to, plasmids, phagemids, viruses, bacteria, and vehicles derived from viral or bacterial sources. A "plasmid" is a circular, double-stranded DNA molecule. A useful type of vector for use in accordance with the present disclosure is a viral vector, wherein heterologous DNA sequences are inserted into a viral genome that can be modified to delete one or more viral genes or parts thereof. Certain vectors are capable of autonomous replication in a host cell (e.g., vectors having an origin of replication that functions in the host cell). Other vectors can be stably integrated into the genome of a host cell, and are thereby replicated along with the host genome. As used herein, the term "expression vector" will be understood to mean a vector capable of expressing a RNA molecule of the disclosure.

A "functional PABPN1 protein" shall be understood to mean a PABPN1 protein having the functional properties of a wild-type PABPN1 protein e.g., an ability to control site of mRNA polyadenylation and/or intron splicing in a mammalian cell. Accordingly, a "functional PABPN1 protein" will be understood to be a PABPN1 protein which is not causative of OPMD when expressed or present in a subject. In one example, a reference herein to "functional PABPN1 protein" is a reference to human wild-type PABPN1 protein. The sequence of human wild-type PABPN1 protein is set forth in NCBI RefSeq NP_004634. Accordingly, a functional human PABPN1 protein may have the functional properties in vivo of the human PABPN1 protein set forth in NCBI RefSeq NP_004634.

As used herein, the terms "treating", "treat" or "treatment" and variations thereof, refer to clinical intervention designed to alter the natural course of the individual or cell being treated during the course of clinical pathology. Desirable effects of treatment include decreasing the rate of disease progression, ameliorating or palliating the disease state, and remission or improved prognosis. It follows that treatment of OPMD includes reducing or inhibiting expression of a PABPN1 protein which is causative of OPMD in the subject and/or expressing in the subject a PABPN1 protein having the normal length of polyalanine residues. Preferably, treatment of OPMD includes reducing or inhibiting expression of the PABPN1 protein which is causative of OPMD in the subject and expressing in the subject a PABPN1 protein having the normal length of polyalanine residues. An individual is successfully "treated", for example, if one or more of the above treatment outcomes is achieved.

A "therapeutically effective amount" is at least the minimum concentration or amount required to effect a measurable improvement in the OPMD condition, such as a measurable improvement in one or more symptoms of OPMD e.g., including but not limited to ptosis, dysphagia and muscle weakness in the subject. A therapeutically effective amount herein may vary according to factors such as the disease state, age, sex, and weight of the patient, and the ability of the shmiR, nucleic acid encoding same, ddRNAi construct, DNA construct, expression vector, or composition comprising same, to elicit a desired response in the individual and/or the ability of the expression vector to express functional PABPN1 protein in the subject. A therapeutically effective amount is also one in which any toxic or detrimental effects of the shmiR, nucleic acid encoding same, ddRNAi construct, DNA construct, expression vector, or composition comprising same, are outweighed by the therapeutically beneficial effects of the shmiR, nucleic acid encoding same, ddRNAi construct, DNA construct, expression vector, or composition comprising same, to inhibit, suppress or reduce expression of PABPN1 protein causative of OPMD considered alone or in combination with the therapeutically beneficial effects of the expression of functional PABPN1 protein in the subject.

As used herein, the "subject" or "patient" can be a human or non-human animal suffering from or genetically predisposed to OPMD i.e., possess a PABPN1 gene variant which is causative of OPMD. The "non-human animal" may be a primate, livestock (e.g. sheep, horses, cattle, pigs, donkeys), companion animal (e.g. pets such as dogs and cats), laboratory test animal (e.g. mice, rabbits, rats, guinea pigs, drosophila, *C. elegans*, zebrafish), performance animal (e.g. racehorses, camels, greyhounds) or captive wild animal. In one example, the subject or patient is a mammal. In one example, the subject or patient is a human.

The terms "reduced expression", "reduction in expression" or similar, refer to the absence or an observable decrease in the level of protein and/or mRNA product from the target gene e.g., the PABPN1 gene. The decrease does not have to be absolute, but may be a partial decrease sufficient for there to a detectable or observable change as a result of the RNAi effected by the shmiR, nucleic acid encoding same, ddRNAi construct, DNA construct, expression vector, or composition comprising same of the disclosure. The decrease can be measured by determining a decrease in the level of mRNA and/or protein product from a target nucleic acid relative to a cell lacking the shmiR, nucleic acid encoding same, ddRNAi construct, DNA construct, expression vector, or composition comprising same, and may be as little as 1%, 5% or 10%, or may be absolute i.e., 100% inhibition. The effects of the decrease may be determined by examination of the outward properties i.e., quantitative and/or qualitative phenotype of the cell or organism, and may also include detection of the presence or a change in the amount of nuclear aggregates of expPABPN1 in the cell or organism following administration of a shmiR, nucleic acid encoding same, ddRNAi construct, DNA construct, expression vector, or composition comprising same, of the disclosure.

Agents for RNAi

In one example, the present disclosure provides a nucleic acid comprising a DNA sequence which encodes a short hairpin micro-RNA (shmiR), said shmiR comprising:
an effector sequence of at least 17 nucleotides in length;
an effector complement sequence;
a stemloop sequence; and
primary micro RNA (pri-miRNA) backbone;
wherein the effector sequence is substantially complementary to a region of corresponding length in an RNA transcript set forth in any one of SEQ ID NOs: 1-13. Preferably, the effector sequence will be less than 30 nucleotides in length. For example, a suitable effector sequence may be in the range of 17-29 nucleotides in length. In a particularly preferred example, the effector sequence will be 21 nucleotides in length. More preferably, the effector sequence will be 21 nucleotides in length and the effector complement sequence will be 20 nucleotides in length.

In one example, the shmiR comprises an effector sequence which is substantially complementary to a region of corresponding length in an RNA transcript comprising or consisting of the sequence set forth in SEQ ID NO: 1. For example, the effector sequence may be substantially complementary to a region of corresponding length in an RNA transcript comprising or consisting of the sequence set forth in SEQ ID NO: 1 and contain 4 mismatch bases relative thereto. For example, the effector sequence may be substantially complementary to a region of corresponding length in an RNA transcript comprising or consisting of the sequence set forth in SEQ ID NO: 1 and contain 3 mismatch bases relative thereto. For example, the effector sequence may be substantially complementary to a region of corresponding length in an RNA transcript comprising or consisting of the sequence set forth in SEQ ID NO: 1 and contain 2 mismatch bases relative thereto. For example, the effector sequence may be substantially complementary to a region of corresponding length in an RNA transcript comprising or consisting of the sequence set forth in SEQ ID NO: 1 and contain 1 mismatch base relative thereto. For example, the effector sequence may be 100% complementary to a region of corresponding length in an RNA transcript comprising or consisting of the sequence set forth in SEQ ID NO: 1.

In one example, the shmiR comprises an effector sequence which is substantially complementary to a region of corresponding length in an RNA transcript comprising or consisting of the sequence set forth in SEQ ID NO: 2. For example, the effector sequence may be substantially complementary to a region of corresponding length in an RNA transcript comprising or consisting of the sequence set forth in SEQ ID NO: 2 and contain 4 mismatch bases relative thereto. For example, the effector sequence may be substantially complementary to a region of corresponding length in an RNA transcript comprising or consisting of the sequence set forth in SEQ ID NO: 2 and contain 3 mismatch bases relative thereto. For example, the effector sequence may be substantially complementary to a region of corresponding length in an RNA transcript comprising or consisting of the sequence set forth in SEQ ID NO: 2 and contain 2 mismatch bases relative thereto. For example, the effector sequence may be substantially complementary to a region of corresponding length in an RNA transcript comprising or consisting of the sequence set forth in SEQ ID NO: 2 and contain 1 mismatch base relative thereto. For example, the effector sequence may be 100% complementary to a region of corresponding length in an RNA transcript comprising or consisting of the sequence set forth in SEQ ID NO: 2.

In one example, the shmiR comprises an effector sequence which is substantially complementary to a region of corresponding length in an RNA transcript comprising or consisting of the sequence set forth in SEQ ID NO: 3. For example, the effector sequence may be substantially complementary to a region of corresponding length in an RNA transcript comprising or consisting of the sequence set forth in SEQ ID NO: 3 and contain 4 mismatch bases relative thereto. For example, the effector sequence may be substantially complementary to a region of corresponding length in an RNA transcript comprising or consisting of the sequence set forth in SEQ ID NO: 3 and contain 3 mismatch bases relative thereto. For example, the effector sequence may be substantially complementary to a region of corresponding length in an RNA transcript comprising or consisting of the sequence set forth in SEQ ID NO: 3 and contain 2 mismatch bases relative thereto. For example, the effector sequence may be substantially complementary to a region of corresponding length in an RNA transcript comprising or consisting of the sequence set forth in SEQ ID NO: 3 and contain 1 mismatch base relative thereto. For example, the effector sequence may be 100% complementary to a region of corresponding length in an RNA transcript comprising or consisting of the sequence set forth in SEQ ID NO: 3.

In one example, the shmiR comprises an effector sequence which is substantially complementary to a region of corresponding length in an RNA transcript comprising or consisting of the sequence set forth in SEQ ID NO: 4. For example, the effector sequence may be substantially complementary to a region of corresponding length in an RNA transcript comprising or consisting of the sequence set forth in SEQ ID NO: 4 and contain 4 mismatch bases relative thereto. For example, the effector sequence may be substantially complementary to a region of corresponding length in an RNA transcript comprising or consisting of the sequence set forth in SEQ ID NO: 4 and contain 3 mismatch bases relative thereto. For example, the effector sequence may be substantially complementary to a region of corresponding length in an RNA transcript comprising or consisting of the sequence set forth in SEQ ID NO: 4 and contain 2 mismatch bases relative thereto. For example, the effector sequence may be substantially complementary to a region of corresponding length in an RNA transcript comprising or consisting of the sequence set forth in SEQ ID NO: 4 and contain 1 mismatch base relative thereto. For example, the effector sequence may be 100% complementary to a region of corresponding length in an RNA transcript comprising or consisting of the sequence set forth in SEQ ID NO: 4.

In one example, the shmiR comprises an effector sequence which is substantially complementary to a region of corresponding length in an RNA transcript comprising or consisting of the sequence set forth in SEQ ID NO: 5. For example, the effector sequence may be substantially complementary to a region of corresponding length in an RNA transcript comprising or consisting of the sequence set forth in SEQ ID NO: 5 and contain 4 mismatch bases relative thereto. For example, the effector sequence may be substantially complementary to a region of corresponding length in an RNA transcript comprising or consisting of the sequence set forth in SEQ ID NO: 5 and contain 3 mismatch bases relative thereto. For example, the effector sequence may be substantially complementary to a region of corresponding length in an RNA transcript comprising or consisting of the sequence set forth in SEQ ID NO: 5 and contain 2 mismatch bases relative thereto. For example, the effector sequence may be substantially complementary to a region of corresponding length in an RNA transcript comprising or consisting of the sequence set forth in SEQ ID NO: 5 and contain 1 mismatch base relative thereto. For example, the effector sequence may be 100% complementary to a region of corresponding length in an RNA transcript comprising or consisting of the sequence set forth in SEQ ID NO: 5.

In one example, the shmiR comprises an effector sequence which is substantially complementary to a region of corresponding length in an RNA transcript comprising or consisting of the sequence set forth in SEQ ID NO: 6. For example, the effector sequence may be substantially complementary to a region of corresponding length in an RNA transcript comprising or consisting of the sequence set forth in SEQ ID NO: 6 and contain 4 mismatch bases relative thereto. For example, the effector sequence may be substantially complementary to a region of corresponding length in an RNA transcript comprising or consisting of the sequence set forth in SEQ ID NO: 6 and contain 3 mismatch bases relative thereto. For example, the effector sequence may be substantially complementary to a region of corresponding length in an RNA transcript comprising or consisting of the sequence set forth in SEQ ID NO: 6 and contain 2 mismatch bases relative thereto. For example, the effector sequence may be substantially complementary to a region of corresponding length in an RNA transcript comprising or consisting of the sequence set forth in SEQ ID NO: 6 and contain 1 mismatch base relative thereto. For example, the effector sequence may be 100% complementary to a region of corresponding length in an RNA transcript comprising or consisting of the sequence set forth in SEQ ID NO: 6.

In one example, the shmiR comprises an effector sequence which is substantially complementary to a region of corresponding length in an RNA transcript comprising or consisting of the sequence set forth in SEQ ID NO: 7. For example, the effector sequence may be substantially complementary to a region of corresponding length in an RNA transcript comprising or consisting of the sequence set forth in SEQ ID NO: 7 and contain 4 mismatch bases relative thereto. For example, the effector sequence may be substantially complementary to a region of corresponding length in an RNA transcript comprising or consisting of the sequence set forth in SEQ ID NO: 7 and contain 3 mismatch bases relative thereto. For example, the effector sequence may be substantially complementary to a region of corresponding length in an RNA transcript comprising or consisting of the sequence set forth in SEQ ID NO: 7 and contain 2 mismatch bases relative thereto. For example, the effector sequence may be substantially complementary to a region of corresponding length in an RNA transcript comprising or consisting of the sequence set forth in SEQ ID NO: 7 and contain 1 mismatch base relative thereto. For example, the effector sequence may be 100% complementary to a region of corresponding length in an RNA transcript comprising or consisting of the sequence set forth in SEQ ID NO: 7.

In one example, the shmiR comprises an effector sequence which is substantially complementary to a region of corresponding length in an RNA transcript comprising or consisting of the sequence set forth in SEQ ID NO: 8. For example, the effector sequence may be substantially complementary to a region of corresponding length in an RNA transcript comprising or consisting of the sequence set forth in SEQ ID NO: 8 and contain 4 mismatch bases relative thereto. For example, the effector sequence may be substantially complementary to a region of corresponding length in an RNA transcript comprising or consisting of the sequence set forth in SEQ ID NO: 8 and contain 3 mismatch bases relative thereto. For example, the effector sequence may be substantially complementary to a region of corresponding length in an RNA transcript comprising or consisting of the sequence set forth in SEQ ID NO: 8 and contain 2 mismatch bases relative thereto. For example, the effector sequence may be substantially complementary to a region of corresponding length in an RNA transcript comprising or consisting of the sequence set forth in SEQ ID NO: 8 and contain 1 mismatch base relative thereto. For example, the effector sequence may be 100% complementary to a region of corresponding length in an RNA transcript comprising or consisting of the sequence set forth in SEQ ID NO: 8.

In one example, the shmiR comprises an effector sequence which is substantially complementary to a region of corresponding length in an RNA transcript comprising or consisting of the sequence set forth in SEQ ID NO: 9. For example, the effector sequence may be substantially complementary to a region of corresponding length in an RNA transcript comprising or consisting of the sequence set forth in SEQ ID NO: 9 and contain 4 mismatch bases relative thereto. For example, the effector sequence may be substantially complementary to a region of corresponding length in an RNA transcript comprising or consisting of the sequence set forth in SEQ ID NO: 9 and contain 3 mismatch bases relative thereto. For example, the effector sequence may be substantially complementary to a region of corresponding length in an RNA transcript comprising or consisting of the sequence set forth in SEQ ID NO: 9 and contain 2 mismatch bases relative thereto. For example, the effector sequence may be substantially complementary to a region of corresponding length in an RNA transcript comprising or consisting of the sequence set forth in SEQ ID NO: 9 and contain 1 mismatch base relative thereto. For example, the effector sequence may be 100% complementary to a region of corresponding length in an RNA transcript comprising or consisting of the sequence set forth in SEQ ID NO: 9.

In one example, the shmiR comprises an effector sequence which is substantially complementary to a region of corresponding length in an RNA transcript comprising or consisting of the sequence set forth in SEQ ID NO: 10. For example, the effector sequence may be substantially complementary to a region of corresponding length in an RNA transcript comprising or consisting of the sequence set forth in SEQ ID NO: 10 and contain 4 mismatch bases relative thereto. For example, the effector sequence may be substantially complementary to a region of corresponding length in an RNA transcript comprising or consisting of the sequence set forth in SEQ ID NO: 10 and contain 3 mismatch bases relative thereto. For example, the effector sequence may be substantially complementary to a region of corresponding length in an RNA transcript comprising or consisting of the sequence set forth in SEQ ID NO: 10 and contain 2 mismatch bases relative thereto. For example, the effector sequence may be substantially complementary to a region of corresponding length in an RNA transcript comprising or consisting of the sequence set forth in SEQ ID NO: 10 and contain 1 mismatch base relative thereto. For example, the effector sequence may be 100% complementary to a region of corresponding length in an RNA transcript comprising or consisting of the sequence set forth in SEQ ID NO: 10.

In one example, the shmiR comprises an effector sequence which is substantially complementary to a region of corresponding length in an RNA transcript comprising or consisting of the sequence set forth in SEQ ID NO: 11. For example, the effector sequence may be substantially complementary to a region of corresponding length in an RNA transcript comprising or consisting of the sequence set forth in SEQ ID NO: 11 and contain 4 mismatch bases relative thereto. For example, the effector sequence may be substantially complementary to a region of corresponding length in an RNA transcript comprising or consisting of the sequence set forth in SEQ ID NO: 11 and contain 3 mismatch bases relative thereto. For example, the effector sequence may be substantially complementary to a region of corresponding length in an RNA transcript comprising or consisting of the sequence set forth in SEQ ID NO: 11 and contain 2 mismatch bases relative thereto. For example, the effector sequence may be substantially complementary to a region of corresponding length in an RNA transcript comprising or consisting of the sequence set forth in SEQ ID NO: 11 and contain 1 mismatch base relative thereto. For example, the effector sequence may be 100% complementary to a region of corresponding length in an RNA transcript comprising or consisting of the sequence set forth in SEQ ID NO: 11.

In one example, the shmiR comprises an effector sequence which is substantially complementary to a region of corresponding length in an RNA transcript comprising or consisting of the sequence set forth in SEQ ID NO: 12. For example, the effector sequence may be substantially complementary to a region of corresponding length in an RNA transcript comprising or consisting of the sequence set forth in SEQ ID NO: 12 and contain 4 mismatch bases relative thereto. For example, the effector sequence may be substantially complementary to a region of corresponding length in an RNA transcript comprising or consisting of the sequence set forth in SEQ ID NO: 12 and contain 3 mismatch bases relative thereto. For example, the effector sequence may be substantially complementary to a region of corresponding length in an RNA transcript comprising or consisting of the sequence set forth in SEQ ID NO: 12 and contain 2 mismatch bases relative thereto. For example, the effector sequence may be substantially complementary to a region of corresponding length in an RNA transcript comprising or consisting of the sequence set forth in SEQ ID NO: 12 and contain 1 mismatch base relative thereto. For example, the effector sequence may be 100% complementary to a region of corresponding length in an RNA transcript comprising or consisting of the sequence set forth in SEQ ID NO: 12.

In one example, the shmiR comprises an effector sequence which is substantially complementary to a region of corresponding length in an RNA transcript comprising or consisting of the sequence set forth in SEQ ID NO: 13. For example, the effector sequence may be substantially complementary to a region of corresponding length in an RNA transcript comprising or consisting of the sequence set forth in SEQ ID NO: 13 and contain 4 mismatch bases relative thereto. For example, the effector sequence may be substantially complementary to a region of corresponding length in an RNA transcript comprising or consisting of the sequence set forth in SEQ ID NO: 13 and contain 3 mismatch bases relative thereto. For example, the effector sequence may be substantially complementary to a region of corresponding length in an RNA transcript comprising or consisting of the sequence set forth in SEQ ID NO: 13 and contain 2 mismatch bases relative thereto. For example, the effector sequence may be substantially complementary to a region of corresponding length in an RNA transcript comprising or consisting of the sequence set forth in SEQ ID NO: 13 and contain 1 mismatch base relative thereto. For example, the effector sequence may be 100% complementary to a region of corresponding length in an RNA transcript comprising or consisting of the sequence set forth in SEQ ID NO: 13.

In accordance with an example in which the effector sequence of a shmiR of the disclosure is substantially complementary to a region of corresponding length in a PABPN1 miRNA transcript described herein and contains 1, 2, 3 or 4 mismatch base(s) relative thereto, it is preferred that the mismatch(es) are not located within the region corresponding to the seed region of the shmiR i.e., nucleotides 2-8 of the effector sequence.

In one example, the nucleic acid described herein may comprise a DNA sequence encoding a shmiR comprising: (i) an effector sequence which is substantially complementary to the sequence set forth in SEQ ID NO:14 with the exception of 1, 2, 3 or 4 base mismatches, provided that the effector sequence is capable of forming a duplex with a sequence set forth in SEQ ID NO: 14; and (ii) an effector complement sequence comprising a sequence which is substantially complementary to the effector sequence. For example, the shmiR encoded by the nucleic acid may comprise an effector sequence set forth in SEQ ID NO: 15 and an effector complement sequence which is substantially complementary to the sequence set forth in SEQ ID NO: 15 and capable of forming a duplex therewith. The effector complement sequence which is substantially complementary to the sequence set forth in SEQ ID NO:15 may be the sequence set forth in SEQ ID NO:14. A shmiR in accordance with this example is hereinafter designated "shmiR2".

In one example, the nucleic acid described herein may comprise a DNA sequence encoding a shmiR comprising: (i) an effector sequence which is substantially complementary to the sequence set forth in SEQ ID NO:16 with the exception of 1, 2, 3 or 4 base mismatches, provided that the effector sequence is capable of forming a duplex with a sequence set forth in SEQ ID NO: 16; and (ii) an effector complement sequence comprising a sequence which is substantially complementary to the effector sequence. For example, the shmiR encoded by the nucleic acid may comprise an effector sequence set forth in SEQ ID NO: 17 and an effector complement sequence which is substantially complementary to the sequence set forth in SEQ ID NO: 17 and capable of forming a duplex therewith. The effector complement sequence which is substantially complementary to the sequence set forth in SEQ ID NO:17 may be the sequence set forth in SEQ ID NO:16. A shmiR in accordance with this example is hereinafter designated "shmiR3".

In one example, the nucleic acid described herein may comprise a DNA sequence encoding a shmiR comprising: (i) an effector sequence which is substantially complementary to the sequence set forth in SEQ ID NO:18 with the exception of 1, 2, 3 or 4 base mismatches, provided that the effector sequence is capable of forming a duplex with a sequence set forth in SEQ ID NO:18; and (ii) an effector complement sequence comprising a sequence which is substantially complementary to the effector sequence. For example, the shmiR encoded by the nucleic acid may comprise an effector sequence set forth in SEQ ID NO: 19 and an effector complement sequence which is substantially complementary to the sequence set forth in SEQ ID NO: 19 and capable of forming a duplex therewith. The effector complement sequence which is substantially complementary to the sequence set forth in SEQ ID NO:19 may be the sequence set forth in SEQ ID NO:18. A shmiR in accordance with this example is hereinafter designated "shmiR4".

In one example, the nucleic acid described herein may comprise a DNA sequence encoding a shmiR comprising: (i) an effector sequence which is substantially complementary to the sequence set forth in SEQ ID NO:20 with the exception of 1, 2, 3 or 4 base mismatches, provided that the effector sequence is capable of forming a duplex with a sequence set forth in SEQ ID NO:20; and (ii) an effector complement sequence comprising a sequence which is substantially complementary to the effector sequence. For example, the shmiR encoded by the nucleic acid may comprise an effector sequence set forth in SEQ ID NO:21 and an effector complement sequence which is substantially complementary to the sequence set forth in SEQ ID NO:21 and capable of forming a duplex therewith. The effector complement sequence which is substantially complementary to the sequence set forth in SEQ ID NO:21 may be the sequence set forth in SEQ ID NO:20. A shmiR in accordance with this example is hereinafter designated "shmiR5".

In one example, the nucleic acid described herein may comprise a DNA sequence encoding a shmiR comprising: (i) an effector sequence which is substantially complementary to the sequence set forth in SEQ ID NO:22 with the exception of 1, 2, 3 or 4 base mismatches, provided that the effector sequence is capable of forming a duplex with a sequence set forth in SEQ ID NO:22; and (ii) an effector complement sequence comprising a sequence which is substantially complementary to the effector sequence. For example, the shmiR encoded by the nucleic acid may comprise an effector sequence set forth in SEQ ID NO:23 and an effector complement sequence which is substantially complementary to the sequence set forth in SEQ ID NO:23 and capable of forming a duplex therewith. The effector complement sequence which is substantially complementary to the sequence set forth in SEQ ID NO:23 may be the sequence set forth in SEQ ID NO:22. A shmiR in accordance with this example is hereinafter designated "shmiR6".

In one example, the nucleic acid described herein may comprise a DNA sequence encoding a shmiR comprising: (i) an effector sequence which is substantially complementary to the sequence set forth in SEQ ID NO:24 with the exception of 1, 2, 3 or 4 base mismatches, provided that the effector sequence is capable of forming a duplex with a sequence set forth in SEQ ID NO:24; and (ii) an effector complement sequence comprising a sequence which is substantially complementary to the effector sequence. For example, the shmiR encoded by the nucleic acid may comprise an effector sequence set forth in SEQ ID NO:25 and an effector complement sequence which is substantially complementary to the sequence set forth in SEQ ID NO:25 and capable of forming a duplex therewith. The effector complement sequence which is substantially complementary to the sequence set forth in SEQ ID NO:25 may be the sequence set forth in SEQ ID NO:24. A shmiR in accordance with this example is hereinafter designated "shmiR7".

In one example, the nucleic acid described herein may comprise a DNA sequence encoding a shmiR comprising: (i) an effector sequence which is substantially complementary to the sequence set forth in SEQ ID NO:26 with the exception of 1, 2, 3 or 4 base mismatches, provided that the effector sequence is capable of forming a duplex with a sequence set forth in SEQ ID NO:26; and (ii) an effector complement sequence comprising a sequence which is substantially complementary to the effector sequence. For example, the shmiR encoded by the nucleic acid may comprise an effector sequence set forth in SEQ ID NO:27 and an effector complement sequence which is substantially complementary to the sequence set forth in SEQ ID NO:27 and capable of forming a duplex therewith. The effector complement sequence which is substantially complementary to the sequence set forth in SEQ ID NO:27 may be the sequence set forth in SEQ ID NO:26. A shmiR in accordance with this example is hereinafter designated "shmiR9".

In one example, the nucleic acid described herein may comprise a DNA sequence encoding a shmiR comprising: (i) an effector sequence which is substantially complementary to the sequence set forth in SEQ ID NO:28 with the exception of 1, 2, 3 or 4 base mismatches, provided that the effector sequence is capable of forming a duplex with a sequence set forth in SEQ ID NO:28; and (ii) an effector complement sequence comprising a sequence which is substantially complementary to the effector sequence. For example, the shmiR encoded by the nucleic acid may comprise an effector sequence set forth in SEQ ID NO:29 and an effector complement sequence which is substantially complementary to the sequence set forth in SEQ ID NO:29 and capable of forming a duplex therewith. The effector complement sequence which is substantially complementary to the sequence set forth in SEQ ID NO:29 may be the sequence set forth in SEQ ID NO:28. A shmiR in accordance with this example is hereinafter designated "shmiR11".

In one example, the nucleic acid described herein may comprise a DNA sequence encoding a shmiR comprising: (i) an effector sequence which is substantially complementary to the sequence set forth in SEQ ID NO:30 with the exception of 1, 2, 3 or 4 base mismatches, provided that the effector sequence is capable of forming a duplex with a sequence set forth in SEQ ID NO:30; and (ii) an effector complement sequence comprising a sequence which is substantially complementary to the effector sequence. For example, the shmiR encoded by the nucleic acid may comprise an effector sequence set forth in SEQ ID NO:31 and an effector complement sequence which is substantially complementary to the sequence set forth in SEQ ID NO:31 and capable of forming a duplex therewith. The effector complement sequence which is substantially complementary to the sequence set forth in SEQ ID NO:31 may be the sequence set forth in SEQ ID NO:30. A shmiR in accordance with this example is hereinafter designated "shmiR13".

In one example, the nucleic acid described herein may comprise a DNA sequence encoding a shmiR comprising: (i) an effector sequence which is substantially complementary to the sequence set forth in SEQ ID NO:32 with the exception of 1, 2, 3 or 4 base mismatches, provided that the effector sequence is capable of forming a duplex with a sequence set forth in SEQ ID NO:32; and (ii) an effector complement sequence comprising a sequence which is substantially complementary to the effector sequence. For example, the shmiR encoded by the nucleic acid may comprise an effector sequence set forth in SEQ ID NO:33 and an effector complement sequence which is substantially complementary to the sequence set forth in SEQ ID NO:33 and capable of forming a duplex therewith. The effector complement sequence which is substantially complementary to the sequence set forth in SEQ ID NO:33 may be the sequence set forth in SEQ ID NO:32. A shmiR in accordance with this example is hereinafter designated "shmiR14".

In one example, the nucleic acid described herein may comprise a DNA sequence encoding a shmiR comprising: (i) an effector sequence which is substantially complementary to the sequence set forth in SEQ ID NO:34 with the exception of 1, 2, 3 or 4 base mismatches, provided that the effector sequence is capable of forming a duplex with a sequence set forth in SEQ ID NO:34; and (ii) an effector complement sequence comprising a sequence which is substantially complementary to the effector sequence. For example, the shmiR encoded by the nucleic acid may comprise an effector sequence set forth in SEQ ID NO:35 and an effector complement sequence which is substantially complementary to the sequence set forth in SEQ ID NO:35 and capable of forming a duplex therewith. The effector complement sequence which is substantially complementary to the sequence set forth in SEQ ID NO:35 may be the sequence set forth in SEQ ID NO:34. A shmiR in accordance with this example is hereinafter designated "shmiR15".

In one example, the nucleic acid described herein may comprise a DNA sequence encoding a shmiR comprising: (i) an effector sequence which is substantially complementary to the sequence set forth in SEQ ID NO:36 with the exception of 1, 2, 3 or 4 base mismatches, provided that the effector sequence is capable of forming a duplex with a sequence set forth in SEQ ID NO:36; and (ii) an effector complement sequence comprising a sequence which is substantially complementary to the effector sequence. For example, the shmiR encoded by the nucleic acid may comprise an effector sequence set forth in SEQ ID NO:37 and an effector complement sequence which is substantially complementary to the sequence set forth in SEQ ID NO:37 and capable of forming a duplex therewith. The effector complement sequence which is substantially complementary to the sequence set forth in SEQ ID NO:37 may be the sequence set forth in SEQ ID NO:36. A shmiR in accordance with this example is hereinafter designated "shmiR16".

In one example, the nucleic acid described herein may comprise a DNA sequence encoding a shmiR comprising: (i) an effector sequence which is substantially complementary to the sequence set forth in SEQ ID NO:38 with the exception of 1, 2, 3 or 4 base mismatches, provided that the effector sequence is capable of forming a duplex with a sequence set forth in SEQ ID NO:38; and (ii) an effector complement sequence comprising a sequence which is substantially complementary to the effector sequence. For example, the shmiR encoded by the nucleic acid may comprise an effector sequence set forth in SEQ ID NO:39 and an effector complement sequence which is substantially complementary to the sequence set forth in SEQ ID NO:39 and capable of forming a duplex therewith. The effector complement sequence which is substantially complementary to the sequence set forth in SEQ ID NO:39 may be the sequence set forth in SEQ ID NO:38. A shmiR in accordance with this example is hereinafter designated "shmiR17".

In any of the examples described herein, the shmiR encoded by the nucleic acid of the disclosure may comprise, in a 5' to 3' direction:
  a 5' flanking sequence of the pri-miRNA backbone;
  the effector complement sequence;
  the stemloop sequence;
  the effector sequence; and
  a 3' flanking sequence of the pri-miRNA backbone.

In any of the examples described herein, the shmiR encoded by the nucleic acid of the disclosure may comprise, in a 5' to 3' direction:
  a 5' flanking sequence of the pri-miRNA backbone;
  the effector sequence;
  the stemloop sequence;
  the effector complement sequence; and
  a 3' flanking sequence of the pri-miRNA backbone.

Suitable loop sequences may be selected from those known in the art. However, an exemplary stemloop sequence is set forth in SEQ ID NO: 40.

Suitable primary micro RNA (pri-miRNA or pri-R) backbones for use in a nucleic acid of the disclosure may be selected from those known in the art. For example, the pri-miRNA backbone may be selected from a pri-miR-30a backbone, a pri-miR-155 backbone, a pri-miR-21 backbone and a pri-miR-136 backbone. Preferably, however, the pri-miRNA backbone is a pri-miR-30a backbone. In accordance with an example in which the pri-miRNA backbone is a pri-miR-30a backbone, the 5' flanking sequence of the pri-miRNA backbone is set forth in SEQ ID NO: 41 and the 3' flanking sequence of the pri-miRNA backbone is set forth in SEQ ID NO: 42. Thus, the nucleic acid encoding the shmiRs of the disclosure (e.g., shmiR-1 to shmiR-16 described herein) may comprise DNA sequence encoding the sequence set forth in SEQ ID NO: 41 and DNA sequence encoding the sequence set forth in SEQ ID NO: 42.

In one example, the nucleic acid described herein may comprise a DNA sequence selected from the sequence set forth in any one of SEQ ID NOs: 56-68.

In one example, the nucleic acid described herein comprises or consists of a DNA sequence set forth in SEQ ID NO: 56 and encodes a shmiR (shmiR2) comprising or consisting of the sequence set forth in SEQ ID NO: 43.

In one example, the nucleic acid described herein comprises or consists of a DNA sequence set forth in SEQ ID NO: 57 and encodes a shmiR (shmiR3) comprising or consisting of the sequence set forth in SEQ ID NO: 44.

In one example, the nucleic acid described herein comprises or consists of a DNA sequence set forth in SEQ ID NO: 58 and encodes a shmiR (shmiR4) comprising or consisting of the sequence set forth in SEQ ID NO: 45.

In one example, the nucleic acid described herein comprises or consists of a DNA sequence set forth in SEQ ID NO: 59 and encodes a shmiR (shmiR5) comprising or consisting of the sequence set forth in SEQ ID NO: 46.

In one example, the nucleic acid described herein comprises or consists of a DNA sequence set forth in SEQ ID NO: 60 and encodes a shmiR (shmiR6) comprising or consisting of the sequence set forth in SEQ ID NO: 47.

In one example, the nucleic acid described herein comprises or consists of a DNA sequence set forth in SEQ ID NO: 61 and encodes a shmiR (shmiR7) comprising or consisting of the sequence set forth in SEQ ID NO: 48.

In one example, the nucleic acid described herein comprises or consists of a DNA sequence set forth in SEQ ID NO: 62 and encodes a shmiR (shmiR9) comprising or consisting of the sequence set forth in SEQ ID NO: 49.

In one example, the nucleic acid described herein comprises or consists of a DNA sequence set forth in SEQ ID NO: 63 and encodes a shmiR (shmiR11) comprising or consisting of the sequence set forth in SEQ ID NO: 50.

In one example, the nucleic acid described herein comprises or consists of a DNA sequence set forth in SEQ ID NO: 64 and encodes a shmiR (shmiR13) comprising or consisting of the sequence set forth in SEQ ID NO: 51.

In one example, the nucleic acid described herein comprises or consists of a DNA sequence set forth in SEQ ID NO: 65 and encodes a shmiR (shmiR14) comprising or consisting of the sequence set forth in SEQ ID NO: 52.

In one example, the nucleic acid described herein comprises or consists of a DNA sequence set forth in SEQ ID NO: 66 and encodes a shmiR (shmiR15) comprising or consisting of the sequence set forth in SEQ ID NO: 53.

In one example, the nucleic acid described herein comprises or consists of a DNA sequence set forth in SEQ ID NO: 67 and encodes a shmiR (shmiR16) comprising or consisting of the sequence set forth in SEQ ID NO: 54.

In one example, the nucleic acid described herein comprises or consists of a DNA sequence set forth in SEQ ID NO: 68 and encodes a shmiR (shmiR17) comprising or consisting of the sequence set forth in SEQ ID NO: 55.

Exemplary nucleic acids of the disclosure encode a shmiR selected from shmiR2, shmiR3, shmiR5, shmiR9, shmiR13, shmiR14 and shmiR17 as described herein. Nucleic acids of the disclosure encoding shmiRs selected from shmiR3, shmiR13, shmiR14 and shmiR17 as described herein are particularly preferred.

It will be understood by a person of skill in the art that a nucleic acid in accordance with the present disclosure may be combined or used in conjunction with one or more other nucleic acids comprising a DNA sequence encoding a shRNA or shmiR comprising an effector sequence of at least 17 contiguous nucleotides which is substantially complementary to a region of a RNA transcript corresponding to a PABPN1 protein which is causative of OPMD. In one example, a plurality of nucleic acids are provided comprising:

(a) at least one nucleic acid as described herein; and
(b) at least one further nucleic acid selected from:
  (i) a nucleic acid comprising a DNA sequence encoding a shmiR as described herein; or
  (ii) a nucleic acid comprising a DNA sequence encoding a short hairpin RNA (shRNA) comprising cognate effector and effector complement sequences of a shmiR as described herein;
wherein the shmiR encoded by the nucleic acid at (a) and the shmiR or shRNA encoded by the nucleic acid at (b) comprise different effector sequences.

Accordingly, in one example the plurality of nucleic acids of the disclosure may comprise two or more nucleic acids encoding shmiRs as described herein, such as two, or three, or four, or five, or six, or seven, or eight, or nine, or ten nucleic acids encoding shmiRs as described herein.

In another example, the plurality of nucleic acids of the disclosure comprises at least one nucleic acid encoding a shmiR as described herein and at least one nucleic acid comprising a DNA sequence encoding a shRNA comprising cognate effector and effector complement sequences of a shmiR as described herein. For example, a shRNA comprising the effector sequence and effector complement sequence of shmiR2 is hereinafter designated "shRNA2". For example, a shRNA comprising the effector sequence and effector complement sequence of shmiR3 is hereinafter designated "shRNA3". For example, a shRNA comprising the effector sequence and effector complement sequence of shmiR4 is hereinafter designated "shRNA4". For example, a shRNA comprising the effector sequence and effector complement sequence of shmiR5 is hereinafter designated "shRNA5". For example, a shRNA comprising the effector sequence and effector complement sequence of shmiR6 is hereinafter designated "shRNA6". For example, a shRNA comprising the effector sequence and effector complement sequence of shmiR7 is hereinafter designated "shRNA7". For example, a shRNA comprising the effector sequence and effector complement sequence of shmiR9 is hereinafter designated "shRNA9". For example, a shRNA comprising the effector sequence and effector complement sequence of shmiR11 is hereinafter designated "shRNA1". For example, a shRNA comprising the effector sequence and effector complement sequence of shmiR13 is hereinafter designated "shRNA13". For example, a shRNA comprising the effector sequence and effector complement sequence of shmiR14 is hereinafter designated "shRNA14". For example, a shRNA comprising the effector sequence and effector complement sequence of shmiR15 is hereinafter designated "shRNA15". For example, a shRNA comprising the effector sequence and effector complement sequence of shmiR16 is hereinafter designated "shRNA16". For example, a shRNA comprising the effector sequence and effector complement sequence of shmiR17 is hereinafter designated "shRNA17".

According to any example in which one or more of the nucleic acid in the plurality of nucleic acids described herein encodes a shRNA, the shRNA may comprise a loop or stem loop sequence positioned between the cognate effector and the effector complement sequences. Suitable loop sequences may be selected from those known in the art. Alternatively, suitable stem loops may be developed de novo. In one example, a nucleic acid of the plurality described herein encoding a shRNA may comprise a DNA sequence encoding a stem loop positioned between the DNA sequences encoding the effector sequence and the effector complement sequence respectively.

In one example, the plurality of nucleic acids described herein comprises a nucleic acid comprising or consisting of a DNA sequence encoding shmiR2, and at least one other nucleic acid of the disclosure which encodes a shmiR or shRNA targeting a region of a PABPN1 mRNA transcript. Exemplary nucleic acids encoding shmiR2 are described herein and shall be taken to apply mutatis mutandis to this example of the disclosure. In one example, the plurality of nucleic acids described herein comprises a nucleic acid which comprises or consists of a DNA sequence set forth in SEQ ID NO: 56 and which encodes a shmiR comprising or consisting of the sequence set forth in SEQ ID NO: 43, and at least one other nucleic acid of the disclosure which encodes a shmiR or shRNA targeting a region of a PABPN1 mRNA transcript. For example, the plurality of nucleic acids described herein may comprise (i) a nucleic acid comprising or consisting of a DNA sequence set forth in SEQ ID NO: 56 (shmiR2), and (ii) a nucleic acid comprising or consisting of a DNA sequence encoding one of shmiR3-shmiR7, shmiR9, shmiR11 or shmiR13-shmiR17 or the corresponding shRNA of any thereof.

In one example, the plurality of nucleic acids described herein comprises a nucleic acid comprising or consisting of a DNA sequence encoding shmiR3, and at least one other nucleic acid of the disclosure which encodes a shmiR or shRNA targeting a region of a PABPN1 mRNA transcript. Exemplary nucleic acids encoding shmiR3 are described herein and shall be taken to apply mutatis mutandis to this example of the disclosure. In one example, the plurality of nucleic acids described herein comprises a nucleic acid which comprises or consists of a DNA sequence set forth in SEQ ID NO: 57 and which encodes a shmiR comprising or consisting of the sequence set forth in SEQ ID NO: 44, and at least one other nucleic acid of the disclosure which encodes a shmiR or shRNA targeting a region of a PABPN1 mRNA transcript. For example, the plurality of nucleic acids described herein may comprise (i) a nucleic acid comprising or consisting of a DNA sequence set forth in SEQ ID NO: 57 (shmiR3), and (ii) a nucleic acid comprising or consisting of a DNA sequence encoding one of shmiR2, shmiR4-shmiR7, shmiR9, shmiR11 or shmiR13-shmiR17 or the corresponding shRNA of any thereof.

In one example, the plurality of nucleic acids described herein comprises a nucleic acid comprising or consisting of a DNA sequence encoding shmiR4, and at least one other nucleic acid of the disclosure which encodes a shmiR or shRNA targeting a region of a PABPN1 mRNA transcript. Exemplary nucleic acids encoding shmiR4 are described herein and shall be taken to apply mutatis mutandis to this example of the disclosure. In one example, the plurality of nucleic acids described herein comprises a nucleic acid which comprises or consists of a DNA sequence set forth in SEQ ID NO: 58 and which encodes a shmiR comprising or consisting of the sequence set forth in SEQ ID NO: 45, and at least one other nucleic acid of the disclosure which encodes a shmiR or shRNA targeting a region of a PABPN1 mRNA transcript. For example, the plurality of nucleic acids described herein may comprise (i) a nucleic acid comprising or consisting of a DNA sequence set forth in SEQ ID NO: 58 (shmiR4), and (ii) a nucleic acid comprising or consisting of a DNA sequence encoding one of shmiR2, shmiR3, shmiR5-shmiR7, shmiR9, shmiR11 or shmiR13-shmiR17 or the corresponding shRNA of any thereof.

In one example, the plurality of nucleic acids described herein comprises a nucleic acid comprising or consisting of a DNA sequence encoding shmiR5, and at least one other nucleic acid of the disclosure which encodes a shmiR or shRNA targeting a region of a PABPN1 mRNA transcript. Exemplary nucleic acids encoding shmiR5 are described herein and shall be taken to apply mutatis mutandis to this example of the disclosure. In one example, the plurality of nucleic acids described herein comprises a nucleic acid which comprises or consists of a DNA sequence set forth in SEQ ID NO: 59 and which encodes a shmiR comprising or consisting of the sequence set forth in SEQ ID NO: 46, and at least one other nucleic acid of the disclosure which encodes a shmiR or shRNA targeting a region of a PABPN1 mRNA transcript. For example, the plurality of nucleic acids described herein may comprise (i) a nucleic acid comprising or consisting of a DNA sequence set forth in SEQ ID NO: 59 (shmiR5), and (ii) a nucleic acid comprising or consisting of a DNA sequence encoding one of shmiR2-shmiR4, shmiR6-shmiR7, shmiR9, shmiR11 or shmiR13-shmiR17 or the corresponding shRNA of any thereof.

In one example, the plurality of nucleic acids described herein comprises a nucleic acid comprising or consisting of a DNA sequence encoding shmiR6, and at least one other nucleic acid of the disclosure which encodes a shmiR or shRNA targeting a region of a PABPN1 mRNA transcript. Exemplary nucleic acids encoding shmiR6 are described herein and shall be taken to apply mutatis mutandis to this example of the disclosure. In one example, the plurality of nucleic acids described herein comprises a nucleic acid which comprises or consists of a DNA sequence set forth in SEQ ID NO: 60 and which encodes a shmiR comprising or consisting of the sequence set forth in SEQ ID NO: 47, and at least one other nucleic acid of the disclosure which encodes a shmiR or shRNA targeting a region of a PABPN1 mRNA transcript. For example, the plurality of nucleic acids described herein may comprise (i) a nucleic acid comprising or consisting of a DNA sequence set forth in SEQ ID NO: 60 (shmiR6), and (ii) a nucleic acid comprising or consisting of a DNA sequence encoding one of shmiR2-shmiR5, shmiR7, shmiR9, shmiR11 or shmiR13-shmiR17 or the corresponding shRNA of any thereof.

In one example, the plurality of nucleic acids described herein comprises a nucleic acid comprising or consisting of a DNA sequence encoding shmiR7, and at least one other nucleic acid of the disclosure which encodes a shmiR or shRNA targeting a region of a PABPN1 mRNA transcript. Exemplary nucleic acids encoding shmiR7 are described herein and shall be taken to apply mutatis mutandis to this example of the disclosure. In one example, the plurality of nucleic acids described herein comprises a nucleic acid which comprises or consists of a DNA sequence set forth in SEQ ID NO: 61 and which encodes a shmiR comprising or consisting of the sequence set forth in SEQ ID NO: 48, and at least one other nucleic acid of the disclosure which encodes a shmiR or shRNA targeting a region of a PABPN1 mRNA transcript. For example, the plurality of nucleic acids described herein may comprise (i) a nucleic acid comprising or consisting of a DNA sequence set forth in SEQ ID NO: 61 (shmiR7), and (ii) a nucleic acid comprising or consisting of a DNA sequence encoding one of shmiR2-shmiR6, shmiR9, shmiR11 or shmiR13-shmiR17 or the corresponding shRNA of any thereof.

In one example, the plurality of nucleic acids described herein comprises a nucleic acid comprising or consisting of a DNA sequence encoding shmiR9, and at least one other nucleic acid of the disclosure which encodes a shmiR or shRNA targeting a region of a PABPN1 mRNA transcript. Exemplary nucleic acids encoding shmiR9 are described herein and shall be taken to apply mutatis mutandis to this example of the disclosure. In one example, the plurality of nucleic acids described herein comprises a nucleic acid which comprises or consists of a DNA sequence set forth in SEQ ID NO: 62 and which encodes a shmiR comprising or consisting of the sequence set forth in SEQ ID NO: 49, and at least one other nucleic acid of the disclosure which encodes a shmiR or shRNA targeting a region of a PABPN1 mRNA transcript. For example, the plurality of nucleic acids described herein may comprise (i) a nucleic acid comprising or consisting of a DNA sequence set forth in SEQ ID NO: 62 (shmiR9), and (ii) a nucleic acid comprising or consisting of a DNA sequence encoding one of shmiR2-shmiR7, shmiR11 or shmiR13-shmiR17 or the corresponding shRNA of any thereof.

In one example, the plurality of nucleic acids described herein comprises a nucleic acid comprising or consisting of a DNA sequence encoding shmiR11, and at least one other nucleic acid of the disclosure which encodes a shmiR or shRNA targeting a region of a PABPN1 mRNA transcript. Exemplary nucleic acids encoding shmiR11 are described herein and shall be taken to apply mutatis mutandis to this example of the disclosure. In one example, the plurality of nucleic acids described herein comprises a nucleic acid which comprises or consists of a DNA sequence set forth in SEQ ID NO: 63 and which encodes a shmiR comprising or consisting of the sequence set forth in SEQ ID NO: 50, and at least one other nucleic acid of the disclosure which encodes a shmiR or shRNA targeting a region of a PABPN1 mRNA transcript. For example, the plurality of nucleic acids described herein may comprise (i) a nucleic acid comprising or consisting of a DNA sequence set forth in SEQ ID NO: 63 (shmiR11), and (ii) a nucleic acid comprising or consisting of a DNA sequence encoding one of shmiR2-shmiR7, shmiR9 or shmiR13-shmiR17 or the corresponding shRNA of any thereof.

In one example, the plurality of nucleic acids described herein comprises a nucleic acid comprising or consisting of a DNA sequence encoding shmiR13, and at least one other nucleic acid of the disclosure which encodes a shmiR or shRNA targeting a region of a PABPN1 mRNA transcript. Exemplary nucleic acids encoding shmiR13 are described herein and shall be taken to apply mutatis mutandis to this example of the disclosure. In one example, the plurality of nucleic acids described herein comprises a nucleic acid which comprises or consists of a DNA sequence set forth in SEQ ID NO: 64 and which encodes a shmiR comprising or consisting of the sequence set forth in SEQ ID NO: 51, and at least one other nucleic acid of the disclosure which encodes a shmiR or shRNA targeting a region of a PABPN1 mRNA transcript. For example, the plurality of nucleic acids described herein may comprise (i) a nucleic acid comprising or consisting of a DNA sequence set forth in SEQ ID NO: 64 (shmiR13), and (ii) a nucleic acid comprising or consisting of a DNA sequence encoding one of shmiR2-shmiR7, shmiR9, shmiR11 or shmiR14-shmiR17 or the corresponding shRNA of any thereof.

In one example, the plurality of nucleic acids described herein comprises a nucleic acid comprising or consisting of a DNA sequence encoding shmiR14, and at least one other nucleic acid of the disclosure which encodes a shmiR or shRNA targeting a region of a PABPN1 mRNA transcript. Exemplary nucleic acids encoding shmiR14 are described herein and shall be taken to apply mutatis mutandis to this example of the disclosure. In one example, the plurality of nucleic acids described herein comprises a nucleic acid which comprises or consists of a DNA sequence set forth in SEQ ID NO: 65 and which encodes a shmiR comprising or consisting of the sequence set forth in SEQ ID NO: 52, and at least one other nucleic acid of the disclosure which encodes a shmiR or shRNA targeting a region of a PABPN1 mRNA transcript. For example, the plurality of nucleic acids described herein may comprise (i) a nucleic acid comprising or consisting of a DNA sequence set forth in SEQ ID NO: 65 (shmiR14), and (ii) a nucleic acid comprising or consisting of a DNA sequence encoding one of shmiR2-shmiR7, shmiR9, shmiR11 or shmiR13, shmiR15-shmiR17 or the corresponding shRNA of any thereof.

In one example, the plurality of nucleic acids described herein comprises a nucleic acid comprising or consisting of a DNA sequence encoding shmiR15, and at least one other nucleic acid of the disclosure which encodes a shmiR or shRNA targeting a region of a PABPN1 mRNA transcript. Exemplary nucleic acids encoding shmiR15 are described herein and shall be taken to apply mutatis mutandis to this example of the disclosure. In one example, the plurality of nucleic acids described herein comprises a nucleic acid which comprises or consists of a DNA sequence set forth in SEQ ID NO: 66 and which encodes a shmiR comprising or consisting of the sequence set forth in SEQ ID NO: 53, and at least one other nucleic acid of the disclosure which encodes a shmiR or shRNA targeting a region of a PABPN1 mRNA transcript. For example, the plurality of nucleic acids described herein may comprise (i) a nucleic acid comprising or consisting of a DNA sequence set forth in SEQ ID NO: 66 (shmiR15), and (ii) a nucleic acid comprising or consisting of a DNA sequence encoding one of shmiR2-shmiR7, shmiR9, shmiR11 or shmiR13-shmiR14, or shmiR16-shmiR17 or the corresponding shRNA of any thereof.

In one example, the plurality of nucleic acids described herein comprises a nucleic acid comprising or consisting of a DNA sequence encoding shmiR16, and at least one other nucleic acid of the disclosure which encodes a shmiR or shRNA targeting a region of a PABPN1 mRNA transcript. Exemplary nucleic acids encoding shmiR16 are described herein and shall be taken to apply mutatis mutandis to this example of the disclosure. In one example, the plurality of nucleic acids described herein comprises a nucleic acid which comprises or consists of a DNA sequence set forth in SEQ ID NO: 67 and which encodes a shmiR comprising or consisting of the sequence set forth in SEQ ID NO: 54, and at least one other nucleic acid of the disclosure which encodes a shmiR or shRNA targeting a region of a PABPN1 mRNA transcript. For example, the plurality of nucleic acids described herein may comprise (i) a nucleic acid comprising or consisting of a DNA sequence set forth in SEQ ID NO: 67 (shmiR16), and (ii) a nucleic acid comprising or consisting of a DNA sequence encoding one of shmiR2-shmiR7, shmiR9, shmiR11 or shmiR13-shmiR15, or shmiR17 or the corresponding shRNA of any thereof.

In one example, the plurality of nucleic acids described herein comprises a nucleic acid comprising or consisting of a DNA sequence encoding shmiR17, and at least one other nucleic acid of the disclosure which encodes a shmiR or shRNA targeting a region of a PABPN1 mRNA transcript. Exemplary nucleic acids encoding shmiR17 are described herein and shall be taken to apply mutatis mutandis to this example of the disclosure. In one example, the plurality of nucleic acids described herein comprises a nucleic acid which comprises or consists of a DNA sequence set forth in SEQ ID NO: 68 and which encodes a shmiR comprising or consisting of the sequence set forth in SEQ ID NO: 55, and at least one other nucleic acid of the disclosure which encodes a shmiR or shRNA targeting a region of a PABPN1 mRNA transcript. For example, the plurality of nucleic acids described herein may comprise (i) a nucleic acid comprising or consisting of a DNA sequence set forth in SEQ ID NO: 68 (shmiR17), and (ii) a nucleic acid comprising or consisting of a DNA sequence encoding one of shmiR2-shmiR7, shmiR9, shmiR11 or shmiR13-shmiR16 or the corresponding shRNA of any thereof.

In accordance with any example of a plurality of nucleic acids as described herein, the plurality of nucleic acids may comprise two or more nucleic acids encoding shmiRs or shRNAs as described herein, such as two, or three, or four, or five, or six, or seven, or eight, or nine, or ten nucleic acids encoding shmiRs as described herein, provided at that at least one of the nucleic acids encodes a shmiRs of the disclosure.

In one example, the plurality of nucleic acids comprises two nucleic acids encoding a shmiR or shRNA described herein, with the proviso that at least one of the nucleic acids encodes a shmiR as described herein. In one example, the plurality of nucleic acids comprises three nucleic acids encoding a shmiR or shRNA described herein, with the proviso that at least one of the nucleic acids encodes a shmiR as described herein. In one example, the plurality of nucleic acids comprises four nucleic acids encoding a shmiR or shRNA described herein, with the proviso that at least one of the nucleic acids encodes a shmiR as described herein. In one example, the plurality of nucleic acids comprises five nucleic acids encoding a shmiR or shRNA described herein, with the proviso that at least one of the nucleic acids encodes a shmiR as described herein. In one example, the plurality of nucleic acids comprises six nucleic acids encoding a shmiR or shRNA described herein, with the proviso that at least one of the nucleic acids encodes a shmiR as described herein. In one example, the plurality of nucleic acids comprises seven nucleic acids encoding a shmiR or shRNA described herein, with the proviso that at least one of the nucleic acids encodes a shmiR as described herein. In one example, the plurality of nucleic acids comprises eight nucleic acids encoding a shmiR or shRNA described herein, with the proviso that at least one of the nucleic acids encodes a shmiR as described herein. In one example, the plurality of nucleic acids comprises nine nucleic acids encoding a shmiR or shRNA described herein, with the proviso that at least one of the nucleic acids encodes a shmiR as described herein. In one example, the plurality of nucleic acids comprises ten nucleic acids encoding a shmiR or shRNA described herein, with the proviso that at least one of the nucleic acids encodes a shmiR as described herein.

In one example of a plurality of nucleic acids described herein, one of the nucleic acids comprises a DNA sequence encoding a shmiR having an effector sequence which is substantially complementary to a region of corresponding length in an RNA transcript comprising or consisting of the sequence set forth in SEQ ID NO: 1. Suitable nucleic acids encoding a shmiR having an effector sequence which is substantially complementary to a region of corresponding length in an RNA transcript comprising or consisting of the sequence set forth in SEQ ID NO: 1 are described herein e.g., for shmiR2.

In one example of a plurality of nucleic acids described herein, one of the nucleic acids comprises a DNA sequence encoding a shmiR having an effector sequence which is substantially complementary to a region of corresponding length in an RNA transcript comprising or consisting of the sequence set forth in SEQ ID NO: 2. Suitable nucleic acids encoding a shmiR having an effector sequence which is substantially complementary to a region of corresponding length in an RNA transcript comprising or consisting of the sequence set forth in SEQ ID NO: 2 are described herein e.g., for shmiR3.

In one example of a plurality of nucleic acids described herein, one of the nucleic acids comprises a DNA sequence encoding a shmiR having an effector sequence which is substantially complementary to a region of corresponding length in an RNA transcript comprising or consisting of the sequence set forth in SEQ ID NO: 4. Suitable nucleic acids encoding a shmiR having an effector sequence which is substantially complementary to a region of corresponding length in an RNA transcript comprising or consisting of the sequence set forth in SEQ ID NO: 4 are described herein e.g., for shmiR5.

In one example of a plurality of nucleic acids described herein, one of the nucleic acids comprises a DNA sequence encoding a shmiR having an effector sequence which is substantially complementary to a region of corresponding length in an RNA transcript comprising or consisting of the sequence set forth in SEQ ID NO: 7. Suitable nucleic acids encoding a shmiR having an effector sequence which is substantially complementary to a region of corresponding length in an RNA transcript comprising or consisting of the sequence set forth in SEQ ID NO: 7 are described herein e.g., for shmiR9.

In one example of a plurality of nucleic acids described herein, one of the nucleic acids comprises a DNA sequence encoding a shmiR having an effector sequence which is substantially complementary to a region of corresponding length in an RNA transcript comprising or consisting of the sequence set forth in SEQ ID NO: 9. Suitable nucleic acids encoding a shmiR having an effector sequence which is substantially complementary to a region of corresponding length in an RNA transcript comprising or consisting of the sequence set forth in SEQ ID NO: 9 are described herein e.g., for shmiR13.

In one example of a plurality of nucleic acids described herein, one of the nucleic acids comprises a DNA sequence encoding a shmiR having an effector sequence which is substantially complementary to a region of corresponding length in an RNA transcript comprising or consisting of the sequence set forth in SEQ ID NO: 10. Suitable nucleic acids encoding a shmiR having an effector sequence which is substantially complementary to a region of corresponding length in an RNA transcript comprising or consisting of the sequence set forth in SEQ ID NO: 10 are described herein e.g., for shmiR14.

In one example of a plurality of nucleic acids described herein, one of the nucleic acids comprises a DNA sequence encoding a shmiR having an effector sequence which is substantially complementary to a region of corresponding length in an RNA transcript comprising or consisting of the sequence set forth in SEQ ID NO: 13. Suitable nucleic acids encoding a shmiR having an effector sequence which is substantially complementary to a region of corresponding length in an RNA transcript comprising or consisting of the sequence set forth in SEQ ID NO: 13 are described herein e.g., for shmiR17.

An exemplary plurality of nucleic acids of the disclosure comprises at least two nucleic acids, each comprising a DNA sequence encoding a shmiR of the disclosure, wherein each shmiR comprises a different effector sequence.

In one example, each of the at least two nucleic acids encode a shmiR comprising an effector sequence which is substantially complementary to a region of corresponding length in an RNA transcript set forth in one of SEQ ID NOs: 1, 2, 4, 7, 9, 10 and 13. Exemplary nucleic acids of the disclosure encoding shmiRs comprising effector sequences which are substantially complementary to regions of corresponding length in the RNA transcripts set forth in SEQ ID NO: 1, 2, 4, 7, 9, 10 and 13 are described herein and shall be taken to apply mutatis mutandis to this example of the disclosure.

In one example, the at least two nucleic acids are selected from the group consisting of:

a nucleic acid comprising or consisting of a DNA sequence encoding a shmiR comprising an effector sequence set forth in SEQ ID NO: 15 and an effector complement sequence set forth in SEQ ID NO: 14 e.g., a nucleic acid comprising or consisting of a DNA sequence set forth in SEQ ID NO: 56 (shmiR2);

a nucleic acid comprising or consisting of a DNA sequence encoding a shmiR comprising an effector sequence set forth in SEQ ID NO: 17 and an effector complement sequence set forth in SEQ ID NO: 16 e.g., a nucleic acid comprising or consisting of a DNA sequence set forth in SEQ ID NO: 57 (shmiR3);

a nucleic acid comprising or consisting of a DNA sequence encoding a shmiR comprising an effector sequence set forth in SEQ ID NO: 21 and an effector complement sequence set forth in SEQ ID NO: 20 e.g., a nucleic acid comprising or consisting of a DNA sequence set forth in SEQ ID NO: 59 (shmiR5);

a nucleic acid comprising or consisting of a DNA sequence encoding a shmiR comprising an effector sequence set forth in SEQ ID NO: 27 and an effector complement sequence set forth in SEQ ID NO: 26 e.g., a nucleic acid comprising or consisting of a DNA sequence set forth in SEQ ID NO: 62 (shmiR9);

a nucleic acid comprising or consisting of a DNA sequence encoding a shmiR comprising an effector sequence set forth in SEQ ID NO: 31 and an effector complement sequence set forth in SEQ ID NO: 30 e.g., a nucleic acid comprising or consisting of a DNA sequence set forth in SEQ ID NO: 64 (shmiR13);

a nucleic acid comprising or consisting of a DNA sequence encoding a shmiR comprising an effector sequence set forth in SEQ ID NO: 33 and an effector complement sequence set forth in SEQ ID NO: 32 e.g., a nucleic acid comprising or consisting of a DNA sequence set forth in SEQ ID NO: 65 (shmiR14); and a nucleic acid comprising or consisting of a DNA sequence encoding a shmiR comprising an effector sequence set forth in SEQ ID NO: 39 and an effector complement sequence set forth in SEQ ID NO: 38 e.g., a nucleic acid comprising or consisting of a DNA sequence set forth in SEQ ID NO: 68 (shmiR17).

In one example, each of the at least two nucleic acids encode a shmiR comprising an effector sequence which is substantially complementary to a region of corresponding length in an RNA transcript set forth in one of SEQ ID NOs: 2, 9, 10 and 13. Exemplary nucleic acids of the disclosure encoding shmiRs comprising effector sequences which are substantially complementary to regions of corresponding length in the RNA transcripts set forth in SEQ ID NO: 2, 9, 10 and 13 are described herein and shall be taken to apply mutatis mutandis to this example of the disclosure.

In one example, the at least two nucleic acids are selected from the group consisting of:

a nucleic acid comprising or consisting of a DNA sequence encoding a shmiR comprising an effector sequence set forth in SEQ ID NO: 17 and an effector complement sequence set forth in SEQ ID NO: 16 e.g., a nucleic acid comprising or consisting of a DNA sequence set forth in SEQ ID NO: 57 (shmiR3);

a nucleic acid comprising or consisting of a DNA sequence encoding a shmiR comprising an effector sequence set forth in SEQ ID NO: 31 and an effector complement sequence set forth in SEQ ID NO: 30 e.g., a nucleic acid comprising or consisting of a DNA sequence set forth in SEQ ID NO: 64 (shmiR13);

a nucleic acid comprising or consisting of a DNA sequence encoding a shmiR comprising an effector sequence set forth in SEQ ID NO: 33 and an effector complement sequence set forth in SEQ ID NO: 32 e.g., a nucleic acid comprising or consisting of a DNA sequence set forth in SEQ ID NO: 65 (shmiR14); and a nucleic acid comprising or consisting of a DNA sequence encoding a shmiR comprising an effector sequence set forth in SEQ ID NO: 39 and an effector complement sequence set forth in SEQ ID NO: 38 e.g., a nucleic acid comprising or consisting of a DNA sequence set forth in SEQ ID NO: 68 (shmiR17).

In one example, the plurality of nucleic acids comprises a nucleic acid encoding a shmiR comprising an effector sequence which is substantially complementary to a region of corresponding length in an RNA transcript set forth in SEQ ID NO: 10, and a nucleic acid encoding a shmiR comprising an effector sequence which is substantially complementary to a region of corresponding length in an RNA transcript set forth in SEQ ID NO: 13. For example, the plurality of nucleic acids may comprise:

(a) a nucleic acid comprising or consisting of a DNA sequence encoding a shmiR comprising an effector sequence set forth in SEQ ID NO: 31 and an effector complement sequence set forth in SEQ ID NO: 30 e.g., a nucleic acid comprising or consisting of a DNA sequence set forth in SEQ ID NO: 64 (shmiR13); and (b) a nucleic acid comprising or consisting of a DNA sequence encoding a shmiR comprising an effector sequence set forth in SEQ ID NO: 39 and an effector complement sequence set forth in SEQ ID NO: 38 e.g., a nucleic acid comprising or consisting of a DNA sequence set forth in SEQ ID NO: 68 (shmiR17).

An exemplary plurality of nucleic acids of the disclosure comprises a nucleic acid comprising or consisting of a DNA sequence set forth in SEQ ID NO: 64 (shmiR13) and a nucleic acid comprising or consisting of a DNA sequence set forth in SEQ ID NO: 68 (shmiR17).

In one example, the plurality of nucleic acids comprises a nucleic acid encoding a shmiR comprising an effector sequence which is substantially complementary to a region of corresponding length in an RNA transcript set forth in SEQ ID NO: 2, and a nucleic acid encoding a shmiR comprising an effector sequence which is substantially complementary to a region of corresponding length in an RNA transcript set forth in SEQ ID NO: 9. For example, the plurality of nucleic acids may comprise:

(a) a nucleic acid comprising or consisting of a DNA sequence encoding a shmiR comprising an effector sequence set forth in SEQ ID NO: 17 and an effector complement sequence set forth in SEQ ID NO: 16, e.g., a nucleic acid comprising or consisting of a DNA sequence set forth in SEQ ID NO: 57 (shmiR3); and (b) a nucleic acid comprising or consisting of a DNA sequence encoding a shmiR comprising an effector sequence set forth in SEQ ID NO: 33 and an effector complement sequence set forth in SEQ ID NO: 32 e.g., a nucleic acid comprising or consisting of the sequence set forth in SEQ ID NO:65 (shmiR14).

An exemplary plurality of nucleic acids of the disclosure comprises a nucleic acid comprising or consisting of a DNA sequence set forth in SEQ ID NO: 64 (shmiR13) and a nucleic acid comprising or consisting of a DNA sequence set forth in SEQ ID NO: 68 (shmiR17).

In accordance with an example in which a plurality of nucleic acids is provided, two or more of the nucleic acids may form separate parts of the same polynucleotide. In another example, two or more of the nucleic acids in the plurality form parts of different polynucleotides, respectively. In another example, the plurality of nucleic acids described herein are provided as multiple components e.g., multiple compositions. For example, each of the nucleic acids of the plurality may be provided separately. Alternatively, in an example where three or more nucleic acids of the disclosure are provided, at least one of the nucleic acids may be provided separately and two or more of the plurality provided together.

In some examples, the or each nucleic acid in accordance with the present disclosure may comprise, or be in operable linkage with, additional elements e.g., to facilitate transcription of the shmiR or shRNA. For example, the or each nucleic acid may comprise a promoter operably linked to the sequence encoding a shmiR or shRNA described herein. Other elements e.g., transcriptional terminators and initiators, are known in the art and/or described herein.

Alternatively, or in addition, the or each nucleic acid in accordance with the present disclosure may comprise one or more restriction sites e.g., to facilitate cloning of the nucleic acid(s) into cloning or expression vectors. For example, the nucleic acids described herein may include a restriction site upstream and/or downstream of the sequence encoding a shmiR or shRNA of the disclosure. Suitable restriction enzyme recognition sequences will be known to a person of skill in the art. However, in one example, the nucleic acid(s) of the disclosure may include a BamH1 restriction site (GGATCC) at the 5' terminus i.e., upstream of the sequence encoding the shmiR or shRNA, and a EcoR1 restriction site (GAATTC) at the 3' terminus i.e., downstream of the sequence encoding the shmiR or shRNA.

ddRNAi Constructs

In one example, the or each nucleic acid of the disclosure is provided in the form of, or is comprised in, a DNA-directed RNAi (ddRNAi) construct. Accordingly, in one example, the present disclosure provides a ddRNAi construct comprising a nucleic acid as described herein. In another example, the present disclosure provides a ddRNAi construct comprising a plurality of nucleic acids described herein. In yet another example, the present disclosure provides a plurality of ddRNAi constructs, each comprising a nucleic acid of the plurality of nucleic acids as described herein (i.e., such that all of the nucleic acids of the plurality are represented in the plurality of ddRNAi constructs). Exemplary nucleic acids encoding shmiRs or shRNAs comprising effector sequences targeting a mRNA transcript of PABPN1 which is causative of OPMD are described herein and shall be taken to apply mutatis mutandis to this example of the disclosure.

In one example, the ddRNAi construct comprises a nucleic acid of the disclosure operably linked to a promoter.

In accordance with an example in which the ddRNAi construct comprises a plurality of the nucleic acids described herein, each of the nucleic acids may be operably-linked to a promoter. In one example, the nucleic acids in the ddRNAi construct may be operably linked to the same promoter. In one example, the nucleic acids in the ddRNAi construct may be operably linked to different promoters.

In one example, a ddRNAi construct of the disclosure comprises a nucleic acid comprising or consisting of a DNA sequence encoding shmiR2. For example, the ddRNAi construct may comprise a nucleic acid comprising or consisting of a DNA sequence encoding a shmiR having an effector sequence which is substantially complementary to a region of corresponding length in an RNA transcript comprising or consisting of the sequence set forth in SEQ ID NO: 1. Exemplary nucleic acids encoding shmiR2 are described herein and shall be taken to apply mutatis mutandis to this example of the disclosure. In one example, the ddRNAi construct comprises a nucleic acid which comprises or consists of a DNA sequence set forth in SEQ ID NO: 56 and which encodes a shmiR comprising or consisting of the sequence set forth in SEQ ID NO: 43. The ddRNAi construct may comprise one or more further nucleic acids of the disclosure comprising a DNA sequence encoding a shmiR or shRNA targeting a region of a PABPN1 mRNA transcript, such as a nucleic acid comprising or consisting of a DNA sequence encoding one of shmiR3-shmiR7, shmiR9, shmiR11 or shmiR13-shmiR17 or the corresponding shRNA of any thereof, as described herein. For example, the ddRNAi construct described herein may comprise (i) a nucleic acid comprising or consisting of a DNA sequence set forth in SEQ ID NO: 56 (shmiR2), and (ii) a nucleic acid comprising or consisting of a DNA sequence encoding one of shmiR3-shmiR7, shmiR9, shmiR11 or shmiR13-shmiR17 or the corresponding shRNA of any thereof. Exemplary nucleic acids encoding shmiRs designated shmiR3-shmiR7, shmiR9, shmiR11 and shmiR13-shmiR17 are described herein and shall be taken to apply mutatis mutandis to this example of the disclosure.

In one example, a ddRNAi construct of the disclosure comprises a nucleic acid comprising or consisting of a DNA sequence encoding shmiR3. For example, the ddRNAi construct may comprise a nucleic acid comprising or consisting of a DNA sequence encoding a shmiR having an effector sequence which is substantially complementary to a region of corresponding length in an RNA transcript comprising or consisting of the sequence set forth in SEQ ID NO: 2. Exemplary nucleic acids encoding shmiR3 are described herein and shall be taken to apply mutatis mutandis to this example of the disclosure. In one example, the ddRNAi construct comprises a nucleic acid which comprises or consists of a DNA sequence set forth in SEQ ID NO: 57 and which encodes a shmiR comprising or consisting of the sequence set forth in SEQ ID NO: 44. The ddRNAi construct may comprise one or more further nucleic acids of the disclosure comprising a DNA sequence encoding a shmiR or shRNA targeting a region of a PABPN1 mRNA transcript, such as a nucleic acid comprising or consisting of a DNA sequence encoding one of shmiR2, shmiR4-shmiR7, shmiR9, shmiR11 or shmiR13-shmiR17 or the corresponding shRNA of any thereof, as described herein. For example, the ddRNAi construct described herein may comprise (i) a nucleic acid comprising or consisting of a DNA sequence set forth in SEQ ID NO: 57 (shmiR3), and (ii) a nucleic acid comprising or consisting of a DNA sequence encoding one of shmiR2, shmiR4-shmiR7, shmiR9, shmiR11 or shmiR13-shmiR17 or the corresponding shRNA of any thereof. Exemplary nucleic acids encoding shmiRs designated shmiR2, shmiR4-shmiR7, shmiR9, shmiR11 or shmiR13-shmiR17 are described herein and shall be taken to apply mutatis mutandis to this example of the disclosure.

In one example, a ddRNAi construct of the disclosure comprises a nucleic acid comprising or consisting of a DNA sequence encoding shmiR4. For example, the ddRNAi construct may comprise a nucleic acid comprising or consisting of a DNA sequence encoding a shmiR having an effector sequence which is substantially complementary to a region of corresponding length in an RNA transcript comprising or consisting of the sequence set forth in SEQ ID NO: 3. Exemplary nucleic acids encoding shmiR4 are described herein and shall be taken to apply mutatis mutandis to this example of the disclosure. In one example, the ddRNAi construct comprises a nucleic acid which comprises or consists of a DNA sequence set forth in SEQ ID NO: 58 and which encodes a shmiR comprising or consisting of the sequence set forth in SEQ ID NO: 45. The ddRNAi construct may comprise one or more further nucleic acids of the disclosure comprising a DNA sequence encoding a shmiR or shRNA targeting a region of a PABPN1 mRNA transcript, such as a nucleic acid comprising or consisting of a DNA sequence encoding one of shmiR2, shmiR3, shmiR5-shmiR7, shmiR9, shmiR11 or shmiR13-shmiR17 or the corresponding shRNA of any thereof, as described herein. For example, the ddRNAi construct described herein may comprise (i) a nucleic acid comprising or consisting of a DNA sequence set forth in SEQ ID NO: 58 (shmiR4), and (ii) a nucleic acid comprising or consisting of a DNA sequence encoding one of shmiR2, shmiR3, shmiR5-shmiR7, shmiR9, shmiR11 or shmiR13-shmiR17 or the corresponding shRNA of any thereof. Exemplary nucleic acids encoding shmiRs designated shmiR2, shmiR3, shmiR5-shmiR7, shmiR9, shmiR11 or shmiR13-shmiR17 are described herein and shall be taken to apply mutatis mutandis to this example of the disclosure.

In one example, a ddRNAi construct of the disclosure comprises a nucleic acid comprising or consisting of a DNA sequence encoding shmiR5. For example, the ddRNAi construct may comprise a nucleic acid comprising or consisting of a DNA sequence encoding a shmiR having an effector sequence which is substantially complementary to a region of corresponding length in an RNA transcript comprising or consisting of the sequence set forth in SEQ ID NO: 4. Exemplary nucleic acids encoding shmiR5 are described herein and shall be taken to apply mutatis mutandis to this example of the disclosure. In one example, the ddRNAi construct comprises a nucleic acid which comprises or consists of a DNA sequence set forth in SEQ ID NO: 59 and which encodes a shmiR comprising or consisting of the sequence set forth in SEQ ID NO: 46. The ddRNAi construct may comprise one or more further nucleic acids of the disclosure comprising a DNA sequence encoding a shmiR or shRNA targeting a region of a PABPN1 mRNA transcript, such as a nucleic acid comprising or consisting of a DNA sequence encoding one of shmiR2-shmiR4, shmiR6-shmiR7, shmiR9, shmiR11 or shmiR13-shmiR17 or the corresponding shRNA of any thereof, as described herein. For example, the ddRNAi construct described herein may comprise (i) a nucleic acid comprising or consisting of a DNA sequence set forth in SEQ ID NO: 59 (shmiR5), and (ii) a nucleic acid comprising or consisting of a DNA sequence encoding one of shmiR2-shmiR4, shmiR6-shmiR7, shmiR9, shmiR11 or shmiR13-shmiR17 or the corresponding shRNA of any thereof. Exemplary nucleic acids encoding shmiRs designated shmiR2-shmiR4, shmiR6-shmiR7, shmiR9, shmiR11 or shmiR13-shmiR17 are described herein and shall be taken to apply mutatis mutandis to this example of the disclosure.

In one example, a ddRNAi construct of the disclosure comprises a nucleic acid comprising or consisting of a DNA sequence encoding shmiR6. For example, the ddRNAi construct may comprise a nucleic acid comprising or consisting of a DNA sequence encoding a shmiR having an effector sequence which is substantially complementary to a region of corresponding length in an RNA transcript comprising or consisting of the sequence set forth in SEQ ID NO: 5. Exemplary nucleic acids encoding shmiR6 are described herein and shall be taken to apply mutatis mutandis to this example of the disclosure. In one example, the ddRNAi construct comprises a nucleic acid which comprises or consists of a DNA sequence set forth in SEQ ID NO: 60 and which encodes a shmiR comprising or consisting of the sequence set forth in SEQ ID NO: 47. The ddRNAi construct may comprise one or more further nucleic acids of the disclosure comprising a DNA sequence encoding a shmiR or shRNA targeting a region of a PABPN1 mRNA transcript, such as a nucleic acid comprising or consisting of a DNA sequence encoding one of s shmiR2-shmiR5, shmiR7, shmiR9, shmiR11 or shmiR13-shmiR17 or the corresponding shRNA of any thereof, as described herein. For example, the ddRNAi construct described herein may comprise (i) a nucleic acid comprising or consisting of a DNA sequence set forth in SEQ ID NO: 60 (shmiR6), and (ii) a nucleic acid comprising or consisting of a DNA sequence encoding one of shmiR2-shmiR5, shmiR7, shmiR9, shmiR11 or shmiR13-shmiR17 or the corresponding shRNA of any thereof. Exemplary nucleic acids encoding shmiRs designated shmiR2-shmiR5, shmiR7, shmiR9, shmiR11 or shmiR13-shmiR17 are described herein and shall be taken to apply mutatis mutandis to this example of the disclosure.

In one example, a ddRNAi construct of the disclosure comprises a nucleic acid comprising or consisting of a DNA sequence encoding shmiR7. For example, the ddRNAi construct may comprise a nucleic acid comprising or consisting of a DNA sequence encoding a shmiR having an effector sequence which is substantially complementary to a region of corresponding length in an RNA transcript comprising or consisting of the sequence set forth in SEQ ID NO: 6. Exemplary nucleic acids encoding shmiR7 are described herein and shall be taken to apply mutatis mutandis to this example of the disclosure. In one example, the ddRNAi construct comprises a nucleic acid which comprises or consists of a DNA sequence set forth in SEQ ID NO: 61 and which encodes a shmiR comprising or consisting of the sequence set forth in SEQ ID NO: 48. The ddRNAi construct may comprise one or more further nucleic acids of the disclosure comprising a DNA sequence encoding a shmiR or shRNA targeting a region of a PABPN1 mRNA transcript, such as a nucleic acid comprising or consisting of a DNA sequence encoding one of shmiR2-shmiR6, shmiR9, shmiR11 or shmiR13-shmiR17 or the corresponding shRNA of any thereof, as described herein. For example, the ddRNAi construct described herein may comprise (i) a nucleic acid comprising or consisting of a DNA sequence set forth in SEQ ID NO: 61 (shmiR7), and (ii) a nucleic acid comprising or consisting of a DNA sequence encoding one of shmiR2-shmiR6, shmiR9, shmiR11 or shmiR13-shmiR17 or the corresponding shRNA of any thereof. Exemplary nucleic acids encoding shmiRs designated shmiR2-shmiR6, shmiR9, shmiR11 or shmiR13-shmiR17 are described herein and shall be taken to apply mutatis mutandis to this example of the disclosure.

In one example, a ddRNAi construct of the disclosure comprises a nucleic acid comprising or consisting of a DNA sequence encoding shmiR9. For example, the ddRNAi construct may comprise a nucleic acid comprising or consisting of a DNA sequence encoding a shmiR having an effector sequence which is substantially complementary to a region of corresponding length in an RNA transcript comprising or consisting of the sequence set forth in SEQ ID NO: 7. Exemplary nucleic acids encoding shmiR9 are described herein and shall be taken to apply mutatis mutandis to this example of the disclosure. In one example, the ddRNAi construct comprises a nucleic acid which comprises or consists of a DNA sequence set forth in SEQ ID NO: 62 and which encodes a shmiR comprising or consisting of the sequence set forth in SEQ ID NO: 49. The ddRNAi construct may comprise one or more further nucleic acids of the disclosure comprising a DNA sequence encoding a shmiR or shRNA targeting a region of a PABPN1 mRNA transcript, such as a nucleic acid comprising or consisting of a DNA sequence encoding one of shmiR2-shmiR7, shmiR11 or shmiR13-shmiR17 or the corresponding shRNA of any thereof, as described herein. For example, the ddRNAi construct described herein may comprise (i) a nucleic acid comprising or consisting of a DNA sequence set forth in SEQ ID NO: 62 (shmiR9), and (ii) a nucleic acid comprising or consisting of a DNA sequence encoding one of shmiR2-shmiR7, shmiR11 or shmiR13-shmiR17 or the corresponding shRNA of any thereof. Exemplary nucleic acids encoding shmiRs designated shmiR2-shmiR7, shmiR11 or shmiR13-shmiR17 are described herein and shall be taken to apply mutatis mutandis to this example of the disclosure.

In one example, a ddRNAi construct of the disclosure comprises a nucleic acid comprising or consisting of a DNA sequence encoding shmiR11. For example, the ddRNAi construct may comprise a nucleic acid comprising or consisting of a DNA sequence encoding a shmiR having an effector sequence which is substantially complementary to a region of corresponding length in an RNA transcript comprising or consisting of the sequence set forth in SEQ ID NO: 8. Exemplary nucleic acids encoding shmiR11 are described herein and shall be taken to apply mutatis mutandis to this example of the disclosure. In one example, the ddRNAi construct comprises a nucleic acid which comprises or consists of a DNA sequence set forth in SEQ ID NO: 63 and which encodes a shmiR comprising or consisting of the sequence set forth in SEQ ID NO: 50. The ddRNAi construct may comprise one or more further nucleic acids of the disclosure comprising a DNA sequence encoding a shmiR or shRNA targeting a region of a PABPN1 mRNA transcript, such as a nucleic acid comprising or consisting of a DNA sequence encoding one of shmiR2-shmiR7, shmiR9 or shmiR13-shmiR17 or the corresponding shRNA of any thereof, as described herein. For example, the ddRNAi construct described herein may comprise (i) a nucleic acid comprising or consisting of a DNA sequence set forth in SEQ ID NO: 63 (shmiR11), and (ii) a nucleic acid comprising or consisting of a DNA sequence encoding one of shmiR2-shmiR7, shmiR9 or shmiR13-shmiR17 or the corresponding shRNA of any thereof. Exemplary nucleic acids encoding shmiRs designated shmiR2-shmiR7, shmiR9 or shmiR13-shmiR17 are described herein and shall be taken to apply mutatis mutandis to this example of the disclosure.

In one example, a ddRNAi construct of the disclosure comprises a nucleic acid comprising or consisting of a DNA sequence encoding shmiR13. For example, the ddRNAi construct may comprise a nucleic acid comprising or consisting of a DNA sequence encoding a shmiR having an effector sequence which is substantially complementary to a region of corresponding length in an RNA transcript comprising or consisting of the sequence set forth in SEQ ID NO: 9. Exemplary nucleic acids encoding shmiR13 are described herein and shall be taken to apply mutatis mutandis to this example of the disclosure. In one example, the ddRNAi construct comprises a nucleic acid which comprises or consists of a DNA sequence set forth in SEQ ID NO: 64 and which encodes a shmiR comprising or consisting of the sequence set forth in SEQ ID NO: 51. The ddRNAi construct may comprise one or more further nucleic acids of the disclosure comprising a DNA sequence encoding a shmiR or shRNA targeting a region of a PABPN1 mRNA transcript, such as a nucleic acid comprising or consisting of a DNA sequence encoding one of shmiR2-shmiR7, shmiR9, shmiR11 or shmiR14-shmiR17 or the corresponding shRNA of any thereof, as described herein. For example, the ddRNAi construct described herein may comprise (i) a nucleic acid comprising or consisting of a DNA sequence set forth in SEQ ID NO: 64 (shmiR13), and (ii) a nucleic acid comprising or consisting of a DNA sequence encoding one of shmiR2-shmiR7, shmiR9, shmiR11 or shmiR14-shmiR17 or the corresponding shRNA of any thereof. Exemplary nucleic acids encoding shmiRs designated shmiR2-shmiR7, shmiR9, shmiR11 or shmiR14-shmiR17 are described herein and shall be taken to apply mutatis mutandis to this example of the disclosure.

In one example, a ddRNAi construct of the disclosure comprises a nucleic acid comprising or consisting of a DNA sequence encoding shmiR14. For example, the ddRNAi construct may comprise a nucleic acid comprising or consisting of a DNA sequence encoding a shmiR having an effector sequence which is substantially complementary to a region of corresponding length in an RNA transcript comprising or consisting of the sequence set forth in SEQ ID NO: 10. Exemplary nucleic acids encoding shmiR14 are described herein and shall be taken to apply mutatis mutandis to this example of the disclosure. In one example, the ddRNAi construct comprises a nucleic acid which comprises or consists of a DNA sequence set forth in SEQ ID NO: 65 and which encodes a shmiR comprising or consisting of the sequence set forth in SEQ ID NO: 52. The ddRNAi construct may comprise one or more further nucleic acids of the disclosure comprising a DNA sequence encoding a shmiR or shRNA targeting a region of a PABPN1 mRNA transcript, such as a nucleic acid comprising or consisting of a DNA sequence encoding one of shmiR2-shmiR7, shmiR9, shmiR11 or shmiR13, shmiR15-shmiR17 or the corresponding shRNA of any thereof, as described herein. For example, the ddRNAi construct described herein may comprise (i) a nucleic acid comprising or consisting of a DNA sequence set forth in SEQ ID NO: 65 (shmiR14), and (ii) a nucleic acid comprising or consisting of a DNA sequence encoding one of shmiR2-shmiR7, shmiR9, shmiR11 or shmiR13, shmiR15-shmiR17 or the corresponding shRNA of any thereof. Exemplary nucleic acids encoding shmiRs designated shmiR2-shmiR7, shmiR9, shmiR11 or shmiR13, shmiR15-shmiR17 are described herein and shall be taken to apply mutatis mutandis to this example of the disclosure.

In one example, a ddRNAi construct of the disclosure comprises a nucleic acid comprising or consisting of a DNA sequence encoding shmiR15. For example, the ddRNAi construct may comprise a nucleic acid comprising or consisting of a DNA sequence encoding a shmiR having an effector sequence which is substantially complementary to a region of corresponding length in an RNA transcript comprising or consisting of the sequence set forth in SEQ ID NO: 11. Exemplary nucleic acids encoding shmiR15 are described herein and shall be taken to apply mutatis mutandis to this example of the disclosure. In one example, the ddRNAi construct comprises a nucleic acid which comprises or consists of a DNA sequence set forth in SEQ ID NO: 66 and which encodes a shmiR comprising or consisting of the sequence set forth in SEQ ID NO: 53. The ddRNAi construct may comprise one or more further nucleic acids of the disclosure comprising a DNA sequence encoding a shmiR or shRNA targeting a region of a PABPN1 mRNA transcript, such as a nucleic acid comprising or consisting of a DNA sequence encoding one of shmiR2-shmiR7, shmiR9, shmiR11 or shmiR13-shmiR14, or shmiR16-shmiR17 or the corresponding shRNA of any thereof, as described herein. For example, the ddRNAi construct described herein may comprise (i) a nucleic acid comprising or consisting of a DNA sequence set forth in SEQ ID NO: 66 (shmiR15), and (ii) a nucleic acid comprising or consisting of a DNA sequence encoding one of shmiR2-shmiR7, shmiR9, shmiR11 or shmiR13-shmiR14, or shmiR16-shmiR17 or the corresponding shRNA of any thereof. Exemplary nucleic acids encoding shmiRs designated shmiR2-shmiR7, shmiR9, shmiR11 or shmiR13-shmiR14, or shmiR16-shmiR17 are described herein and shall be taken to apply mutatis mutandis to this example of the disclosure.

In one example, a ddRNAi construct of the disclosure comprises a nucleic acid comprising or consisting of a DNA sequence encoding shmiR16. For example, the ddRNAi construct may comprise a nucleic acid comprising or consisting of a DNA sequence encoding a shmiR having an effector sequence which is substantially complementary to a region of corresponding length in an RNA transcript comprising or consisting of the sequence set forth in SEQ ID NO: 12. Exemplary nucleic acids encoding shmiR16 are described herein and shall be taken to apply mutatis mutandis to this example of the disclosure. In one example, the ddRNAi construct comprises a nucleic acid which comprises or consists of a DNA sequence set forth in SEQ ID NO: 67 and which encodes a shmiR comprising or consisting of the sequence set forth in SEQ ID NO: 54. The ddRNAi construct may comprise one or more further nucleic acids of the disclosure comprising a DNA sequence encoding a shmiR or shRNA targeting a region of a PABPN1 mRNA transcript, such as a nucleic acid comprising or consisting of a DNA sequence encoding one of shmiR2-shmiR7, shmiR9, shmiR11 or shmiR13-shmiR15, or shmiR17 or the corresponding shRNA of any thereof, as described herein. For example, the ddRNAi construct described herein may comprise (i) a nucleic acid comprising or consisting of a DNA sequence set forth in SEQ ID NO: 67 (shmiR16), and (ii) a nucleic acid comprising or consisting of a DNA sequence encoding one of shmiR2-shmiR7, shmiR9, shmiR11 or shmiR13-shmiR15, or shmiR17 or the corresponding shRNA of any thereof. Exemplary nucleic acids encoding shmiRs designated shmiR2-shmiR7, shmiR9, shmiR11 or shmiR13-shmiR15, or shmiR17 are described herein and shall be taken to apply mutatis mutandis to this example of the disclosure.

In one example, a ddRNAi construct of the disclosure comprises a nucleic acid comprising or consisting of a DNA sequence encoding shmiR17. For example, the ddRNAi construct may comprise a nucleic acid comprising or consisting of a DNA sequence encoding a shmiR having an effector sequence which is substantially complementary to a region of corresponding length in an RNA transcript comprising or consisting of the sequence set forth in SEQ ID NO: 13. Exemplary nucleic acids encoding shmiR17 are described herein and shall be taken to apply mutatis mutandis to this example of the disclosure. In one example, the ddRNAi construct comprises a nucleic acid which comprises or consists of a DNA sequence set forth in SEQ ID NO: 68 and which encodes a shmiR comprising or consisting of the sequence set forth in SEQ ID NO: 55. The ddRNAi construct may comprise one or more further nucleic acids of the disclosure comprising a DNA sequence encoding a shmiR or shRNA targeting a region of a PABPN1 mRNA transcript, such as a nucleic acid comprising or consisting of a DNA sequence encoding one of shmiR2-shmiR7, shmiR9, shmiR11 or shmiR13-shmiR16 or the corresponding shRNA of any thereof, as described herein. For example, the ddRNAi construct described herein may comprise (i) a nucleic acid comprising or consisting of a DNA sequence set forth in SEQ ID NO: 68 (shmiR17), and (ii) a nucleic acid comprising or consisting of a DNA sequence encoding one of shmiR2-shmiR7, shmiR9, shmiR11 or shmiR13-shmiR16 or the corresponding shRNA of any thereof. Exemplary nucleic acids encoding shmiRs designated shmiR2-shmiR7, shmiR9, shmiR11 or shmiR13-shmiR16 are described herein and shall be taken to apply mutatis mutandis to this example of the disclosure.

In accordance with any example of a ddRNAi construct comprising a plurality of nucleic acids as described herein, the ddRNAi construct may comprise two or more nucleic acids encoding shmiRs or shRNAs as described herein, such as two, or three, or four, or five, or six, or seven, or eight, or nine, or ten nucleic acids encoding shmiRs or shRNAs as described herein, provided that at least one of the nucleic acids encodes a shmiR as described herein.

In one example, the ddRNAi construct comprises two nucleic acids encoding a shmiR or shRNA described herein, with the proviso that at least one of the nucleic acids encodes a shmiR as described herein. In one example, the ddRNAi construct comprises three nucleic acids encoding a shmiR or shRNA described herein, with the proviso that at least one of the nucleic acids encodes a shmiR as described herein. In one example, the ddRNAi construct comprises four nucleic acids encoding a shmiR or shRNA described herein, with the proviso that at least one of the nucleic acids encodes a shmiR as described herein. In one example, the ddRNAi construct comprises five nucleic acids encoding a shmiR or shRNA described herein, with the proviso that at least one of the nucleic acids encodes a shmiR as described herein. In one example, the ddRNAi construct comprises six nucleic acids encoding a shmiR or shRNA described herein, with the proviso that at least one of the nucleic acids encodes a shmiR as described herein. In one example, the ddRNAi construct comprises seven nucleic acids encoding a shmiR or shRNA described herein, with the proviso that at least one of the nucleic acids encodes a shmiR as described herein. In one example, the ddRNAi construct comprises eight nucleic acids encoding a shmiR or shRNA described herein, with the proviso that at least one of the nucleic acids encodes a shmiR as described herein. In one example, the ddRNAi construct comprises nine nucleic acids encoding a shmiR or shRNA described herein, with the proviso that at least one of the nucleic acids encodes a shmiR as described herein. In one example, the ddRNAi construct comprises ten nucleic acids encoding a shmiR or shRNA described herein, with the proviso that at least one of the nucleic acids encodes a shmiR as described herein.

An exemplary ddRNAi construct of the disclosure comprises at least two nucleic acids, each comprising a DNA sequence encoding a shmiR of the disclosure, wherein each shmiR comprises a different effector sequence. In one example, each of the at least two nucleic acids in the ddRNAi construct encode a shmiR comprising an effector sequence which is substantially complementary to a region of corresponding length in an RNA transcript set forth in one of SEQ ID NOs: 1, 2, 4, 7, 9, 10 and 13. Exemplary nucleic acids of the disclosure encoding shmiRs comprising effector sequences which are substantially complementary to regions of corresponding length in the RNA transcripts set forth in SEQ ID NO: 1, 2, 4, 7, 9, 10 and 13 are described herein and shall be taken to apply mutatis mutandis to this example of the disclosure describing ddRNAi constructs.

In one example, the ddRNAi construct comprises at least two nucleic acids selected from the group consisting of:

a nucleic acid comprising or consisting of a DNA sequence encoding a shmiR comprising an effector sequence set forth in SEQ ID NO: 15 and an effector complement sequence set forth in SEQ ID NO: 14 e.g., a nucleic acid comprising or consisting of a DNA sequence set forth in SEQ ID NO: 56 (shmiR2);

a nucleic acid comprising or consisting of a DNA sequence encoding a shmiR comprising an effector sequence set forth in SEQ ID NO: 17 and an effector complement sequence set forth in SEQ ID NO: 16 e.g., a nucleic acid comprising or consisting of a DNA sequence set forth in SEQ ID NO: 57 (shmiR3);

a nucleic acid comprising or consisting of a DNA sequence encoding a shmiR comprising an effector sequence set forth in SEQ ID NO: 21 and an effector complement sequence set forth in SEQ ID NO: 20 e.g., a nucleic acid comprising or consisting of a DNA sequence set forth in SEQ ID NO: 59 (shmiR5);

a nucleic acid comprising or consisting of a DNA sequence encoding a shmiR comprising an effector sequence set forth in SEQ ID NO: 27 and an effector complement sequence set forth in SEQ ID NO: 26 e.g., a nucleic acid comprising or consisting of a DNA sequence set forth in SEQ ID NO: 62 (shmiR9);

a nucleic acid comprising or consisting of a DNA sequence encoding a shmiR comprising an effector sequence set forth in SEQ ID NO: 31 and an effector complement sequence set forth in SEQ ID NO: 30 e.g., a nucleic acid comprising or consisting of a DNA sequence set forth in SEQ ID NO: 64 (shmiR13);

a nucleic acid comprising or consisting of a DNA sequence encoding a shmiR comprising an effector sequence set forth in SEQ ID NO: 33 and an effector complement sequence set forth in SEQ ID NO: 32 e.g., a nucleic acid comprising or consisting of a DNA sequence set forth in SEQ ID NO: 65 (shmiR14); and a nucleic acid comprising or consisting of a DNA sequence encoding a shmiR comprising an effector sequence set forth in SEQ ID NO: 39 and an effector complement sequence set forth in SEQ ID NO: 38 e.g., a nucleic acid comprising or consisting of a DNA sequence set forth in SEQ ID NO: 68 (shmiR17).

In one example, each of the at least two nucleic acids in the ddRNAi construct encode a shmiR comprising an effector sequence which is substantially complementary to a region of corresponding length in an RNA transcript set forth in one of SEQ ID NOs: 2, 9, 10 and 13. Exemplary nucleic acids of the disclosure encoding shmiRs comprising effector sequences which are substantially complementary to regions of corresponding length in the RNA transcripts set forth in SEQ ID NO: 2, 9, 10 and 13 are described herein and shall be taken to apply mutatis mutandis to this example of the disclosure describing ddRNAi constructs.

In one example, the ddRNAi construct comprises at least two nucleic acids selected from the group consisting of:

a nucleic acid comprising or consisting of a DNA sequence encoding a shmiR comprising an effector sequence set forth in SEQ ID NO: 17 and an effector complement sequence set forth in SEQ ID NO: 16 e.g., a nucleic acid comprising or consisting of a DNA sequence set forth in SEQ ID NO: 57 (shmiR3);

a nucleic acid comprising or consisting of a DNA sequence encoding a shmiR comprising an effector sequence set forth in SEQ ID NO: 31 and an effector complement sequence set forth in SEQ ID NO: 30 e.g., a nucleic acid comprising or consisting of a DNA sequence set forth in SEQ ID NO: 64 (shmiR13);

a nucleic acid comprising or consisting of a DNA sequence encoding a shmiR comprising an effector sequence set forth in SEQ ID NO: 33 and an effector complement sequence set forth in SEQ ID NO: 32 e.g., a nucleic acid comprising or consisting of a DNA sequence set forth in SEQ ID NO: 65 (shmiR14); and a nucleic acid comprising or consisting of a DNA sequence encoding a shmiR comprising an effector sequence set forth in SEQ ID NO: 39 and an effector complement sequence set forth in SEQ ID NO: 38 e.g., a nucleic acid comprising or consisting of a DNA sequence set forth in SEQ ID NO: 68 (shmiR17).

In one example, the ddRNAi construct of the disclosure comprises a nucleic acid encoding a shmiR comprising an effector sequence which is substantially complementary to a region of corresponding length in an RNA transcript set forth in SEQ ID NO: 10, and a nucleic acid encoding a shmiR comprising an effector sequence which is substantially complementary to a region of corresponding length in an RNA transcript set forth in SEQ ID NO: 13. For example, the ddRNAi construct may comprise:

(a) a nucleic acid comprising or consisting of a DNA sequence encoding a shmiR comprising an effector sequence set forth in SEQ ID NO: 31 and an effector complement sequence set forth in SEQ ID NO: 30 e.g., a nucleic acid comprising or consisting of a DNA sequence set forth in SEQ ID NO: 64 (shmiR13); and (b) a nucleic acid comprising or consisting of a DNA sequence encoding a shmiR comprising an effector sequence set forth in SEQ ID NO: 39 and an effector complement sequence set forth in SEQ ID NO: 38 e.g., a nucleic acid comprising or consisting of a DNA sequence set forth in SEQ ID NO: 68 (shmiR17).

An exemplary ddRNAi construct of the disclosure comprises a nucleic acid comprising or consisting of a DNA sequence set forth in SEQ ID NO: 64 (shmiR13) and a nucleic acid comprising or consisting of a DNA sequence set forth in SEQ ID NO: 68 (shmiR17).

In one example, the ddRNAi construct comprises a nucleic acid encoding a shmiR comprising an effector sequence which is substantially complementary to a region of corresponding length in an RNA transcript set forth in SEQ ID NO: 2, and a nucleic acid encoding a shmiR comprising an effector sequence which is substantially complementary to a region of corresponding length in an RNA transcript set forth in SEQ ID NO: 9. For example, the ddRNAi construct may comprise:

(a) a nucleic acid comprising or consisting of a DNA sequence encoding a shmiR comprising an effector sequence set forth in SEQ ID NO: 17 and an effector complement sequence set forth in SEQ ID NO: 16, e.g., a nucleic acid comprising or consisting of a DNA sequence set forth in SEQ ID NO: 57 (shmiR3); and (b) a nucleic acid comprising or consisting of a DNA sequence encoding a shmiR comprising an effector sequence set forth in SEQ ID NO: 33 and an effector complement sequence set forth in SEQ ID NO: 32 e.g., a nucleic acid comprising or consisting of the sequence set forth in SEQ ID NO:65 (shmiR14).

An exemplary ddRNAi construct of the disclosure comprises a nucleic acid comprising or consisting of a DNA sequence set forth in SEQ ID NO: 64 (shmiR13) and a nucleic acid comprising or consisting of a DNA sequence set forth in SEQ ID NO: 68 (shmiR17).

In each of the foregoing examples describing a ddRNAi construct of the disclosure, the or each nucleic acid comprised therein may be operably linked to a promoter. For example, the ddRNAi construct as described herein may comprise a single promoter which is operably-linked to the or each nucleic acid comprised therein e.g., to drive expression of one or more shmiRs and/or shRNAs from the ddRNAi construct.

In another example, each nucleic acid encoding a shmiR or shRNA of the disclosure comprised in the ddRNAi construct is operably-linked to a separate promoter.

According to an example in which multiple promoters are present, the promoters can be the same or different. For example, the construct may comprise multiple copies of the same promoter with each copy operably linked to a different nucleic acid of the disclosure. In another example, each promoter operably linked to a nucleic acid of the disclosure is different. For example, in a ddRNAi construct encoding two shmiRs, the two nucleic acids encoding the shmiRs are each operably linked to a different promoter. Equally, in an example in which a ddRNAi construct encodes one shmiR and one shRNA, the respective nucleic acids encoding the shmiR and shRNA are each operably linked to a different promoter.

In one example, the promoter is a constitutive promoter. The term "constitutive" when made in reference to a promoter means that the promoter is capable of directing transcription of an operably linked nucleic acid sequence in the absence of a specific stimulus (e.g., heat shock, chemicals, light, etc.). Typically, constitutive promoters are capable of directing expression of a coding sequence in substantially any cell and any tissue. The promoters used to transcribe shmiRs or shRNAs from the nucleic acid(s) of the disclosure include promoters for ubiquitin, CMV, β-actin, histone H4, EF-1α or pgk genes controlled by RNA polymerase II, or promoter elements controlled by RNA polymerase I.

In one example, a Pol II promoter such as CMV, SV40, U1, β-actin or a hybrid Pol II promoter is employed. Other suitable Pol II promoters are known in the art and may be used in accordance with this example of the disclosure. For example, a Pol II promoter system may be preferred in a ddRNAi construct of the disclosure which expresses a pri-miRNA which, by the action of the enzymes Drosha and Pasha, is processed into one or more shmiRs. A Pol II promoter system may also be preferred in a ddRNAi construct of the disclosure comprising sequence encoding a plurality of shRNAs or shmiRs under control of a single promoter. A Pol II promoter system may also be preferred where tissue specificity is desired.

In another example, a promoter controlled by RNA polymerase III is used, such as a U6 promoter (U6-1, U6-8, U6-9), H1 promoter, 7SL promoter, a human Y promoter (hY1, hY3, hY4 (see Maraia, et al., *Nucleic Acids Res* 22(15):3045-52 (1994)) and hY5 (see Maraia, et al., *Nucleic Acids Res* 24(18):3552-59 (1994)), a human MRP-7-2 promoter, an Adenovirus VA1 promoter, a human tRNA promoter, or a 5s ribosomal RNA promoter.

Suitable promoters for use in a ddRNAi construct of the disclosure are described in U.S. Pat. Nos. 8,008,468 and 8,129,510.

In one example, the promoter is a RNA pol III promoter. For example, the promoter is a U6 promoter (e.g., a U6-1, U6-8 or U6-9 promoter). In another example, the promoter is a H1 promoter.

In the case of a ddRNAi construct of the disclosure encoding a plurality of shmiRs, or encoding one or more shmiRs and a shRNA, as described herein, each of the nucleic acids in the ddRNAi construct is operably linked to a U6 promoter e.g., a separate U6 promoter.

In one example, the promoter in a construct is a U6 promoter. For example, the promoter is a U6-1 promoter. For example, the promoter is a U6-8 promoter. For example, the promoter is a U6-9 promoter.

In some examples, promoters of variable strength are employed. For example, use of two or more strong promoters (such as a Pol III-type promoter) may tax the cell, by, e.g., depleting the pool of available nucleotides or other cellular components needed for transcription. In addition, or alternatively, use of several strong promoters may cause a toxic level of expression of RNAi agents e.g., shmiRs or shRNAs, in the cell. Thus, in some examples one or more of the promoters in the multiple-promoter ddRNAi construct is weaker than other promoters in the construct, or all promoters in the construct may express the shmiRs or shRNAs at less than a maximum rate. Promoters may also be modified using various molecular techniques, or otherwise, e.g., through modification of various regulatory elements, to attain weaker levels or stronger levels of transcription. One means of achieving reduced transcription is to modify sequence elements within promoters known to control promoter activity. For example the Proximal Sequence Element (PSE) is known to effect the activity of human U6 promoters (see Domitrovich, et al., *Nucleic Acids Res* 31: 2344-2352 (2003). Replacing the PSE elements present in strong promoters, such as the human U6-1, U6-8 or U6-9 promoters, with the element from a weak promoter, such as the human U6-7 promoter, reduces the activity of the hybrid U6-1, U6-8 or U6-9 promoters. This approach has been used in the examples described in this application, but other means to achieve this outcome are known in the art.

Promoters useful in some examples of the present disclosure can be tissue-specific or cell-specific. The term "tissue specific" as it applies to a promoter refers to a promoter that is capable of directing selective transcription of a nucleic acid of interest to a specific type of tissue (e.g., tissue of the eye or muscle) in the relative absence of expression of the same nucleotide sequence of interest in a different type of tissue (e.g., liver). The term "cell-specific" as applied to a promoter refers to a promoter which is capable of directing selective transcription of a nucleic acid of interest in a specific type of cell in the relative absence of expression of the same nucleotide sequence of interest in a different type of cell within the same tissue. According to one example, a muscle-specific promoter is used, such as Spc512 or CK8.

However, other muscle-specific promoters are known in the art and are contemplated for use in a ddRNAi construct of the disclosure.

In one example, a ddRNAi construct of the disclosure may additionally comprise one or more enhancers to increase expression of the shmiRs or shRNAs encoded by the nucleic acids described herein. Enhancers appropriate for use in examples of the present disclosure include the Apo E HCR enhancer, a CMV enhancer (Xia et al, *Nucleic Acids Res* 31-17 (2003)), and other enhancers known to those skilled in the art. Suitable enhancers for use in a ddRNAi construct of the disclosure are described in U.S. Pat. No. 8,008,468.

In a further example, a ddRNAi construct of the disclosure may comprise a transcriptional terminator linked to a nucleic acid encoding a shmiR or shRNA of the disclosure. In the case of a ddRNAi construct comprising a plurality of nucleic acids described herein i.e., encoding multiple shmiRs and/or shRNAs, the terminators linked to each nucleic acid can be the same or different. For example, in a ddRNAi construct of the disclosure in which a RNA pol III promoter is employed, the terminator may be a contiguous stretch of 4 or more or 5 or more or 6 or more T residues. However, where different promoters are used, the terminators can be different and are matched to the promoter from the gene from which the terminator is derived. Such terminators include, but are not limited to, the SV40 poly A, the AdV VA1 gene, the 5S ribosomal RNA gene, and the terminators for human t-RNAs. Other promoter and terminator combinations are known in the art and are contemplated for use in a ddRNAi construct of the disclosure.

In addition, promoters and terminators may be mixed and matched, as is commonly done with RNA pol II promoters and terminators.

In one example, the promoter and terminator combinations used for each nucleic acid in a ddRNAi construct comprising a plurality of nucleic acids is different to decrease the likelihood of DNA recombination events between components.

One exemplary ddRNAi construct of the disclosure comprises a nucleic acid comprising or consisting of a DNA sequence encoding shmiR13 as described herein operably linked to a promoter, and a nucleic acid comprising or consisting of a DNA sequence encoding shmiR17 as described herein operably linked to a promoter. For example, an exemplary ddRNAi construct of the disclosure comprises a nucleic acid comprising or consisting of a DNA sequence set forth in SEQ ID NO: 64 operably linked to a promoter, and a nucleic acid comprising or consisting of a DNA sequence set forth in SEQ ID NO: 68 operably linked to a promoter. In one example, each nucleic acid in the ddRNAi construct encoding a shmiR is operably linked to a separate promoter. In another example, each nucleic acid in the ddRNAi construct encoding a shmiR is operably linked to the same promoter. For example, the or each promoter may be a U6 promoter e.g., a U6-1, U6-8 or U6-9 promoter. For example, the or each promoter may be a muscle specific promoter e.g., a Spc512 or CK8 promoter.

In accordance with an example in which the nucleic acids in the ddRNAi construct encoding shmiR13 and shmiR17 are operably-linked to the same Spc512 promoter, the ddRNAi construct comprises or consists of the DNA sequence set forth in SEQ ID NO: 72. In accordance with an example in which the nucleic acids in the ddRNAi construct encoding shmiR13 and shmiR17 are operably-linked to the same CK8 promoter, the ddRNAi construct comprises or consists of the DNA sequence set forth in SEQ ID NO: 70.

Another exemplary ddRNAi construct of the disclosure comprises a nucleic acid comprising or consisting of a DNA sequence encoding shmiR3 as described herein operably linked to a promoter, and a nucleic acid comprising or consisting of a DNA sequence encoding shmiR14 as described herein operably linked to a promoter. For example, an exemplary ddRNAi construct of the disclosure comprises a nucleic acid comprising or consisting of a DNA sequence set forth in SEQ ID NO: 57 operably linked to a promoter, and a nucleic acid comprising or consisting of a DNA sequence set forth in SEQ ID NO: 65 operably linked to a promoter. In one example, each nucleic acid in the ddRNAi construct encoding a shmiR is operably linked to a separate promoter. In another example, each nucleic acid in the ddRNAi construct encoding a shmiR is operably linked to the same promoter. For example, the or each promoter may be a U6 promoter e.g., a U6-1, U6-8 or U6-9 promoter. For example, the or each promoter may be a muscle specific promoter e.g., a Spc512 or CK8 promoter.

In accordance with an example in which the nucleic acids in the ddRNAi construct encoding shmiR3 and shmiR14 are operably-linked to the same Spc512 promoter, the ddRNAi construct comprises or consists of the DNA sequence set forth in SEQ ID NO: 71. In accordance with an example in which the nucleic acids in the ddRNAi construct encoding shmiR3 and shmiR14 are operably-linked to the same CK8 promoter, the ddRNAi construct comprises or consists of the DNA sequence set forth in SEQ ID NO: 69.

Also provided is a plurality of ddRNAi constructs. For example, a plurality of nucleic acids as encoding shmiRs as described herein may be provided within a plurality of ddRNAi constructs, wherein each ddRNAi construct comprises one or more of the plurality of nucleic acids described herein. Combinations of nucleic acids encoding shmiR have been described and shall be taken to apply mutatis mutandis to this example of the disclosure. In one example, each nucleic acid in the plurality of nucleic acids described herein is provided within its own ddRNAi construct.

According to any example in which a plurality of ddRNAi constructs is provided, each ddRNAi construct may also comprise one or more promoters operably linked to the nucleic acid(s) encoding the shmiR(s) comprised therein. In one example, each ddRNAi construct comprises a single nucleic acid encoding a shmiR and a promoter operably linked thereto. According to an example in which one or more of the plurality of ddRNAi constructs comprises two or more nucleic acid encoding shmiRs, each nucleic acid in the one or more ddRNAi constructs is operably linked to a separate promoter. In another example in which one or more of the plurality of ddRNAi constructs comprises two or more nucleic acid encoding shmiRs, the two or more nucleic acids are operably linked to the same promoter in the ddRNAi construct.

One exemplary plurality of ddRNAi constructs of the disclosure comprises a ddRNAi construct comprising a nucleic acid comprising or consisting of a DNA sequence encoding shmiR13 as described herein operably linked to a promoter, and a ddRNAi construct comprising a nucleic acid comprising or consisting of a DNA sequence encoding shmiR17 as described herein operably linked to a promoter. For example, an exemplary plurality of ddRNAi constructs of the disclosure comprises a ddRNAi construct comprising a nucleic acid comprising or consisting of a DNA sequence set forth in SEQ ID NO: 64 operably linked to a promoter, and a ddRNAi construct comprising a nucleic acid comprising or consisting of a DNA sequence set forth in SEQ ID NO: 68 operably linked to a promoter. In one example, the promoters are U6 promoters e.g., selected from a U6-1, U6-8 or U6-9 promoter. In another example, the promoters are muscle specific promoters e.g., Spc512 or CK8 promoters.

Another exemplary plurality of ddRNAi constructs of the disclosure comprises a ddRNAi construct comprising a nucleic acid comprising or consisting of a DNA sequence encoding shmiR3 as described herein operably linked to a promoter, and a ddRNAi construct comprising a nucleic acid comprising or consisting of a DNA sequence encoding shmiR14 as described herein operably linked to a promoter. For example, an exemplary plurality of ddRNAi constructs of the disclosure comprises a ddRNAi construct comprising a nucleic acid comprising or consisting of a DNA sequence set forth in SEQ ID NO: 57 operably linked to a promoter, and a ddRNAi construct comprising a nucleic acid comprising or consisting of a DNA sequence set forth in SEQ ID NO: 65 operably linked to a promoter. In one example, the promoters are U6 promoters e.g., selected from a U6-1, U6-8 or U6-9 promoter. In another example, the promoters are muscle specific promoters e.g., Spc512 or CK8 promoters.

In addition, the or each ddRNAi construct can comprise one or more multiple cloning sites and/or unique restriction sites that are located strategically, such that the promoter, nucleic acid encoding the shmiR or shRNA and/or other regulator elements are easily removed or replaced. The or each ddRNAi construct can be assembled from smaller oligonucleotide components using strategically located restriction sites and/or complementary sticky ends. The base vector for one approach according to the present disclosure comprises plasmids with a multilinker in which all sites are unique (though this is not an absolute requirement). Sequentially, each promoter is inserted between its designated unique sites resulting in a base cassette with one or more promoters, all of which can have variable orientation. Sequentially, again, annealed primer pairs are inserted into the unique sites downstream of each of the individual promoters, resulting in a single-, double- or multiple-expression cassette construct. The insert can be moved into e.g., an AdV backbone or an AAV backbone using two unique restriction enzyme sites (the same or different ones) that flank the single-, double- or multiple-expression cassette insert.

Generation of the or each ddRNAi construct can be accomplished using any suitable genetic engineering techniques known in the art, including without limitation, the standard techniques of PCR, oligonucleotide synthesis, restriction endonuclease digestion, ligation, transformation, plasmid purification, and DNA sequencing. If the or each construct is a viral construct, the construct comprises, for example, sequences necessary to package the ddRNAi construct into viral particles and/or sequences that allow integration of the ddRNAi construct into the target cell genome. In some examples, the or each viral construct additionally contains genes that allow for replication and propagation of virus, however such genes will be supplied in trans. Additionally, the or each viral construct cam contain genes or genetic sequences from the genome of any known organism incorporated in native form or modified. For example, a viral construct may comprise sequences useful for replication of the construct in bacteria.

The or each construct also may contain additional genetic elements. The types of elements that may be included in the construct are not limited in any way and may be chosen by one with skill in the art. For example, additional genetic elements may include a reporter gene, such as one or more genes for a fluorescent marker protein such as GFP or RFP; an easily assayed enzyme such as beta-galactosidase, luciferase, beta-glucuronidase, chloramphenical acetyl transferase or secreted embryonic alkaline phosphatase; or proteins for which immunoassays are readily available such as hormones or cytokines.

Other genetic elements that may find use in embodiments of the present disclosure include those coding for proteins which confer a selective growth advantage on cells such as adenosine deaminase, aminoglycodic phosphotransferase, dihydrofolate reductase, hygromycin-B-phosphotransferase, drug resistance, or those genes coding for proteins that provide a biosynthetic capability missing from an auxotroph. If a reporter gene is included along with the or each construct, an internal ribosomal entry site (IRES) sequence can be included. In one example, the additional genetic elements are operably linked with and controlled by an independent promoter/enhancer. In addition a suitable origin of replication for propagation of the construct in bacteria may be employed. The sequence of the origin of replication generally is separated from the ddRNAi construct and other genetic sequences. Such origins of replication are known in the art and include the pUC, ColE1, 2-micron or SV40 origins of replication.

Expression Vectors

In one example, a ddRNAi construct of the disclosure is included within an expression vector.

In one example, the expression vector is a plasmid e.g., as is known in the art. In one example, a suitable plasmid expression vector is a pAAV vector e.g., a self-complementary pAAV (pscAAV) plasmid vector or single-stranded pAAV (pssAAV) plasmid vector. As described herein, the plasmid may comprise one or more promoters (suitable examples of which are described) to drive expression of one or more shmiRs of the disclosure.

In one example, the expression vector is mini-circle DNA. Mini-circle DNA is described in U.S. Patent Publication No. 2004/0214329. Mini-circle DNA are useful for persistently high levels of nucleic acid transcription. The circular vectors are characterized by being devoid of expression-silencing bacterial sequences. For example, mini-circle vectors differ from bacterial plasmid vectors in that they lack an origin of replication, and lack drug selection markers commonly found in bacterial plasmids, e.g. β-lactamase, tet, and the like. Consequently, minicircle DNA becomes smaller in size, allowing more efficient delivery.

In one example, the expression vector is a viral vector.

A viral vector based on any appropriate virus may be used to deliver a ddRNAi of the disclosure. In addition, hybrid viral systems may be of use. The choice of viral delivery system will depend on various parameters, such as the tissue targeted for delivery, transduction efficiency of the system, pathogenicity, immunological and toxicity concerns, and the like.

Commonly used classes of viral systems used in gene therapy can be categorized into two groups according to whether their genomes integrate into host cellular chromatin (oncoretroviruses and lentiviruses) or persist in the cell nucleus predominantly as extrachromosomal episomes (adeno-associated virus, adenoviruses and herpesviruses). In one example, a viral vector of the disclosure integrates into a host cell's chromatin. In another example, a viral vector of the disclosure persists in a host cell's nucleus as an extrachomosomal episome.

In one example, a viral vector is an adenoviral (AdV) vector. Adenoviruses are medium-sized double-stranded, non-enveloped DNA viruses with linear genomes that is between 26-48 Kbp. Adenoviruses gain entry to a target cell by receptor-mediated binding and internalization, penetrating the nucleus in both non-dividing and dividing cells. Adenoviruses are heavily reliant on the host cell for survival and replication and are able to replicate in the nucleus of vertebrate cells using the host's replication machinery.

In one example, a viral vector is from the Parvoviridae family. The Parvoviridae is a family of small single-stranded, non-enveloped DNA viruses with genomes approximately 5000 nucleotides long. Included among the family members is adeno-associated virus (AAV). In one example, a viral vector of the disclosure is an AAV. AAV is a dependent parvovirus that generally requires co-infection with another virus (typically an adenovirus or herpesvirus) to initiate and sustain a productive infectious cycle. In the absence of such a helper virus, AAV is still competent to infect or transduce a target cell by receptor-mediated binding and internalization, penetrating the nucleus in both non-dividing and dividing cells. Because progeny virus is not produced from AAV infection in the absence of helper virus, the extent of transduction is restricted only to the initial cells that are infected with the virus. It is this feature which makes AAV a desirable vector for the present disclosure. Furthermore, unlike retrovirus, adenovirus, and herpes simplex virus, AAV appears to lack human pathogenicity and toxicity (Kay, et al., *Nature*. 424: 251 (2003)). Since the genome normally encodes only two genes it is not surprising that, as a delivery vehicle, AAV is limited by a packaging capacity of 4.5 single stranded kilobases (kb). However, although this size restriction may limit the genes that can be delivered for replacement gene therapies, it does not adversely affect the packaging and expression of shorter sequences such as shmiRs and shRNAs.

Another viral delivery system useful with the ddRNAi constructs of the disclosure is a system based on viruses from the family Retroviridae. Retroviruses comprise single-stranded RNA animal viruses that are characterized by two unique features. First, the genome of a retrovirus is diploid, consisting of two copies of the RNA. Second, this RNA is transcribed by the virion-associated enzyme reverse transcriptase into double-stranded DNA. This double-stranded DNA or provirus can then integrate into the host genome and be passed from parent cell to progeny cells as a stably-integrated component of the host genome.

In some examples, a viral vector is a lentivirus. Lentivirus vectors are often pseudotyped with vesicular somatitis virus glycoprotein (VSV-G), and have been derived from the human immunodeficiency virus (HIV); visan-maedi, which causes encephalitis (visna) or pneumonia in sheep; equine infectious anemia virus (EIAV), which causes autoimmune hemolytic anemia and encephalopathy in horses; feline immunodeficiency virus (FIV), which causes immune deficiency in cats; bovine immunodeficiency virus (BIV) which causes lymphadenopathy and lymphocytosis in cattle; and simian immunodeficiency virus (SIV), which causes immune deficiency and encephalopathy in non-human primates. Vectors that are based on HIV generally retain <5% of the parental genome, and <25% of the genome is incorporated into packaging constructs, which minimizes the possibility of the generation of reverting replication-competent HIV. Biosafety has been further increased by the development of self-inactivating vectors that contain deletions of the regulatory elements in the downstream long-terminal-repeat sequence, eliminating transcription of the packaging signal that is required for vector mobilization. One of the main advantages to the use of lentiviral vectors is that gene transfer is persistent in most tissues or cell types, even following cell division of the transduced cell.

A lentiviral-based construct used to express shmiRs and/or shRNAs from the nucleic acids and ddRNAi constructs of the disclosure comprises sequences from the 5' and 3' long terminal repeats (LTRs) of a lentivirus. In one example, the viral construct comprises an inactivated or self-inactivating 3' LTR from a lentivirus. The 3' LTR may be made self-inactivating by any method known in the art. For example, the U3 element of the 3' LTR contains a deletion of its enhancer sequence, e.g., the TATA box, Sp1 and NF-kappa B sites. As a result of the self-inactivating 3' LTR, the provirus that is integrated into the host genome will comprise an inactivated 5' LTR. The LTR sequences may be LTR sequences from any lentivirus from any species. The lentiviral-based construct also may incorporate sequences for MMLV or MSCV, RSV or mammalian genes. In addition, the U3 sequence from the lentiviral 5' LTR may be replaced with a promoter sequence in the viral construct. This may increase the titer of virus recovered from the packaging cell line. An enhancer sequence may also be included.

Other viral or non-viral systems known to those skilled in the art may be used to deliver the ddRNAi or nucleic acid of the present invention to cells of interest, including but not limited to gene-deleted adenovirus-transposon vectors (see Yant, et al., *Nature Biotech*. 20:999-1004 (2002)); systems derived from Sindbis virus or Semliki forest virus (see Perri, et al, *J. Virol*. 74(20):9802-07 (2002)); systems derived from Newcastle disease virus or Sendai virus.

Testing a shmiR or ddRNAi Construct of the Disclosure
Cell Culture Models

An example of cell line useful as a cell culture model for OPMD is the HEK293T cell line (HEK293T, ATCC, Manassas, USA) which has been transfected with a vector expressing normal Ala10-humanPABPN1-FLAG (Ala10) or mutant Ala17-humanPABPN1-FLAG (Ala17), the latter being hallmark of OPMD.

Further examples of cell lines useful as cell culture models for OPMD are the C2C12 mouse muscle cell and the ARPE-19 human retinal cells e.g., as described in Example 5

Another example of a cell line useful as a cell culture model for OPMD is the primary mouse myoblast (IM2) cell line stably transfected to express either normal Ala10-humanPABPN1-FLAG (Ala10) or mutant Ala17-human-PABPN1-FLAG (Ala17). An exemplary IM2 derived cell line which stably expresses mutant Ala17-humanPABPN1-FLAG (Ala17) is the H2 kB-D7e cell line. The H2 kB-D7e cell line is also described in Raz et al., (2011) *American Journal of Pathology*, 179(4):1988-2000.

Other cell lines suitable for cell culture models of OPMD are known in the art, such as described in Fan et al., (2001) *Human Molecular Genetics*, 10:2341-2351, Bao et al., (2002) *The Journal of Biological Chemistry*, 277:12263-12269, and Abu-Baker et al., (2003) *Human Molecular Genetics*, 12:2609-2623.

As exemplified herein, activity of a shmiR of the disclosure is determined by administering a nucleic acid encoding the shmiR, or a ddRNAi construct or expression vector comprising same, to the cell and subsequently measuring the level of expression of a RNA or protein encoded by the PABPN1 gene. For example, intracellular PABPN1 gene expression can be assayed by any one or more of RT-PCR, quantitative PCR, semi-quantitative PCR, or in-situ hybridization under stringent conditions, using one or more probes or primers which are specific for PABPN1. PABPN1 mRNA or DNA can also be assayed either by PCR using one or more probes or primers which are specific for PABPN1 or ELISA can be used to detect PABPN1 protein.

Polynucleotides which may be used in RT-PCR, quantitative PCR or semi-quantitative PCR techniques for detecting PABPN1 expression are known and commercially available (Thermo Fisher). However, polynucleotides useful for PCR-based detection methods can be designed based on sequence information available for PABPN1 using method and/or software known in the art. In one example, the presence or absence of PABPN1 mRNA may be detected using RT-PCR using standard methodologies known in the art. In one example, the presence or absence or relative amount of PABPN1 polypeptide or protein may be detected using any one or more of Western blotting, ELISA, or other standard quantitative or semiquantitative techniques available in the art, or a combination of such techniques. Techniques relying on antibody recognition of PABPN1 are contemplated and are described herein e.g., in Example 4. In one example, the presence or absence or relative abundance of PABPN1 polypeptide may be detected with techniques which comprise antibody capture of PABPN1 polypeptides in combination with electrophoretic resolution of captured PABPN1 polypeptides, for example using the Isonostic™ Assay (Target Discovery, Inc.). Antibodies are commercially available for PABPN1 protein.

Various means for normalizing differences in transfection or transduction efficiency and sample recovery are known in the art.

A nucleic acid, ddRNAi construct or expression vector of the disclosure that reduces expression of a mRNA or protein encoded by PABPN1 or that reduces the presence of nuclear aggregates of PABPN1 protein, relative to a level of mRNA expression or protein encoded by PABPN1 or an amount of nuclear aggregates of PABPN1 protein in the absence of the RNA of the disclosure, is considered to be useful for therapeutic applications e.g., such as treating OPMD by reducing expression of endogenous PABPN1 and replacing some or all of the endogenous PABPN1 with a PABPN1 protein which is not causative of OPMD as described herein.

Animal Models

There are several small animal models available for studying OPMD, examples of which are described in Uyama et al., (2005) *Acta Myologica*, 24(2):84-88 and Chartier and Simonelig (2013) *Drug Discovery Today: technologies*, 10:e103-107. An exemplary animal model is the A17.1 transgenic mouse model which has been described previously in Davies et al., (2005) Nature Medicine, 11:672-677 and Trollet et al., (2010) *Human Molecular Genetics*, 19(11):2191-2207.

Any of the foregoing animal models can be used to determine the efficacy of a shmiR or ddRNAi construct of the disclosure to knockdown, reduce or inhibit expression of a RNA or protein encoded by the PABPN1 gene.

Methods for assaying PABPN1 gene expression have been described herein with respect to cell models and shall be taken to apply mutatis mutandis to this example of the disclosure.

Agents for Replacement of Functional PABPN1

In one example, the present disclosure provides an agent for replacement of functional PABPN1 protein e.g., to a cell or animal. The functional PABPN1 protein will not be causative of OPMD, nor will it be encoded by a mRNA transcript which is targeted by the shmiR(s) or shRNA(s) of the disclosure.

In one example, the agent for replacement of functional PABPN1 protein to a cell or animal is a nucleic acid e.g., such as DNA or cDNA, encoding the functional PABPN1 protein. For example, the nucleic acid encoding the functional PABPN1 protein may be codon optimised e.g., contain one or more degenerate or wobble bases relative to the wild type PABPN1 nucleic acid but which encodes for identical amino acids, so that the corresponding mRNA sequence coding for the functional PABPN1 protein is not recognised by the shmiR(s) or shRNA(s) of the disclosure. For example, a codon optimised nucleic acid encoding the functional PABPN1 protein may comprise one or more degenerate or wobble bases relative to the wild type PABPN1 nucleic acid within the region targeted by the shmiR(s) or shRNA(s) of the disclosure. In one example, the one or more degenerate or wobble bases resides within a seed region of an effector sequence a shmiR or shRNA of the disclosure.

In one example, a nucleic acid encoding the functional PABPN1 protein is codon optimised such that its corresponding mRNA sequence is not recognised by the shmiR(s) or shRNA(s) of the disclosure. Preferably, the functional PABPN1 protein encoded by the codon optimised nucleic acid sequence comprises the amino acid sequence set forth in SEQ ID NO: 74 i.e., the amino acid sequence of the wild-type human PABPN1 protein. A skilled person will appreciate that there are a number of nucleotide sequence combinations which may be used to encode functional PABPN1 protein, and the choice of nucleotide sequence will ultimately depend on the effector sequence of the shmiR(s) or shRNA(s) i.e., such that the codon-optimised nucleic acid is not recognised by the shmiR(s) or shRNA(s). In one example, the agent for replacement of functional PABPN1 protein is a nucleic acid comprising the sequence set forth in SEQ ID NO: 73. In one example, the nucleic acid encoding the functional PABPN1 protein may also comprise a Kozak sequence.

In one example, the codon-optimised nucleic acid encoding the functional PABPN1 protein is operably-linked to a promoter suitable for expression of the functional PABPN1 protein. Promoters suitable for expression of the functional PABPN1 protein in tissue or the eye or muscle may be particularly suitable. One exemplary promoter suitable for use with the nucleic acid encoding the functional PABPN1 protein is a Spc512 promoter. Another exemplary promoter suitable for use with the nucleic acid encoding the functional PABPN1 protein is a CK8 promoter. However, any suitable promoter known in the art may be used. For example, other suitable promoters for use with the nucleic acid encoding the functional PABPN1 protein are described in US 20110212529 A1.

As described herein, promoters useful in some examples of the present disclosure can be tissue-specific or cell-specific.

In one example, a codon-optimised nucleic acid encoding the functional PABPN1 protein of the disclosure may additionally comprise one or more enhancers to increase expression of the functional PABPN1 protein and its corresponding mRNA transcript. Enhancers appropriate for use in this example of the present disclosure will be known to those skilled in the art.

A nucleic acid encoding the functional PABPN1 protein may be comprised within an expression vector. Exemplary expression vectors have been described in the context of nucleic acid and ddRNAi constructs of the disclosure and shall be taken to apply mutatis mutandis to this example.

Accordingly, in one example, an agent for replacement of functional PABPN1 protein to a cell or animal may be an expression vector comprising a codon-optimised nucleic acid encoding the functional PABPN1 protein. For example, an expression vector of the disclosure may comprise the codon-optimised nucleic acid encoding the functional PABPN1 protein and a promoter for expression therefor e.g., a SpC512 promoter or a CK8 promoter. In one example, the codon optimised nucleic acid encoding the functional PABPN1 protein may also comprise a Kozak sequence.

In one example, the nucleic acid encoding the functional PABPN1 protein as described herein may be comprised within a plasmid expression vector. Suitable plasmid expression vectors have been described herein and will be known in the art. In one example, a suitable plasmid expression vector is a pAAV vector e.g., a pscAAV plasmid vector or pssAAV plasmid vector.

In one example, the expression vector is mini-circle DNA. Mini-circle DNA vectors have been described herein.

In one example, the expression vector is a viral vector. For example, a viral vector based on any appropriate virus may be used to deliver a codon optimised nucleic acid encoding the functional PABPN1 protein of the disclosure. In addition, hybrid viral systems may be of use. The choice of viral delivery system will depend on various parameters, such as the tissue targeted for delivery, transduction efficiency of the system, pathogenicity, immunological and toxicity concerns, and the like.

Exemplary viral systems for delivery of genetic material to a cell or animal have been described in the context of the RNAs and ddRNAi constructs of the disclosure and shall be taken to apply mutatis mutandis to this example.

In one example, the viral vector is an AAV.

In one example, the viral vector is an AdV vector.

In one example, the viral vector is a lentivirus.

Other viral or non-viral systems known to those skilled in the art may be used to deliver the codon-optimised nucleic acid encoding functional PABPN1 protein of the present disclosure to cells of interest, including but not limited to gene-deleted adenovirus-transposon vectors (see Yant, et al., *Nature Biotech*. 20:999-1004 (2002)); systems derived from Sindbis virus or Semliki forest virus (see Perri, et al, *J. Virol.* 74(20):9802-07 (2002)); systems derived from Newcastle disease virus or Sendai virus.

In accordance with an example in which the codon-optimised nucleic acid encoding the functional PABPN1 protein as described herein is provided with a nucleic acid, ddRNAi construct or expression vector of the disclosure, the codon-optimised nucleic acid encoding the functional PABPN1 protein may be comprised within the same expression vector as the nucleic acid or ddRNAi construct. Thus, the codon-optimised nucleic acid encoding the functional PABPN1 protein and the nucleic acid or ddRNAi construct of the disclosure may be provided as a single DNA construct e.g., within an expression vector.

In an alternative example in which a codon-optimised nucleic acid encoding functional PABPN1 protein of the disclosure and a nucleic acid or ddRNAi construct of the disclosure are to be provided together, the codon-optimised nucleic acid encoding functional PABPN1 protein and the nucleic acid or ddRNAi construct may be comprised within different expression vectors. Where the codon-optimised nucleic acid encoding functional PABPN1 protein and the nucleic acid or ddRNAi construct are comprised within different expression vectors, the respective expression vectors may be the same type of vector or be different types of vectors.

Testing for Functional PABPN1
Cell Culture Models

Exemplary cell culture models of OPMD have been described herein, including in the working examples e.g., Examples 4 and 5. Such cell culture models of OPMD may be used for assessing the ability of an agent of the disclosure to replace functional PABPN1 protein in the presence of one or more nucleic acids encoding shmiRs of the disclosure targeting endogenous PABPN1.

Exemplary methods of detecting the presence or absence or relative amount of PABPN1 protein have also been described and apply mutatis mutandis to this example. For example, the presence or absence or relative amount of PABPN1 protein may be detected using any one or more of Western blotting, ELISA, or other standard quantitative or semiquantitative techniques available in the art, or a combination of such techniques. Techniques relying on antibody recognition of PABPN1 are contemplated and are described herein. The mutant and functional PABPN1 proteins may be expressed with appropriate protein tags e.g., myc or flag tags, to facilitate differential detection of mutant and functional PABPN1 proteins using appropriate antibodies which are commercially available. For example, the mutant human PABPN1 protein may be expressed with a FLAG tag. In this way, the presence or absence or relative amount of both mutant and functional PABPN1 protein may be detected independently in a cell following transfection or transduction of the cell with one or more nucleic acid(s), ddRNAi construct(s) or expression vector(s) of the disclosure and an agent for replacing functional PABPN1 protein of the disclosure (which may be provided separately or together as described herein).

In one example, the presence or absence or relative abundance of PABPN1 polypeptide may be detected with techniques which comprise antibody capture of PABPN1 polypeptides in combination with electrophoretic resolution of captured PABPN1 polypeptides, for example using the Isonostic™ Assay (Target Discovery, Inc.). Antibodies are commercially available for PABPN1 protein.

An agent of the disclosure that expresses a PABPN1 protein which is not causative of OPMD in a cell in the presence of the nucleic acid(s), ddRNAi construct(s) or expression vector(s) of the disclosure (expressing one or more shmiR(s) of the disclosure) is considered to be useful for treating OPMD.

Animal Models

Exemplary animal models for studying OPMD have been described.

Any of the foregoing animal models can be used to determine the efficacy of an agent of the disclosure to replace functional PABPN1 protein in vivo in the presence of one or more nucleic acid(s), ddRNAi construct(s) or expression vector(s) of the disclosure (expressing one or more shmiR(s) of the disclosure).

Methods for assaying PABPN1 expression have been described herein with respect to cell models and shall be taken to apply mutatis mutandis to this example of the disclosure.

In one example, histological and morphological analyses may be used to determine the efficacy of an agent of the disclosure to replace functional PABPN1 protein in vivo in the presence one or more nucleic acid(s), ddRNAi construct(s) or expression vector(s) of the disclosure (expressing one or more shmiR(s) of the disclosure). Further assays which may be used to determine efficacy of an agent of the disclosure to replace functional PABPN1 protein in vivo are described in Trollet et al., (2010) *Human Molecular Genetics*, 19(11): 2191-2207.

Single DNA Constructs for ddRNAi and Replacement of Functional PABPN1

The present disclosure also provides a single DNA construct comprising the nucleic acid encoding the functional PABPN1 protein as described herein and one or more ddRNAi construct(s) of the disclosure. An exemplary DNA construct comprising a nucleic acid encoding the functional PABPN1 protein and the ddRNAi construct of the disclosure is described in Example 7. In one example, the DNA construct may comprise a single ddRNAi construct as described herein in combination with the nucleic acid encoding the functional PABPN1 protein. In another example, the DNA construct may comprise a plurality of ddRNAi constructs in combination with the nucleic acid encoding the functional PABPN1 protein. In each example of the DNA construct, the DNA sequence encoding the functional PABPN1 protein is codon optimised such that its mRNA transcript is not targeted by the shmiR(s) of the ddRNAi construct(s).

In one example, functional PABPN1 protein is a wild-type human PABPN1 protein e.g., having a sequence set forth in SEQ ID NO: 74. It will be appreciated that the codon optimised DNA sequence encoding the functional PABPN1 protein may vary depending on the shmiR(s) encoded by the ddRNAi construct. That is, the specific codons within the PABPN1 mRNA transcript to be modified may vary depending on the effector sequence(s) of shmiR(s) encoded by the ddRNAi construct. In one example a codon optimised DNA sequence encoding the functional PABPN1 protein is set forth in SEQ ID NO: 73.

The DNA construct may also comprise one or more promoters e.g., to drive expression of the functional PABPN1 protein and/or shmiRs encoded by the ddRNAi construct. Promoters useful in some examples of the present disclosure can be tissue-specific or cell-specific. Exemplary promoters for use in the DNA constructs of the disclosure are muscle-specific promoter, such as for example, Spc512 and CK8. However, any suitable promoter known in the art is contemplated for use in the DNA construct described herein e.g., such as those described in US 20110212529 A1.

The DNA construct may be provided in the form of an expression vector or may be comprised within an expression vector. Suitable expression vectors have been described herein and will be known in the art.

In one example, the expression vector is a viral vector. For example, a viral vector based on any appropriate virus may be used to deliver the single DNA construct of the disclosure. In addition, hybrid viral systems may be of use. The choice of viral delivery system will depend on various parameters, such as the tissue targeted for delivery, transduction efficiency of the system, pathogenicity, immunological and toxicity concerns, and the like.

In another example, a suitable plasmid expression vector is a pAAV vector e.g., a pscAAV plasmid vector or pssAAV plasmid vector. Other exemplary viral systems for delivery of genetic material to a cell or animal have been described in the context of the ddRNAi constructs of the disclosure and shall be taken to apply mutatis mutandis to this example.

Figure 12:
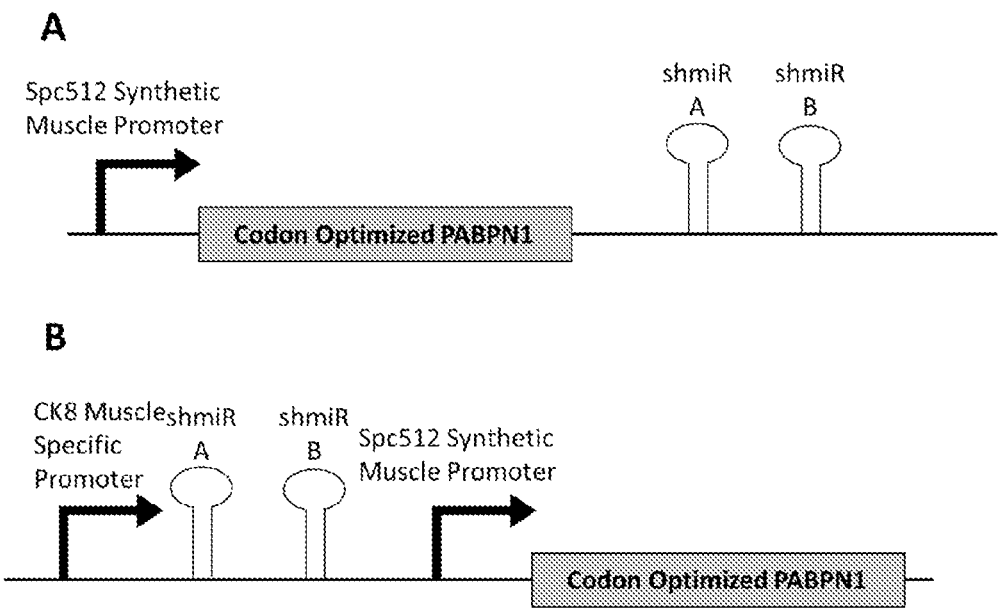
FIG. 12(A) is a schematic illustrating a construct for simultaneous gene silencing of endogenous PABPN1 and replacement with codon optimised PABPN1 generated by subcloning two shmiRs targeting wtPABPN1 into the 3' untranslated region of the codon optimized PABPN1 transcript in the pAAV2 vector backbone.
FIG. 12(B) is a schematic illustrating a construct for simultaneous gene silencing of endogenous PABPN1 and replacement with codon optimised PABPN1 generated by subcloning two shmiRs targeting wtPABPN1 into the sequence upstream of the optPABPN1.

In one example, the DNA construct is provided in the form of a pAAV expression vector comprising, in a 5' to 3' direction, a muscle-specific promoter e.g., a Spc512 promoter, a ddRNAi construct as described herein and a PABPN1 construct described herein, e.g., wherein the ddRNAi construct is positioned in the 3' untranslated region (UTR) of nucleic acid encoding the functional PABPN1 protein. A DNA construct in accordance with this example is illustrated in FIG. 12A.

An exemplary DNA construct in accordance with this example is a pAAV expression vector comprising, in a 5' to 3' direction:
(a) a muscle-specific promoter e.g., Spc512;
(b) a PABPN1 construct as described herein comprising a DNA sequence encoding a functional PABPN1 protein having a mRNA transcript which is not targeted by the shmiRs encoded by the ddRNAi construct; and
(c) a ddRNAi construct of the disclosure comprising a nucleic acid comprising a DNA sequence encoding shmiR17 as described herein and a nucleic acid comprising a DNA sequence encoding shmiR13 as described herein.

In accordance with this example, the DNA construct may comprise or consist of the DNA sequence set forth in SEQ ID NO: 72.

Another exemplary DNA construct in accordance with this example is a pAAV expression vector comprising, in a 5' to 3' direction:
(a) a muscle-specific promoter e.g., Spc512;
(b) a PABPN1 construct as described herein comprising a DNA sequence encoding a functional PABPN1 protein having a mRNA transcript which is not targeted by the shmiRs encoded by the ddRNAi construct; and
(c) a ddRNAi construct of the disclosure comprising a nucleic acid comprising a DNA sequence encoding shmiR3 as described herein and a nucleic acid comprising a DNA sequence encoding shmiR14 as described herein.

In accordance with this example, DNA construct may comprise or consist of the DNA sequence set forth in SEQ ID NO: 71.

In another example, the DNA construct is provided in the form of a pAAV expression vector comprising, in a 5' to 3' direction, a first muscle-specific promoter e.g., a CK8 promoter, a PABPN1 construct as described herein, a second muscle-specific promoter e.g., a Spc512 promoter, and a ddRNAi construct as described herein, wherein the first and second muscle-specific promoters are in operable linkage with the PABPN1 construct and the ddRNAi construct respectively. A DNA construct in accordance with this example is illustrated in FIG. 12B. For example, the promoter which is in operable linkage with the PABPN1 construct will be operably linked to the DNA sequence encoding a functional PABPN1 protein comprised therein, the promoter which is in operable linkage with the ddRNAi construct will be operably-linked with one or more nucleic acids encoding a shmiR of the disclosure. A DNA construct in accordance with this example is illustrated in FIG. 12A.

An exemplary DNA construct in accordance with this example is a pAAV expression vector comprising, in a 5' to 3' direction:
(a) a muscle-specific promoter e.g., CK8 promoter, positioned upstream of a ddRNAi construct of the disclosure comprising a nucleic acid comprising a DNA sequence encoding shmiR17 as described herein and a nucleic acid comprising a DNA sequence encoding shmiR13 as described herein; and
(b) a muscle-specific promoter e.g., Spc512 promoter, positioned upstream of a PABPN1 construct as described herein comprising a DNA sequence encoding a functional PABPN1 protein having a mRNA transcript which is not targeted by the shmiRs encoded by the ddRNAi construct.

In accordance with this example, the DNA construct may comprise or consist of the DNA sequence set forth in SEQ ID NO: 70.

Another exemplary DNA construct in accordance with this example is a pAAV expression vector comprising, in a 5' to 3' direction:

(a) a muscle-specific promoter e.g., CK8 promoter, positioned upstream of a ddRNAi construct of the disclosure comprising a nucleic acid comprising a DNA sequence encoding shmiR3 as described herein and a nucleic acid comprising a DNA sequence encoding shmiR14 as described herein; and (b) a muscle-specific promoter e.g., Spc512 promoter, positioned upstream of a PABPN1 construct as described herein comprising a DNA sequence encoding a functional PABPN1 protein having a mRNA transcript which is not targeted by the shmiRs encoded by the ddRNAi construct.

In accordance with this example, the DNA construct may comprise or consist of the DNA sequence set forth in SEQ ID NO: 69.

An exemplary ddRNAi construct encoding shmiR13 and shmiR17 for inclusion in a DNA construct of the disclosure comprises a nucleic acid comprising or consisting of a DNA sequence encoding a shmiR comprising an effector sequence set forth in SEQ ID NO: 31 and an effector complement sequence which is substantially complementary to the sequence set forth in SEQ ID NO: 31 e.g., an effector complement sequence set forth in SEQ ID NO: 30 (shmiR13), and a nucleic acid comprising or consisting of a DNA sequence encoding a shmiR comprising an effector sequence set forth in SEQ ID NO: 39 and an effector complement sequence which is substantially complementary to the sequence set forth in SEQ ID NO: 39 e.g., an effector complement sequence set forth in SEQ ID NO: 38 (shmiR17). For example, the ddRNAi construct in accordance with this example of the DNA construct may comprise a nucleic acid comprising or consisting of the DNA sequence set forth in SEQ ID NO: 64 (shmiR13), and a nucleic acid comprising or consisting of the DNA sequence set forth in SEQ ID NO: 68 (shmiR17).

An exemplary ddRNAi construct encoding shmiR3 and shmiR14 for inclusion in a DNA construct of the disclosure comprises a nucleic acid comprising or consisting of a DNA sequence encoding a shmiR comprising an effector sequence set forth in SEQ ID NO: 17 and an effector complement sequence which is substantially complementary to the sequence set forth in SEQ ID NO: 17 e.g., an effector complement sequence set forth in SEQ ID NO: 16 (shmiR3), and a nucleic acid comprising or consisting of a DNA sequence encoding a shmiR comprising an effector sequence set forth in SEQ ID NO: 33 and an effector complement sequence which is substantially complementary to the sequence set forth in SEQ ID NO: 33 e.g., an effector complement sequence set forth in SEQ ID NO: 34 (shmiR14). For example, the ddRNAi construct in accordance with this example of the DNA construct may comprise a nucleic acid comprising or consisting of the DNA sequence set forth in SEQ ID NO: 57 (shmiR3), and a nucleic acid comprising or consisting of the DNA sequence set forth in SEQ ID NO: 65 (shmiR14).

Whilst certain examples have been described, it will be appreciated that a DNA construct in accordance with the present disclosure may include any ddRNAi construct described herein encoding one or more shmiRs. For example, ddRNAi constructs encoding shmiRs described in Examples 1 to 5 may be particularly suitable for inclusion in a DNA construct of the disclosure.

Compositions and Carriers

In some examples, the nucleic acid(s), ddRNAi construct(s) or expression vector(s) of the disclosure is/are provided in a composition. In some examples, a nucleic acid encoding a functional PABPN1 protein of the disclosure is provided in a composition. In some example, the nucleic acid(s), ddRNAi construct(s) or expression vector(s) of the disclosure is/are provided in a composition together with a nucleic acid encoding a functional PABPN1 protein of the disclosure. In some examples, the one or more nucleic acid(s) or ddRNAi construct(s) and the nucleic acid encoding a functional PABPN1 protein are provided in the same expression vector within a composition.

As described herein, the expression vector may comprise a ddRNAi construct of the disclosure alone or in combination with a codon-optimised nucleic acid encoding the functional PABPN1 protein of the disclosure. Reference herein to an expression vector and/or a composition comprising same will therefore be understood to encompass: (i) an expression vector comprising a ddRNAi construct of the disclosure, or a composition comprising same; (ii) an expression vector comprising both of a ddRNAi construct of the disclosure and a codon-optimised nucleic acid encoding the functional PABPN1 protein of the disclosure, or a composition comprising same; or (iii) an expression vector comprising a codon-optimised nucleic acid encoding the functional PABPN1 protein of the disclosure, or a composition comprising same.

Accordingly, a composition of the disclosure may comprise (i) an expression vector comprising a ddRNAi construct of the disclosure, and (ii) an expression vector comprising a codon-optimised nucleic acid encoding the functional PABPN1 protein of the disclosure. Alternatively, a composition of the disclosure may comprise a single expression vector comprising ddRNAi construct of the disclosure and a codon-optimised nucleic acid encoding the functional PABPN1 protein of the disclosure.

In yet another example, an expression vector comprising a ddRNAi construct of the disclosure may be provided in one composition and an expression vector comprising a codon-optimised nucleic acid encoding the functional PABPN1 protein of the disclosure may be provided within another composition e.g., which are packaged together.

A composition of the disclosure may also comprise one or more pharmaceutically acceptable carriers or diluents. For example, the composition may comprise a carrier suitable for delivery of the nucleic acid(s), ddRNAi construct(s), or expression vector(s) of the disclosure to muscle of a subject following administration thereto.

In some examples, the carrier is a lipid-based carrier, cationic lipid, or liposome nucleic acid complex, a liposome, a micelle, a virosome, a lipid nanoparticle or a mixture thereof.

In some examples, the carrier is a biodegradable polymer-based carrier, such that a cationic polymer-nucleic acid complex is formed. For example, the carrier may be a cationic polymer microparticle suitable for delivery of one or more nucleic acid(s), ddRNAi construct(s), or expression vector(s) of the disclosure to muscle cells or tissue of the eye. Use of cationic polymers for delivery compositions to cells is known in the art, such as described in Judge et al. *Nature* 25: 457-462 (2005), the contents of which is incorporated herein by reference. An exemplary cationic polymer-based carrier is a cationic DNA binding polymer, such as polyethylenimine. Other cationic polymers suitable for complexing with, and delivery of nucleic acid(s), ddRNAi construct(s), or expression vector(s) of the disclosure include poly(L-lysine) (PLL), chitosan, PAMAM dendrimers, and poly(2-dimethylamino)ethyl methacrylate (pD-MAEMA). Other polymers include poly beta-amino esters. These are other suitable cationic polymers are known in the art and are described in Mastrobattista and Hennink, *Nature Materials*, 11:10-12 (2012), WO/2003/097107 and WO/2006/041617, the full contents of which are incorporated herein by reference. Such carrier formulations have been developed for various delivery routes including parenteral subcutaneous injection, intravenous injection and inhalation.

In a further example, the carrier is a cyclodextrin-based carrier such as a cyclodextrin polymer-nucleic acid complex.

In a further example, the carrier is a protein-based carrier such as a cationic peptide-nucleic acid complex.

In another example, the carrier is a lipid nanoparticle. Exemplary nanoparticles are described, for example, in U.S. Pat. No. 7,514,099.

In some examples, the nucleic acid(s), ddRNAi construct(s), or expression vector(s) of the disclosure is/are formulated with a lipid nanoparticle composition comprising a cationic lipid/Cholesterol/PEG-C-DMA/DSPC (e.g., in a 40/48/2/10 ratio), a cationic lipid/Cholesterol/PEG-DMG/DSPC (e.g., in a 40/48/2/10 ratio), or a cationic lipid/Cholesterol/PEG-DMG (e.g., in a 60/38/2 ratio). In some examples, the cationic lipid is Octyl CL in DMA, DL in DMA, L-278, DLinKC2DMA, or MC3.

In another example, the nucleic acid(s), ddRNAi construct(s), or expression vector(s) of the disclosure is/are formulated with any of the cationic lipid formulations described in WO 2010/021865; WO 2010/080724; WO 2010/042877; WO 2010/105209 or WO 2011/022460.

In another example, the nucleic acid(s) or ddRNAi construct(s), or expression vector(s) of the disclosure is/are conjugated to or complexed with another compound, e.g., to facilitate delivery of the nucleic acid(s), ddRNAi construct(s), or expression vector(s). Non-limiting, examples of such conjugates are described in US 2008/0152661 and US 2004/0162260 (e.g., CDM-LBA, CDM-Pip-LBA, CDM-PEG, CDM-NAG, etc.).

In another example, polyethylene glycol (PEG) is covalently attached to a RNA or ddRNAi or expression vector of the disclosure. The attached PEG can be any molecular weight, e.g., from about 100 to about 50,000 daltons (Da).

In yet other example, the nucleic acid(s), ddRNAi construct(s), or expression vector(s) of the disclosure is/are formulated with a carrier comprising surface-modified liposomes containing poly(ethylene glycol) lipids (PEG-modified, or long-circulating liposomes or stealth liposomes), such as is disclosed in for example, WO 96/10391; WO 96/10390; or WO 96/10392.

In some examples, the nucleic acid(s), ddRNAi construct(s), or expression vector(s) of the disclosure can also be formulated or complexed with polyethyleneimine or a derivative thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives.

In other examples, the nucleic acid(s), ddRNAi construct(s), or expression vector(s) of the disclosure is/are complexed with membrane disruptive agents such as those described in U.S. Patent Application Publication No. 2001/0007666.

Other carriers include cyclodextrins (see for example, Gonzalez et al., 1999, *Bioconjugate Chem.*, 10, 1068-1074; or WO 03/46185), poly(lactic-co-glycolic)acid (PLGA) and PLCA microspheres (see for example US 2002130430).

Compositions will desirably include materials that increase the biological stability of the nucleic acid(s), ddRNAi construct(s), or expression vector(s) of the disclosure and/or materials that increase the ability of the compositions to localise to and/or penetrate muscle cells selectively. The therapeutic compositions of the disclosure may be administered in pharmaceutically acceptable carriers (e.g., physiological saline), which are selected on the basis of the mode and route of administration, and standard pharmaceutical practice. One having ordinary skill in the art can readily formulate a pharmaceutical composition that comprises one or more nucleic acid(s), ddRNAi construct(s), or expression vector(s) of the disclosure. In some cases, an isotonic formulation is used. Generally, additives for isotonicity can include sodium chloride, dextrose, mannitol, sorbitol and lactose. In some cases, isotonic solutions such as phosphate buffered saline are preferred. Stabilizers include gelatin and albumin. In some examples, a vasoconstriction agent is added to the formulation. The compositions according to the present disclosure are provided sterile and pyrogen free. Suitable pharmaceutical carriers, as well as pharmaceutical necessities for use in pharmaceutical formulations, are described in Remington: The Science and Practice of Pharmacy (formerly Remington's Pharmaceutical Sciences), Mack Publishing Co., a standard reference text in this field, and in the USP/NF.

The volume, concentration, and formulation of the pharmaceutical composition, as well as the dosage regimen may be tailored specifically to maximize cellular delivery while minimizing toxicity such as an inflammatory response e.g, relatively large volumes (5, 10, 20, 50 ml or more) with corresponding low concentrations of active ingredients, as well as the inclusion of an anti-inflammatory compound such as a corticosteroid, may be utilized if desired.

Compositions of the disclosure may be formulated for administration by any suitable route. For example, routes of administration include, but are not limited to, intramuscular, intraperitoneal, intradermal, subcutaneous, intravenous, intraarterially, intraocularly and oral as well as transdermal or by inhalation or suppository. Exemplary routes of administration include intravenous (IV), intramuscular (IM), oral, intraperitoneal, intradermal, intraarterial and subcutaneous injection. In one example, the composition of the disclosure is formulated for IM administration. Such compositions are useful for pharmaceutical applications and may readily be formulated in a suitable sterile, non-pyrogenic vehicle, e.g., buffered saline for injection, for parenteral administration e.g., IM, intravenously (including intravenous infusion), SC, and for intraperitoneal administration. Some routes of administration, such as IM, IV injection or infusion, may achieve effective delivery to muscle tissue and transfection of a ddRNAi constructs and/or codon-optimised nucleic acids encoding PABPN1 of the disclosure, and expression of RNA and/or the codon-optimised nucleic acid therein.

Methods of Treatment

In one example, one or more nucleic acid(s), ddRNAi construct(s), expression vector(s) or composition(s) comprising same as described herein be used for inhibiting expression of endogenous PABPN1 protein, including a PABPN1 protein which is causative of OPMD, in a subject.

In one example, one or more nucleic acid(s), ddRNAi construct(s), expression vector(s) or composition(s) comprising same as described herein may be used to treat OPMD in a subject suffering therefrom. Similarly, one or more nucleic acid(s), ddRNAi construct(s), expression vector(s) or composition(s) comprising same as described herein may be used to prevent the development or progression of one or more symptoms of OPMD in a subject suffering therefrom or predisposed thereto.

In each of the foregoing examples, the expression vector and/or composition of the disclosure may comprise both a ddRNAi construct of the disclosure and a codon-optimised nucleic acid encoding functional PABPN1 protein of the disclosure. Accordingly, administration of the expression vector or composition may be effective to (i) inhibit, reduce or knockdown expression of endogenous PABPN1, including the PABPN1 protein comprising an expanded polyalanine tract which is causative of OPMD, and (ii) provide for expression of a functional PABPN1 protein which is not targeted by shmiRs or shRNAs which inhibit, reduce or knockdown expression of endogenous PABPN1. A composition of the disclosure may thus restore PABPN1 protein function e.g., post-transcriptional processing of RNA, in a cell or animal to which it is administered.

In another example, treatment of OPMD may comprise administering separately to a subject (i) one or more agents for inhibiting expression of a PABPN1 protein which is causative of OPMD, and (ii) an expression vector comprising a codon-optimised nucleic acid encoding functional PABPN1 protein of the disclosure or composition comprising same. As described herein, the one or more agents for inhibiting expression of a PABPN1 protein which is causative of OPMD may be a nucleic acid, a ddRNAi construct, an expression vector or composition comprising same as described herein or a plurality of any one or more thereof. The subject may be administered components (i) and (ii) together, simultaneously or consecutively.

For example, treatment of OPMD may comprise administering to a subject a codon-optimised nucleic acid encoding a functional PABPN1 protein of the disclosure, wherein the subject has previously been administered one or more agents for inhibiting expression of a PABPN1 protein which is causative of OPMD but which does not inhibit expression of the codon-optimised nucleic acid. For example, the subject may have been previously administered a nucleic acid, a ddRNAi construct, an expression vector or composition comprising same as described herein or a plurality of any one or more thereof.

As discussed above, routes of administration include, but are not limited to, intramuscular, intraperitoneal, intradermal, subcutaneous, intravenous, intraarterially, intraocularly and oral as well as transdermal or by inhalation or suppository. Exemplary routes of administration include intravenous (IV), intramuscular (IM), oral, intraperitoneal, intradermal, intraarterial and subcutaneous injection. Some routes of administration, such as IM, IV injection or infusion, may achieve effective delivery to muscle tissue and transfection of a ddRNAi constructs and/or codon-optimised nucleic acids encoding PABPN1 of the disclosure, and expression of shmiRs or shRNA and/or the codon-optimised nucleic acid therein.

One skilled in the art would be able, by routine experimentation, to determine an effective, non-toxic amount of a nucleic acid, a ddRNAi construct, an expression vector or composition comprising same as described herein, or a plurality of any one or more thereof, which would be required to treat a subject suffering from OPMD. The therapeutically effective dose level for any particular patient will depend upon a variety of factors including: the composition employed; the age, body weight, general health, sex and diet of the patient; the time of administration; the route of administration; the rate of sequestration of the nucleic acid, a ddRNAi construct, an expression vector or composition comprising same as described herein, or a plurality of any one or more thereof, the duration of the treatment, together with other related factors well known in medicine.

Efficacy of a nucleic acid, a ddRNAi construct, an expression vector or composition comprising same of the disclosure to reduce or inhibit expression of the PABPN1 protein causative of OPMD and to express functional PABPN1 protein which is not causative of OPMD in an amount sufficient to restore PABPN1 function, may be determined by evaluating muscle contractile properties and/or swallowing difficulties in the subject treated. Methods for testing swallowing ability and muscle contractile properties are known in the art. For example, swallowing difficulties may be evaluated using videofluoroscopy, UGI endoscopy or oesophageal manometry and impedance testing. Other methods for assessing clinical features of OPMD are described in Ruiegg et al, (2005) *Swiss Medical Weekly*, 135:574-586.

Kits

The present disclosure also provides one or more nucleic acid(s), ddRNAi construct(s), expression vector(s) or composition comprising same of the disclosure in the form of a kit. The kit may comprise a container. The kit typically contains one or more nucleic acid(s), ddRNAi construct(s), expression vector(s) or composition comprising same of the disclosure with instructions for its, or their, administration. In some examples, the kit contains more than one nucleic acid, ddRNAi construct, expression vector or composition comprising same of the disclosure. In one example, the kit comprises (i) a first kit component for reducing or inhibiting expression of a PABPN1 protein causative of OPMD, comprising one or more nucleic acid(s), ddRNAi construct(s), expression vector(s) or composition comprising same of the disclosure, and (ii) an expression vector comprising a codon-optimised nucleic acid encoding the functional PABPN1 protein of the disclosure or composition comprising same, as a second kit component. The first and second kit components may be packaged together in a kit.

TABLE 1

Targeted regions in PABPN1

| Region ID | Region sequence (5'-3') | SEQ ID NO: |
|---|---|---|
| Region 2 | GAGAAGCAGAUGAAUAUGAGUCCACCUC | SEQ ID NO: 1 |
| Region 3 | GAACGAGGUAGAGAAGCAGAUGAAUAUG | SEQ ID NO: 2 |
| Region 4 | GAAGCUGAGAAGCUAAAGGAGCUACAGA | SEQ ID NO: 3 |
| Region 5 | GGGCUAGAGCGACAUCAUGGUAUUCCCC | SEQ ID NO: 4 |
| Region 6 | CUGUGUGACAAAUUUAGUGGCCAUCCCA | SEQ ID NO: 5 |
| Region 7 | GACUAUGGUGCAACAGCAGAAGAGCUGG | SEQ ID NO: 6 |
| Region 9 | CGAGGUAGAGAAGCAGAUGAAUAUGAGU | SEQ ID NO: 7 |
| Region 11 | CAGUGGUUUUAACAGCAGGCCCCGGGGU | SEQ ID NO: 8 |
| Region 13 | AGAGCGACAUCAUGGUAUUCCCCUUACU | SEQ ID NO: 9 |
| Region 14 | GGUAGAGAAGCAGAUGAAUAUGAGUCCA | SEQ ID NO: 10 |
| Region 15 | AUUGAGGAGAAGAUGGAGGCUGAUGCCC | SEQ ID NO: 11 |
| Region 16 | GGAGGAAGAAGCUGAGAAGCUAAAGGAG | SEQ ID NO: 12 |
| Region 17 | AACGAGGUAGAGAAGCAGAUGAAUAUGA | SEQ ID NO: 13 |

TABLE 2 shmiR effector and effector complement sequences

| shmiR ID | Effector complement sequence (5'-3') | SEQ ID NO: | Effector sequence (5'-3') | SEQ ID NO: |
|---|---|---|---|---|
| shmiR2 | AGCAGAUGAA UAUGAGUCCA | SEQ ID NO: 14 | UGGACUCAUAU UCAUCUGCUU | SEQ ID NO: 15 |
| shmiR3 | GAGGUAGAGA AGCAGAUGAA | SEQ ID NO: 16 | UUCAUCUGCUU CUCUACCUCG | SEQ ID NO: 17 |
| shmiR4 | CUGAGAAGCU AAAGGAGCUA | SEQ ID NO: 18 | UAGCUCCUUUA GCUUCUCAGC | SEQ ID NO: 19 |
| shmiR5 | UAGAGCGACA UCAUGGUAUU | SEQ ID NO: 20 | AAUACCAUGAU GUCGCUCUAG | SEQ ID NO: 21 |
| shmiR6 | GUGACAAAUU UAGUGGCCAU | SEQ ID NO: 22 | AUGGCCACUAA AUUUGUCACA | SEQ ID NO: 23 |
| shmiR7 | AUGGUGCAAC AGCAGAAGAG | SEQ ID NO: 24 | CUCUUCUGCUG UUGCACCAUA | SEQ ID NO: 25 |
| shmiR9 | GUAGAGAAGC AGAUGAAUAU | SEQ ID NO: 26 | AUAUUCAUCUG CUUCUCUACC | SEQ ID NO: 27 |
| shmiR11 | GGUUUUAACA GCAGGCCCCG | SEQ ID NO: 28 | CGGGGCCUGCU GUUAAAACCA | SEQ ID NO: 29 |
| shmiR13 | CGACAUCAUG GUAUUCCCCU | SEQ ID NO: 30 | AGGGGAAUACC AUGAUGUCGC | SEQ ID NO: 31 |
| shmiR14 | GAGAAGCAGA UGAAUAUGAG | SEQ ID NO: 32 | CUCAUAUUCAU CUGCUUCUCU | SEQ ID NO: 33 |
| shmiR15 | AGGAGAGAU GGAGGCUGAU | SEQ ID NO: 34 | AUCAGCCUCCA UCUUCUCCUC | SEQ ID NO: 35 |
| shmiR16 | GAAGAAGCUG AGAAGCUAAA | SEQ ID NO: 36 | UUUAGCUUCUC AGCUUCUUCC | SEQ ID NO: 37 |
| shmiR17 | AGGUAGAGAA GCAGAUGAAU | SEQ ID NO: 38 | AUUCAUCUGCU UCUCUACCUC | SEQ ID NO: 39 |

TABLE 3 shmiR sequences

| shmiR | shmiR sequences (5'-3') | SEQ ID NO: |
|---|---|---|
| shmiR2 | GGUAUAUUGCUGUUGACAGUGAGCGUAGCAGAU GAAUAUGAGUCCAACUGUGAAGCAGAUGGGUUG GACUCAUAUUCAUCUGCUUCGCCUACUGCCUCG GACUUCAA | SEQ ID NO: 43 |
| shmiR3 | GGUAUAUUGCUGUUGACAGUGAGCGAGAGGUAG AGAAGCAGAUGAAACUGUGAAGCAGAUGGGUUU CAUCUGCUUCUCUACCUCGCGCCUACUGCCUCG GACUUCAA | SEQ ID NO: 44 |
| shmiR4 | GGUAUAUUGCUGUUGACAGUGAGCGACUGAGAA GCUAAAGGAGCUAACUGUGAAGCAGAUGGGUUA GCUCCUUUAGCUUCUCAGCCGCCUACUGCCUCG GACUUCAA | SEQ ID NO: 45 |
| shmiR5 | GGUAUAUUGCUGUUGACAGUGAGCGAUAGAGCG ACAUCAUGGUAUUACUGUGAAGCAGAUGGGUAA UACCAUGAUGUCGCUCUAGCGCCUACUGCCUCG GACUUCAA | SEQ ID NO: 46 |
| shmiR6 | GGUAUAUUGCUGUUGACAGUGAGCGAGUGACAA AUUUAGUGGCCAUACUGUGAAGCAGAUGGGUAU GGCCACUAAAUUUGUCACACGCCUACUGCCUCG GACUUCAA | SEQ ID NO: 47 |
| shmiR7 | GGUAUAUUGCUGUUGACAGUGAGCGAAUGGUGC AACAGCAGAAGAGACUGUGAAGCAGAUGGGUCU CUUCUGCUGUUGCACCAUACGCCUACUGCCUCG GACUUCAA | SEQ ID NO: 48 |
| shmiR9 | GGUAUAUUGCUGUUGACAGUGAGCGAGUAGAGA AGCAGAUGAAUAUACUGUGAAGCAGAAUGGGUA UAUUCAUCUGCUUCUCUACCCGCCUACUGCCUC GGACUUCAA | SEQ ID NO: 49 |
| shmiR11 | GGUAUAUUGCUGUUGACAGUGAGCGAGGUUUUA ACAGCAGGCCCCGACUGUGAAGCAGAUGGGUUCG GGGCCUGCUGUUAAAACCACGCCUACUGCCUCG GACUUCAA | SEQ ID NO: 50 |
| shmiR13 | GGUAUAUUGCUGUUGACAGUGAGCGACGACAUC AUGGUAUUCCCUACUGUGAAGCAGAUGGGUAG GGGAAUACCAUGAUGUCGCCGCCUACUGCCUCG GACUUCAA | SEQ ID NO: 51 |
| shmiR14 | GGUAUAUUGCUGUUGACAGUGAGCGUGAGAAGC AGAUGAAUAUGAGACUGUGAAGCAGAUGGGUCU CAUAUUCAUCUGCUUCUCUCGCCUACUGCCUCG GACUUCAA | SEQ ID NO: 52 |
| shmiR15 | GGUAUAUUGCUGUUGACAGUGAGCGAAGGAGAA GAUGGAGGCUGAUACUGUGAAGCAGAUGGGUAU CAGCCUCCAUCUUCUCCUCCGCCUACUGCCUCG GACUUCAA | SEQ ID NO: 53 |
| shmiR16 | GGUAUAUUGCUGUUGACAGUGAGCGAGAAGAAG CUGAGAAGCUAAAACUGUGAAGCAGAUGGGUUU UAGCUUCUCAGCUUCUUCCCGCCUACUGCCUCG GACUUCAA | SEQ ID NO: 54 |
| shmiR17 | GGUAUAUUGCUGUUGACAGUGAGCGAAGGUAGA GAAGCAGAUGAAUAUACUGUGAAGCAGAUGGGUAU UCAUCUGCUUCUCUACCUCCGCCUACUGCCUCG GACUUCAA | SEQ ID NO: 55 |

TABLE 4

Shmir encoding cassettes

| shmiR | Shmir encoding cassettes (5'-3') | SEQ ID NO: |
|---|---|---|
| shmiR2 | GGTATATTGCTGTTGACAGTGAGCGTAGCAGAT GAATATGAGTCCAACTGTGAAGCAGATGGGTTG GACTCATATTCATCTGCTTCGCCTACTGCCTCG GACTTCAA | SEQ ID NO: 56 |
| shmiR3 | GGTATATTGCTGTTGACAGTGAGCGAGAGGTAG AGAAGCAGATGAAACTGTGAAGCAGATGGGTTT CATCTGCTTCTCTACCTCGCGCCTACTGCCTCG GACTTCAA | SEQ ID NO: 57 |
| shmiR4 | GGTATATTGCTGTTGACAGTGAGCGACTGAGAA GCTAAAGGAGCTAACTGTGAAGCAGATGGGTTA GCTCCTTTAGCTTCTCAGCCGCCTACTGCCTCG GACTTCAA | SEQ ID NO: 58 |
| shmiR5 | GGTATATTGCTGTTGACAGTGAGCGATAGAGCG ACATCATGGTATTACTGTGAAGCAGATGGGTAA TACCATGATGTCGCTCTAGCGCCTACTGCCTCG GACTTCAA | SEQ ID NO: 59 |

TABLE 4-continued

Shmir encoding cassettes

| shmiR | Shmir encoding cassettes (5'-3') | SEQ ID NO: |
|---|---|---|
| shmiR6 | GGTATATTGCTGTTGACAGTGAGCGAGTGACAA<br>ATTTAGTGGCCATACTGTGAAGCAGATGGGTAT<br>GGCCACTAAATTTGTCACACGCCTACTGCCTCG<br>GACTTCAA | SEQ ID NO: 60 |
| shmiR7 | GGTATATTGCTGTTGACAGTGAGCGAATGGTGC<br>AACAGCAGAAGAGACTGTGAAGCAGATGGGTCT<br>CTTCTGCTGTTGCACCATACGCCTACTGCCTCG<br>GACTTCAA | SEQ ID NO: 61 |
| shmiR9 | GGTATATTGCTGTTGACAGTGAGCGAGTAGAGA<br>AGCAGATGAATATACTGTGAAGCAGATGGGTAT<br>ATTCATCTGCTTCTCTACCCGCCTACTGCCTCG<br>GACTTCAA | SEQ ID NO: 62 |
| shmiR11 | GGTATATTGCTGTTGACAGTGAGCGAGGTTTTA<br>ACAGCAGGCCCCGACTGTGAAGCAGATGGGTCG<br>GGGCCTGCTGTTAAAACCACGCCTACTGCCTCG<br>GACTTCAA | SEQ ID NO: 63 |
| shmiR13 | GGTATATTGCTGTTGACAGTGAGCGACGACATC<br>ATGGTATTCCCCTACTGTGAAGCAGATGGGTAG<br>GGGAATACCATGATGTCGCCGCCTACTGCCTCG<br>GACTTCAA | SEQ ID NO: 64 |
| shmiR14 | GGTATATTGCTGTTGACAGTGAGCGTGAGAAGC<br>AGATGAATATGAGACTGTGAAGCAGATGGGTCT<br>CATATTCATCTGCTTCTCTCGCCTACTGCCTCG<br>GACTTCAA | SEQ ID NO: 65 |
| shmiR15 | GGTATATTGCTGTTGACAGTGAGCGAAGGAGAA<br>GATGGAGGCTGATACTGTGAAGCAGATGGGTAT<br>CAGCCTCCATCTTCTCCTCCGCCTACTGCCTCG<br>GACTTCAA | SEQ ID NO: 66 |
| shmiR16 | GGTATATTGCTGTTGACAGTGAGCGAGAAGAAG<br>CTGAGAAGCTAAAACTGTGAAGCAGATGGGTTT<br>TAGCTTCTCAGCTTCTTCCCGCCTACTGCCTCG<br>GACTTCAA | SEQ ID NO: 67 |
| shmiR17 | GGTATATTGCTGTTGACAGTGAGCGAAGGTAGA<br>GAAGCAGATGAATACTGTGAAGCAGATGGGTAT<br>TCATCTGCTTCTCTACCTCCGCCTACTGCCTCG<br>GACTTCAA | SEQ ID NO: 68 |

Example 1—Design of shmiRs Targeting PABN1

Sequences representing potential targets for design of siRNA constructs were identified from the PABPN1 mRNA sequence using publicly available siRNA design algorithms (including Ambion, Promega, Invitrogen, Origene and MWG): the selected sequences were conserved in humans, non-human primates, bovine and mice species. Sequences encoding the candidate siRNAs were incorporated into a pre-miR30a scaffold in order to create a sequence encoding a short-hairpin microRNA (shmiR) comprising a 5' flanking region (SEQ ID NO: 41), a siRNA sense strand sequence (effector complement sequence), a stem/loop junction sequence (SEQ ID NO: 40), a siRNA anti-sense strand (effector sequence), and a 3' flanking region (SEQ ID NO:42). The predicted secondary structure of a representative shmiR is shown in FIG. 1. The target regions of the PABPN1 mRNA transcript for the designed shmiRs are presented in Table 1 and corresponding shmiR effector sequences (antisense strand) are presented in Table 2.

Example 2—Activity of shmiRs in Dual-Luciferase Reporter Assay

To test the efficacy of the shmiRs of the disclosure to knockdown expression of PABPN1 transcripts, dual-luciferase reporter assays were performed in HEK293 cells.

pGL3 Luciferase reporter vectors were constructed. The Luciferase reporters were generated by inserting the complete coding sequence of either wild-type or codon-optimised PABPN1 (wtPABPN1 or optPABPN1) into the pGL3-control vector (Promega, Madison, Wis.). The inserts were subcloned into the 3' UTR of the luciferase reporter gene using FseI and XbaI restriction enzyme sites. Constructs containing the PABPN1 targeting shmiR sequences (listed in Table 3), driven by the U6 pol III promoter, were synthesized at DNA2.0 (Newark, Calif.) and subcloned into the pSilencer plasmid backbone.

The HEK293 cell line was purchased from ATCC (Manassas, Va.). HEK293 cells were cultured in DMEM medium containing 10% fetal bovine serum, 2 mM glutamine, penicillin (100 U/mL), and streptomycin (100 μg/mL) at 37° C. humid incubator with 5% CO2. Briefly, the HEK293 cell were seeded at a density of $2 \times 10^4$ cells per well into 96-well culture plate one day prior to transfection.

The PABPN1 shmiR-expressing constructs and their corresponding antisense or sense Luciferase reporter and Renilla control reporter constructs were co-transfected into HEK293 cells using Fugene 6 (Promega, Madison, Wis.) according to manufacturer's instructions. For each well of transfection, 100 ng of one of the PABPN1 shmiRs, 10 ng of the corresponding Luciferase reporter construct and Ing of Renilla control reporter construct (served as transfection control) were co-transfected using 0.3 uL of Fugene 6. 48 hour post-transfection, cell lysates were collected and analyzed using Dual Luciferase Reporter Assay System (Promega, Madison, Wis.). The firefly/Renilla activity ratios were determined for each well, and the inhibition efficiency of shmiRs were calculated by normalizing to a non-targeting siRNA, pSilencer control (Thermo Fisher, USA). Percent inhibition of wtPABPN1 or optPABPN1 reporter constructs in HEK293 cells for the sense and antisense strands of each of the shmiRs relative to the psilencer control are illustrated in FIGS. 2 and 3.

Figure 2:
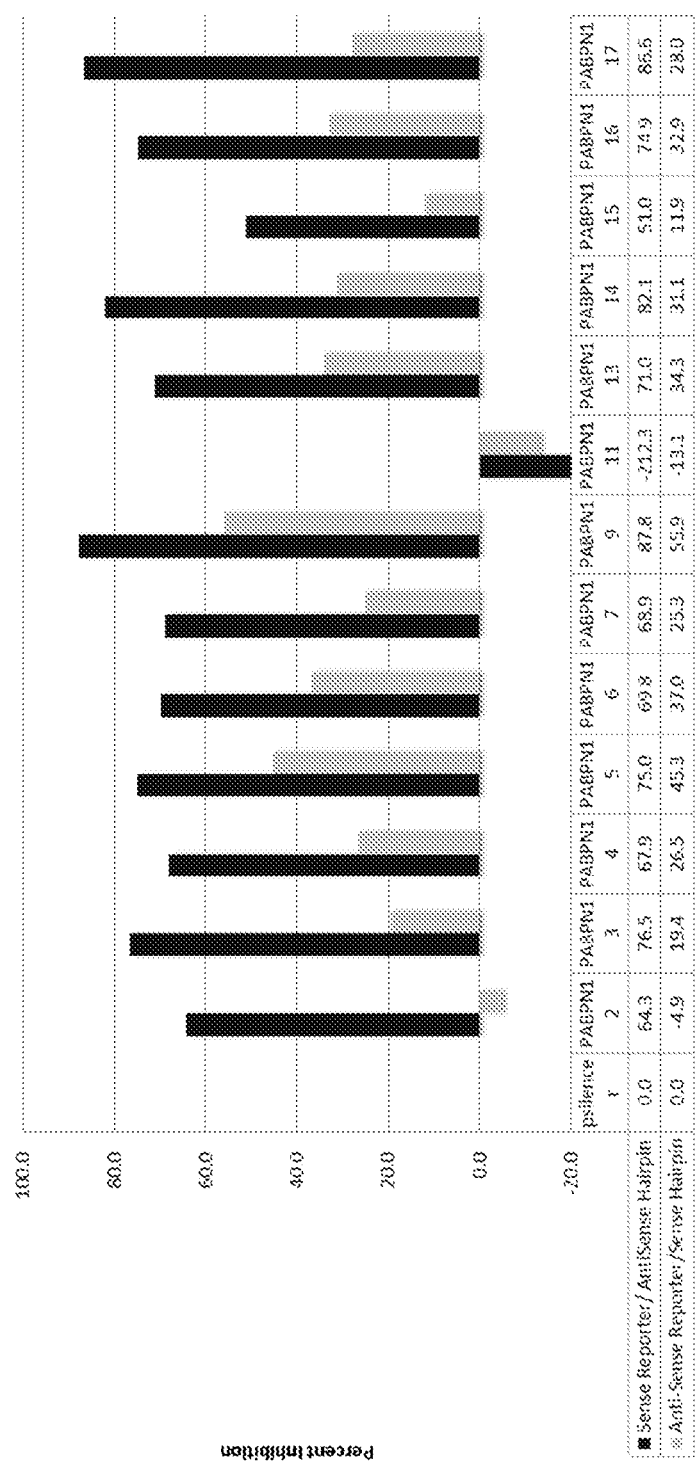
FIG. 2 illustrates the wtPABPN1 inhibitory activity of shmiRs having antisense and sense sequences of shmiRs designated shmiR2-17 relative to the psilencer control in HEK293 cells. This graph illustrates that all shmiRs except shmiR11 downregulated the level of luciferase expression from the wtPABPN1 Luciferase reporter.
Figure 3:
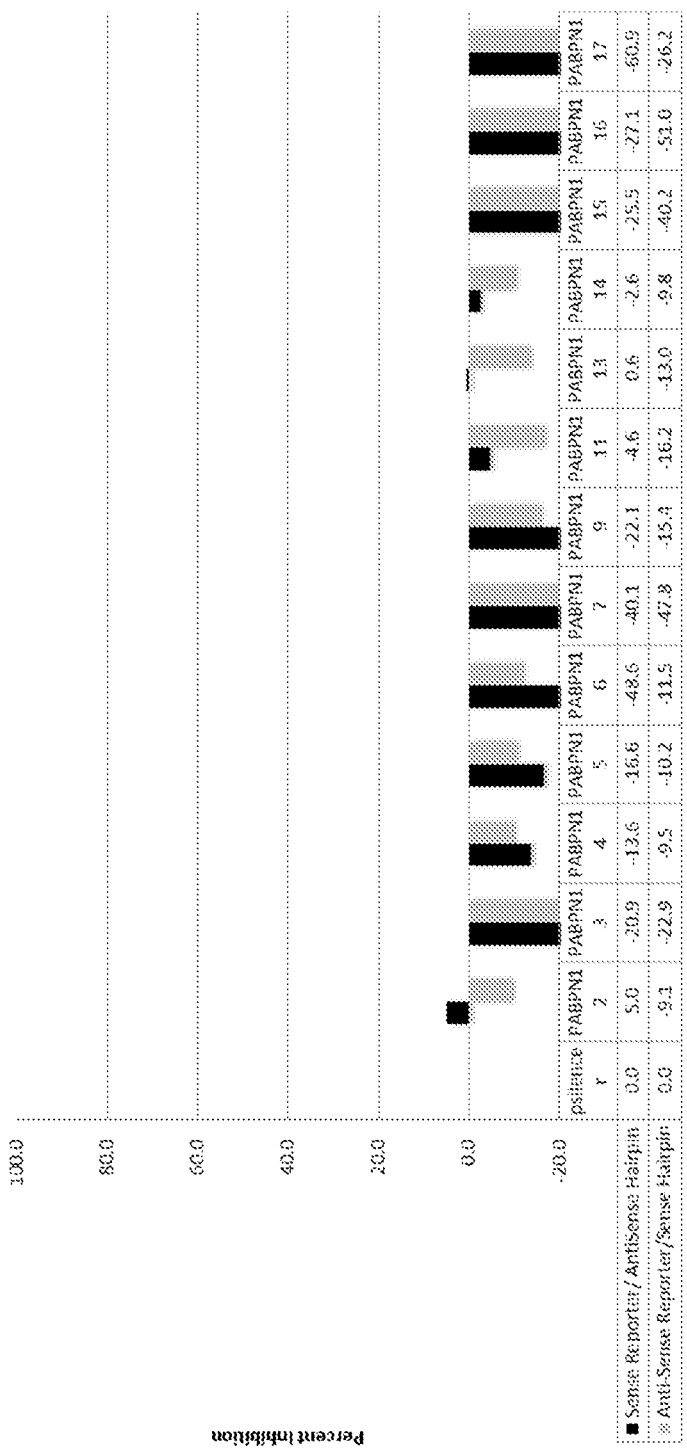
FIG. 3 illustrates the optPABPN1 inhibitory activity of shmiRs having antisense and sense sequences of shmiRs designated shmiR 2-17 relative to the psilencer control in HEK293 cells. This graph illustrates that there was no downregulation of expression from the optPABPN1 Luciferase reporter.

As is evident in FIGS. 2 and 3, all except one of the exemplary shmiRs (shmiR11) designated in Table 2 downregulated the level of luciferase expressed from the wtPABPN1 Luciferase reporter vector (FIG. 2) but did not downregulate the expression from the coPABPN1 (FIG. 3) reporter. In particular, shmiR-3, shmiR-4, shmiR-13, shmiR-14, shmiR-16, and shmiR-17 were shown to have potent inhibitory activity (defined as greater than 70% inhibition of luciferase activity relative to cells treated with an unrelated shRNA as a negative control) against the PABPN1 target mRNA sequences, while possessing weak activity (less than 35% inhibition) against their cognate reporters containing a target sequence recognised by the passenger strand.

Example 3—In Vitro Downregulation of PABPN1 Protein Expression

Based on the downregulation of PABPN1 expression measured by the Luciferase activity assay described above, shmiRs 2, 3, 5, 9, 13, 14, 16, and 17 were selected for further analysis. In order to examine their ability to downregulate PABPN1 in vitro, the shmiR containing plasmids driven by the U6 promoter described in example 2 were used along with two additional expression plasmids. One coding for a FLAG-tagged human wtPABPN1 (wt-PABPN1-FLAG; SEQ ID NO: 75), and the other comprising a codon-optimised sequence coding for human PABPN1 with a FLAG tag (co-PABPN1-FLAG; SEQ ID NO: 76).

Cells

Human embryonic kidney cells (HEK293T, ATCC, Manassas, USA) were grown in Dulbecco's modified Eagle's medium (DMEM) containing 20 mM HEPES, 2 mM glutamine, 10% foetal bovine serum (FBS), 1× Pen-strep.

Treatment

Briefly, HEK293T cells were seeded at 1×10$^6$ cells/well and transfected the next day with one of the shmiR plasmids described above (300 ng/well), with or without plasmids expressing wild-type human PABPN1 (wt-PABPN1-FLAG) (100 ng/well) (SEQ ID NO:75) or codon-optimized PABPN1 (co-PABPN1-FLAG) (100 ng/well) (SEQ ID NO:76). As a control, HEK293T cells were transfected with the pSilencer control plasmid expressing a non-targeting siRNA sequence (Thermo Fisher, USA). The HEK293T cells were incubated at 37° C. in complete DMEM media for 72 hours, after which time the cells were harvested and cell lysates were analyzed by Western blot.

Western Blot Analysis

Cell lysates were prepared by incubating cells in RIPA buffer containing: NaCl 0.15M, 0.1% SDS, 50 mM Tris (pH8), 2 mM EDTA and 10% Triton-X-100 with protease inhibitor cocktail (Complete, Roche Diagnostics).

Proteins were separated on 4-12% Bis-Tris gel (Invitrogen) and transferred to the nitrocellulose membrane using the iBlot 2 dry blotting system (Life Technologies). Blots were blocked and probed with primary and secondary antibodies using the iBind Western System (Invitrogen). Primary antibodies (anti-flag (GenScript) and anti-Hsp90 (Sigma)) were used at 1:500 dilution while secondary AP-conjugated antibodies (anti-mouse and anti-rabbit, Sigma) were used at 1:6000 dilutions. Bands were detected using DDAO dye and visualized using a FLA-3000 scanner (Fuji).

Figure 4:
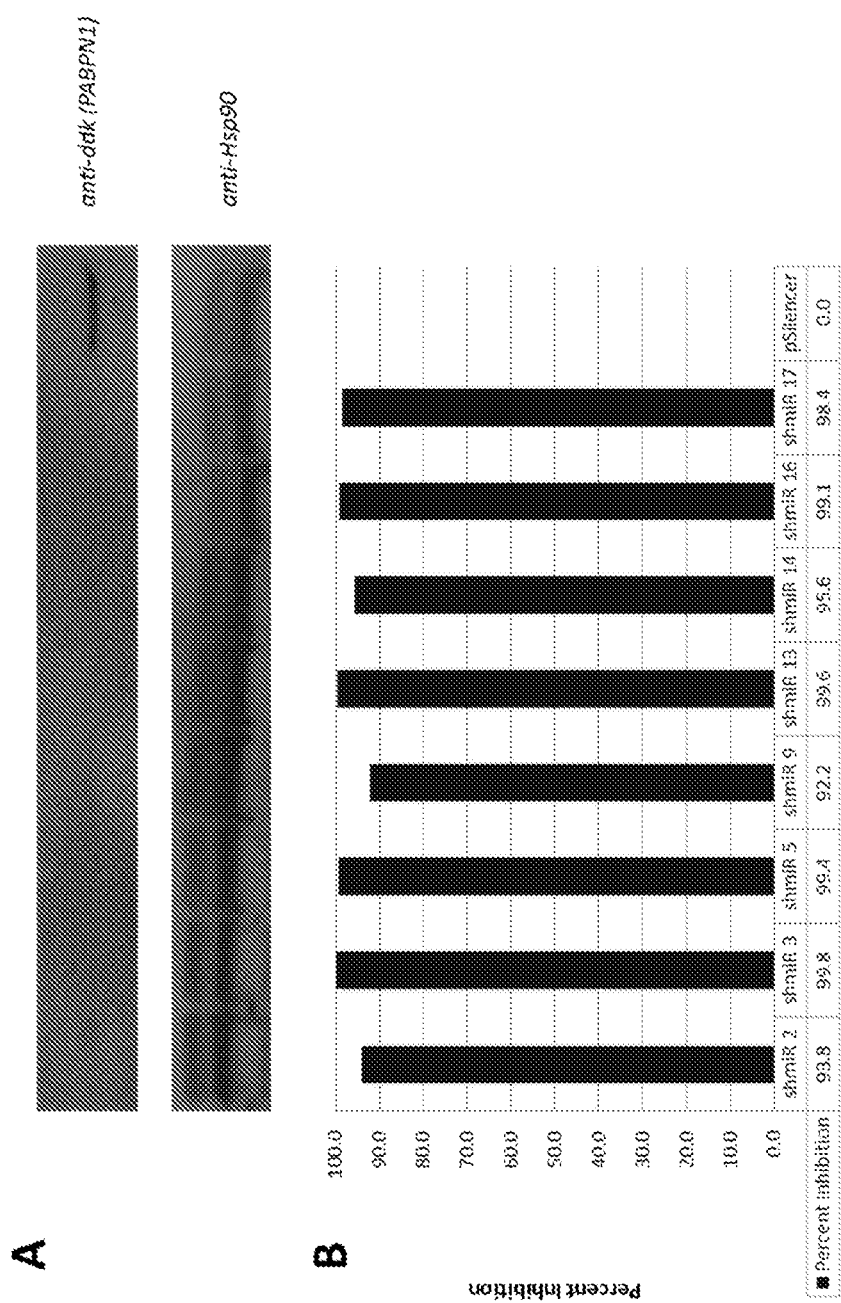
FIG. 4(A) is a western blot showing levels of FLAG-tagged wtPABPN1 protein relative to Hsp90 protein expressed in HEK293T cells transfected with plasmids encoding shmiR2, shmiR3, shmiR5, shmiR9, shmiR13, shmiR14, shmiR16 or shmiR17. This shows that all of the selected shmiRs knocked down the expression of wtPABPN1.
FIG. 4(B) illustrates the percent inhibition of FLAG-tagged wtPABPN1 protein in HEK293 cells relative to the psilencer control. This graph illustrates that all of the selected shmiRs knocked down the expression of wtPABPN1 with percent inhibition >90%, as determined by densiometric analysis of the western blot at FIG. 4(A).
Figure 5:
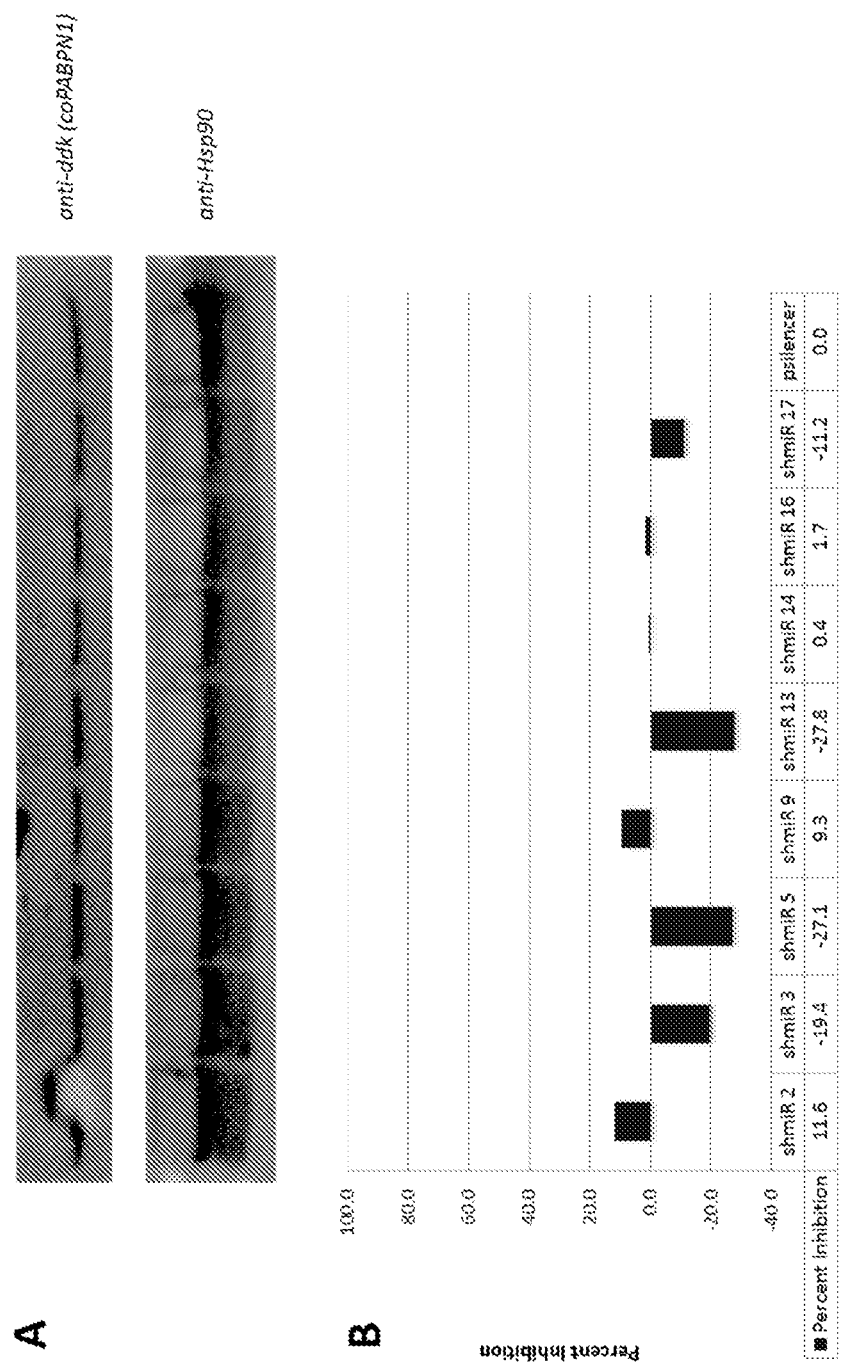
FIG. 5(A) is a western blot showing levels of FLAG-tagged codon-optimised PABPN1 protein relative to Hsp90 protein expressed in HEK293T cells transfected with shmiRs plasmids encoding shmiR2, shmiR3, shmiR5, shmiR9, shmiR13, shmiR14, shmiR16 or shmiR17. This shows that none of the shmiRs resulted in inhibition of the expression product of the codon-optimised PABPN1 construct.
FIG. 5(B) illustrates the percent inhibition of FLAG-tagged codon-optimised PABPN1 protein in HEK293 cells relative to the psilencer control. This graph illustrates that none of the shmiRs resulted in inhibition of the expression product of the codon-optimised PABPN1 construct, as determined by densiometric analysis of the western blot at FIG. 5(A).

The resulting blots and quantification of percent inhibition of PABPN1 expression relative to the control using ImageJ are shown in FIGS. 4 and 5. As is evidenced from FIG. 4, all of the selected shmiRs from Example 3 knocked down the expression of wild-type PABPN1 with percent inhibition >90%, and 7 of the 8 shmiRs tested inhibited expression of wild-type PABPN1 protein at levels of >95%. In contrast, the shmiRs did not inhibit the expression of the codon optimized PABPN1 construct (FIG. 5).

Example 4—shmiR Targeted Gene Silencing of PABPN1 in HEK293T Cells

This example demonstrates the ability of the PABPN1 shmiR plasmids to knockdown the endogenous expression of PABPN1 in vitro.

Cells

Human embryonic kidney cells (HEK293T, ATCC, Manassas, USA) were grown in Dulbecco's modified Eagle's medium (DMEM) containing 20 mM HEPES, 2 mM glutamine, 10% foetal bovine serum (FBS), 1× Pen-strep.

Treatment

Briefly, HEK293T cells were seeded at 1×10$^6$ cells/well and transfected the next day with one of the shmiR plasmids described in Example 2 (300 ng/well). As a control, HEK293T cells were transfected with the psilencer plasmid expressing a non-targeting siRNA sequence (Thermo Fisher, USA). The HEK293T cells were incubated at 37° C. in complete DMEM media for 72 hours, after which time the cells were harvested and RNA was extracted reverse transcribed and analyzed by qPCR.

qPCR Analysis qPCR analysis was performed on extracted RNA samples in order to quantify the level of inhibition of PABPN1 at the mRNA level by the shmiRs described above.

In order to differentiate the codon optimized PABPN1 from the wild-type PABPN1, TaqMan Primers and Probes were designed to specifically amplify wild-type PABPN1 or codon optimized PABPN1. Primers were designed using GenScript TaqMan primer design tool (https://www.genscript.com/ssl-bin/app/primer)

The resulting sequences of primers used for quantitative RT-PCR are as follows:

```
wtPABPN1-Fwd
                                (SEQ ID NO: 77)
5'-ATGGTGCAACAGCAGAAGAG-3' wtPABPN1-Rev
                                (SEQ ID NO: 78)
5'-CTTTGGGATGGCCACTAAAT-3' wtPABPN1-Probe
                                (SEQ ID NO: 79)
5'-CGGTTGACTGAACCACAGCCATG-3' optPABPN1-Fwd
                                (SEQ ID NO: 80)
5'-ACCGACAGAGGCTTCCCTA-3' opt5PABPN1-Rev
                                (SEQ ID NO: 81)
5'-TTCTGCTGCTGTTGTAGTTGG-3' optPABPN1-Probe
                                (SEQ ID NO: 82)
5'-TGGTCCGGGCTCTGTACCTAGCC-3'
```

Total RNA was extracted from cell lysates using Trizol (Invitrogen) according to the manufacturer's instructions. RNA samples were quantified using a ND-1000 NanoDrop spectrophotometer (NanoDrop Technologies). RNA (100 ng) was reverse transcribed using Multiscribe reverse transcriptase (ABI) according to the manufacturer's instructions. cDNA was used for quantitative PCR reaction using Taqman qPCR master mix in a total of 10 ul reaction volume. PCR reaction was carried out as follows: 2 minutes at 50° C., 10 minutes at 95° C. followed by 40 cycles: 15 seconds at 95° C., 1 minute at 60° C.

The expression level of each mRNA was normalized to GAPDH. Expression levels were calculated according to the total copies as determine by a standard curve and converted to percent inhibition relative to the pSilencer control.

Figure 6:
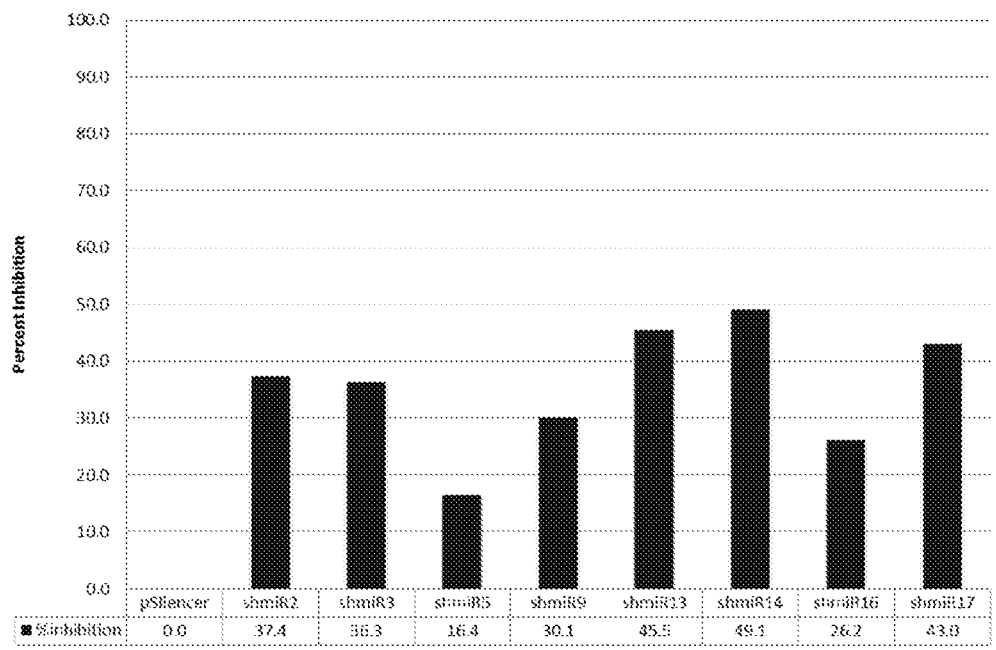
FIG. 6 illustrates the percent inhibition of endogenous wtPABPN1 expression in HEK293T cells by shmiR2, shmiR3, shmiR5, shmiR9, shmiR13, shmiR14, shmiR16 or shmiR17, as determined by qPCR analysis. This graph illustrates that the shmiRs downregulated the expression of wtPABPN1 with percent inhibition ranging between 16.4% to 49.1% (mean 35.5%).

The resulting percent inhibition of wild type PABPN1 expression in HEK293 cells by the exemplified shmiRs is presented in FIG. 6. As shown in FIG. 6, the shmiRs downregulated the expression of PABPN1 with percent inhibition ranging between 16.4% to 49.1% (mean 35.5%).

Example 5—shmiR Targeted Gene Silencing of PABPN1 in C2C12 Mouse Muscle Cells and ARPE-19 Human Retinal Cells In order to determine whether the low percent inhibition by the exemplified shmiRs on PABPN1 expression in HEK293 cells measured by qPCR was due to cell line variation in gene expression of PABPN1, additional cell lines were chosen for analysis which are relevant to OPMD, namely C2C12 mouse muscle and ARPE-19 human retinal cells.

Cells

C2C12 mouse muscle cells were grown in Dulbecco's modified Eagle's medium (DMEM) containing 20 mM HEPES, 2 mM glutamine, 10% foetal bovine serum (FBS), 1× Penstrep.

ARPE-19 human retinal cells were grown in Dulbecco's modified Eagle's medium/Ham's Nutrient Mixture F-12 (DMEM/F12), 10% foetal bovine serum (FBS), 1× Penstrep.

Treatment

Briefly, 2×10$^5$ C2C12 cells were electroporated using the Neon Electroporation system (Pulse voltage: 1650, Pulse width: 10, Pulse number: 3). Both single shmiRs and combinations of two shmiRs described above (2 μg/well) were analyzed. As a control, C2C12 cells were electroporated with the pSilencer plasmid expressing a non-targeting siRNA sequence (Thermo Fisher, USA). The C2C12 cells were incubated at 37° C. in complete DMEM media for 24 hours, after which time 50 ug/mL Hygromycin was added to slow the growth of non-transfected cells, followed by another addition of 100 ug/mL at 48 hours post electroporation. At 72 hours, the cells were harvested and total RNA was extracted for qPCR.

5×10$^6$ ARPE-19 cells were electroporated with the Neon electroporation system using the following conditions: Pulse voltage: 1350, Pulse width: 20, Pulse number: 2. Cells were treated as above for C2C12 cells except that 50 ug/mL of Hygromycin was added at 24 hours with no further additions. ARPE-19 cells were harvested at both 48 and 72 hours for RNA extraction and qPCR analysis.

qPCR Analysis

Reverse Transcriptase qPCR was performed as described for the HEK293 cells of Example 4 with the wtPABPN1 primers and probes used to measure the expression of endogenous PABPN1 in response to inhibition by the shmiRs selected in Example 3. qPCR was performed in triplicate for shmiRs 3, 13, 14, 17 and in duplicate for shmiRs 2, 5, 9, 16 in the C2C12 cells. A single measurement was used at two time points (48 and 72 hours) for the ARPE-19 cells.

Figure 7:
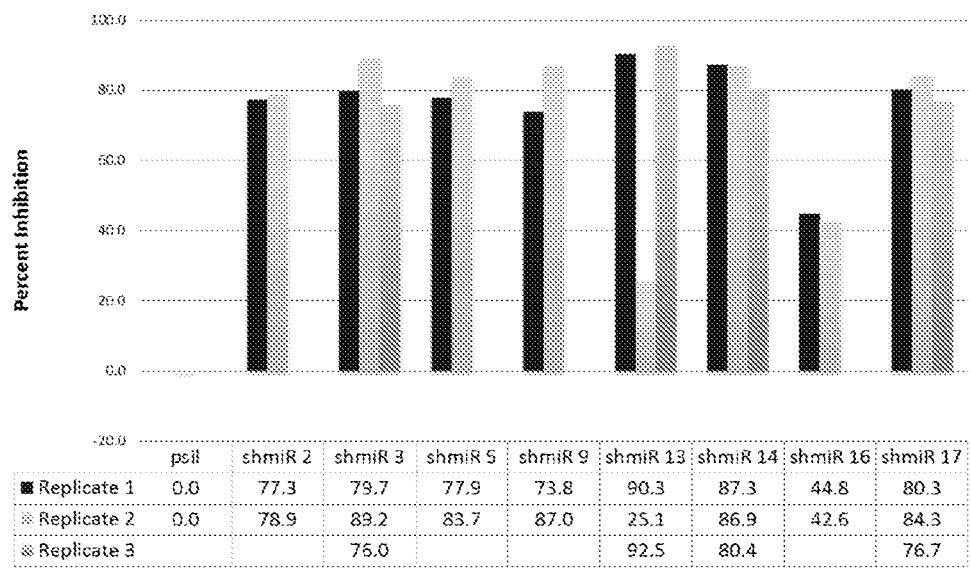
FIG. 7 illustrates the percent inhibition of endogenous PABPN1 expression in C2C12 cells in response to inhibition by shmiR2, shmiR3, shmiR5, shmiR9, shmiR13, shmiR14, shmiR16 or shmiR17, as determined by qPCR analysis. The graph illustrates that all of the individual shmiRs, with the exception of shmiR 16 (percentage inhibition of ~43%), downregulated the expression of PABPN1 in C2C12 cells with a mean percentage inhibition of approximately 80% relative to the pSilencer control.

As shown in FIG. 7, all of the individual shmiRs, with the exception of shmiR 16 (percentage inhibition of ~43%), downregulated the expression of PABPN1 in C2C12 cells with a mean percentage inhibition of approximately 80% relative to the pSilencer control.

The best performing shmiRs, as measured by percent inhibition of PABPN1, were selected for analysis of their ability to inhibit the expression PABPN1 in combination. The combinations of shmiRs 13/17 and shmiRs 3/14 were co-electroporated into the cells and expression of PABPN1 was measured by qPCR as described above for the individual shmiRs.

Figure 8:
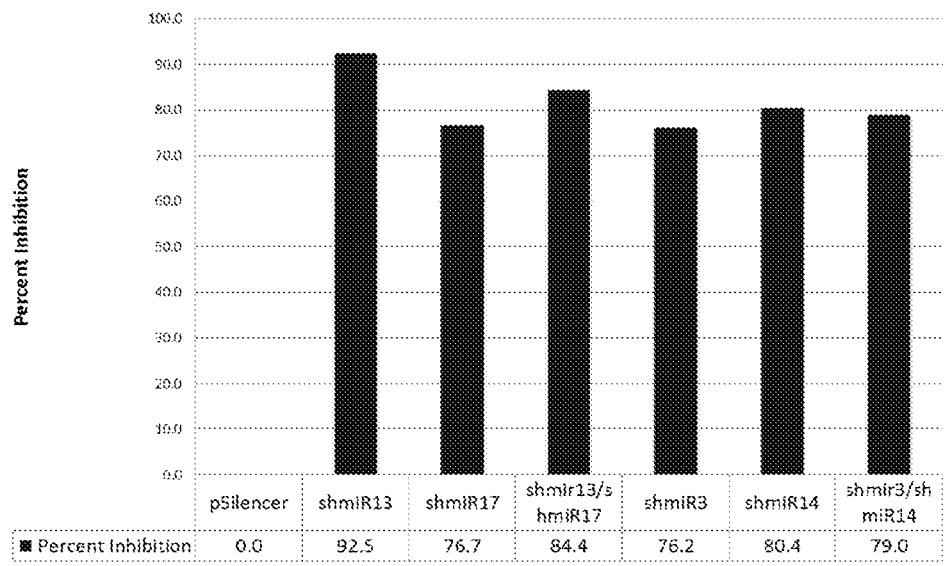
FIG. 8 illustrates the percent inhibition of PABPN1 expression in C2C12 cells by shmiRs shmiR13, shmiR17, shmiR3 and shmiR14 individually; shmiR13 in combination with shmiR17 (shmiR13/17); and shmiR3 in combination with shmiR14 (shmiR3/14), as determined by qPCR analysis. This graph illustrates that shmiR13/17 co-transfection resulted in a percent inhibition of PABPN1 expression of 84.4%, compared to 92.5% and 76.7% for individual shmiR13 and shmiR17 respectively, and shmiR3/14 co-transfection resulted in 79.0% percent inhibition, compared to 76.2% and 80.4% for individual shmiR3 and shmiR14 respectively.

FIG. 8 demonstrates the effect these combinations of shmiRs had on the expression of PABPN1 in C2C12 cells. The shmiR 13/17 co-transfection resulted in a percent inhibition of PABPN1 expression of 84.4% compared to 92.5% and 76.7% for individual shmiRs 13 and 17 respectively. The shmiR 3/14 co-transfection resulted in 79.0% percent inhibition compared to 76.2% and 80.4% for individual shmiRs 3 and 14 respectively.

Figure 9:
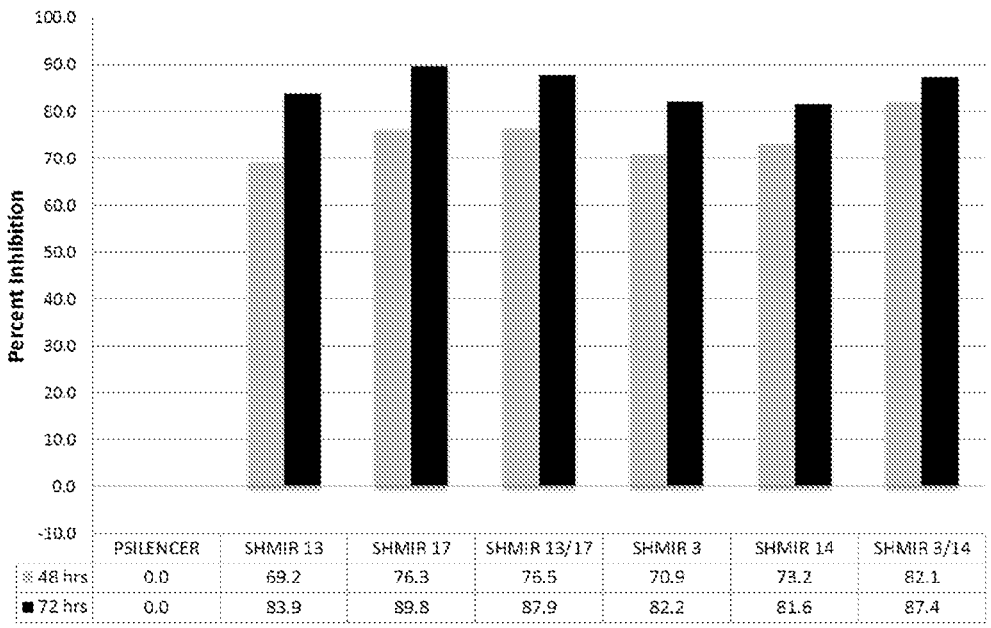
FIG. 9 illustrates the percent inhibition of PABPN1 expression in ARPE-19 cells by shmiR13, shmiR17, shmiR3 and shmiR14 individually; shmiR13 in combination with shmiR17 (shmiR13/17); and shmiR3 in combination with shmiR14 (shmiR3/14), as determined by qPCR analysis. The graph illustrates that the percent inhibition of PABPN1 expression increased 1.14 fold between 48 and 72 hours in ARPE-19 cells.

The same combination of shmiRs as above were tested for their ability to inhibit PABPN1 expression in a human cell line, namely ARPE-19 cells. Cells were treated as described above and the resulting inhibition of PABPN1 expression measured by qPCR at 48 and 72 hours is shown in FIG. 9. After 72 hours, the shmiR 13/17 co-transfection resulted in a percent inhibition of PABPN1 expression of 87.9% compared to 83.9% and 89.8% for individual shmiRs 13 and 17 respectively. The shmiR 3/14 co-transfection resulted in 87.4% percent inhibition compared to 82.2% and 81.6% for individual shmiRs 3 and 14. On average, the percent inhibition of PABPN1 expression increased 1.14 fold between 48 and 72 hours in ARPE-19 cells.

Example 6—Measurement of shmiR Expression by qPCR

In order to determine the total number of shmiRs expressed in C2C12 cells transfected with the best performing shmiRs as described above, a miScript assay was developed.

Production of shmiRs 3, 13, 14, and 17 by the U6 shmiR expression constructs was measured using Qiagen's miScript PCR system (Valencia, Calif.). For each RT-qPCR analysis, 50 ng of total RNA was converted into cDNA using Qiagen's miScript II RT kit. Quantitative PCR of shRNA was then carried out using Qiagen miScript SYBR green PCR kit with custom forward primers set forth below:

```
shmiR3-FWD
                                 (SEQ ID NO: 83)
5'-TTCATCTGCTTCTCTACCTCG-3' shmiR13-FWD
                                 (SEQ ID NO: 84)
5'-AGGGGAATACCATGATGTCGC-3' shmiR14-FWD
                                 (SEQ ID NO: 85)
5'-CTCATATTCATCTGCTTCTCT-3' shmiR17-FWD
                                 (SEQ ID NO: 86)
5'-ATTCATCTGCTTCTCTACCTC-3'
```

Reverse primers were provided in the Qiagen miScript SYBR green PCR kit. The following real-time PCR conditions were used: initial denaturation at 95° C. for 15 min followed by 40 cycles of 94° C. for 15 sec, 55° C. for 30 sec and 70° C. for 30 sec.

Figure 10:
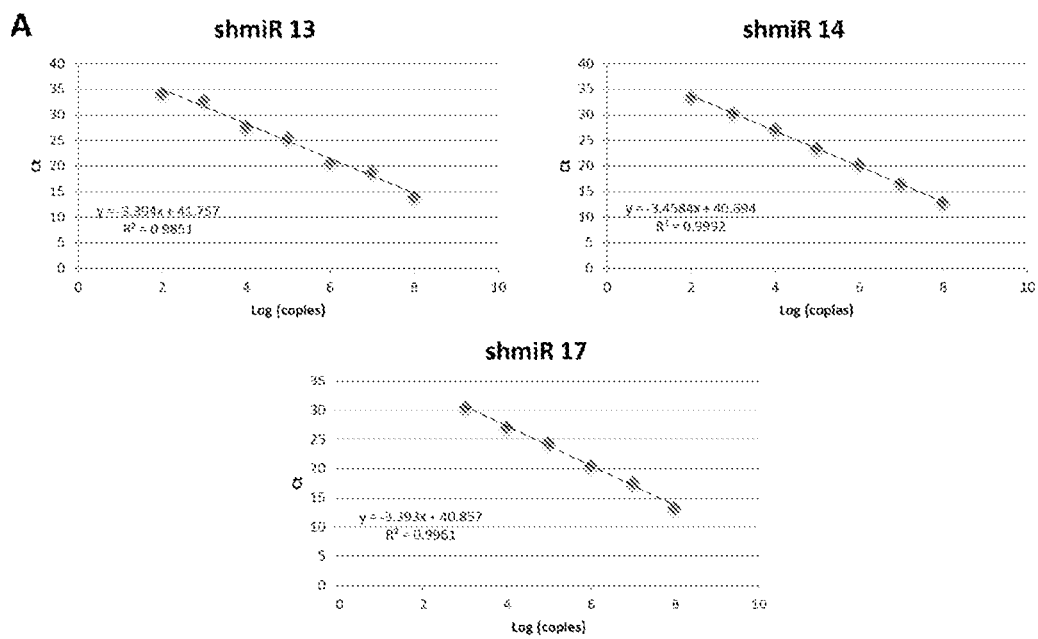
FIG. 10(A) shows standard curves obtained by qPCR determining the total number of shmiRs expressed in C2C12 cells transfected with shmiR13, shmiR14 and shmiR17.
FIG. 10(B) shows a non-linear standard curve obtained by qPCR determining the total number of shmiRs expressed in C2C12 cells transfected with shmiR3.
Figure 10:
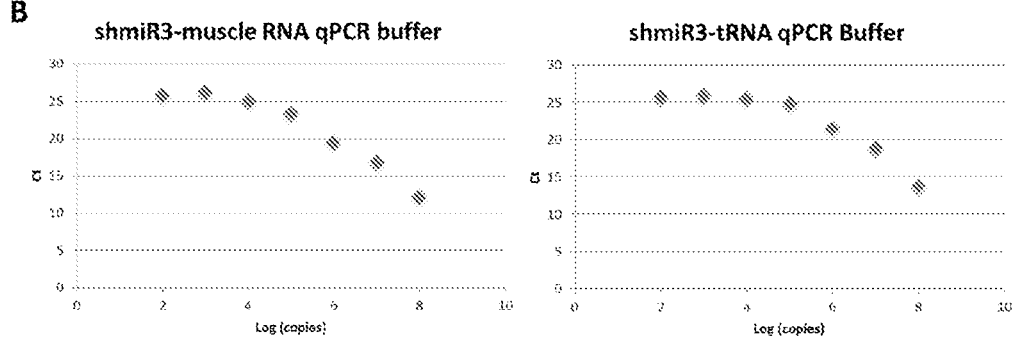

Standard curves for these assays were generated by amplifying known amounts of the selected shmiRs and are presented in FIG. 10. shmiR3 (FIG. 10B) produced a non-linear standard curve and varied according to the qPCR buffer used.

Figure 11:
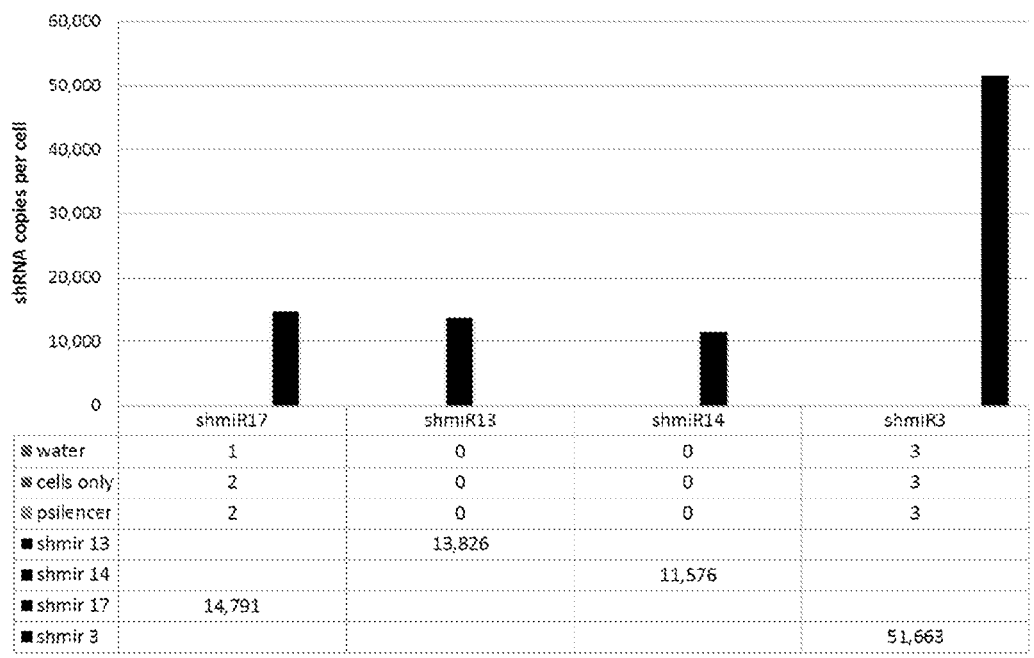
FIG. 11 illustrates the levels of expression of shmiR3, shmiR13, shmiR14 and shmiR17 in C2C12 cells transduced with the shmiR vectors expressing said shmiRs.

RNA copy numbers per cell were calculated based on the estimate of 10 ng total RNA in 333 C2C12 cells. shmiR copies per cell were determined for each of shmiR3, shmiR13, shmiR14 and shmiR17 when expressed individually. As presented in FIG. 11, individual shRNA expression levels in C2C12 cells transduced with the shmiR vectors were estimated to be 51,663, 13,826, 11,576, and 14,791 copies per cell for shmiRs 3, 13, 14, and 17 respectively.

Example 7—Generation of Vectors for Simultaneous Gene Silencing of Endogenous PABPN1 and Replacement with Codon Optimised PABPN1

In order to direct the simultaneous gene silencing of endogenous wild-type PABN1 (wtPABN1) and replacement with codon optimised PABPN1 (coPABN1), single stranded adeno-associated virus type 2 (ssAAV2) plasmids expressing one or more of the selected shmiRs in combination with the optPABPN1 sequence are created. Two alternative constructs are presented in FIGS. 12A and 12B.

The first construct, version 2, (FIG. 12A) is generated by subcloning two shmiRs targeting wtPABPN1 into the 3' untranslated region of the optPABPN1 transcript in the pAAV2 vector backbone. Expression of both optPABPN1 and the two shmiRs in a single transcript is driven by the Muscle specific promoter Spc512. The second construct, version 1, (FIG. 12B) is generated by subcloning two shmiRs targeting wtPABPN1 into the sequence upstream of the optPABPN1 transcript. In this construct, two transcripts are expressed, the first encoding the two shmiRs under control of the CK8 promoter and the second encoding optPABPN1 under the Spc512 promoter.

Recombinant pseudotyped AAV vector stocks are generated. Briefly, HEK293T cells are cultured in cell factories in Dulbecco's modified Eagle's medium, supplemented with 10% FBS, and incubated at 37° C. and 5% $CO_2$. The pAAV-shmiR viral plasmids as described in this example and a pAAVhelper and pAAVrepcap8 plasmid or pAAVhelper and pAAV repcap9 plasmid are complexed with Calcium Phosphate according to the manufacturer's instructions. Triple-transfections are then performed with each of the pAAV-shmiR plasmids in combination with, pAAVhelper and pAAVrepcap8 or pAAVrepcap9 in the HEK293T cells. The HEK293T cells are cultured for a period of 72 hours at 37° C. and 5% $CO_2$, after which time the cells are lysed and ssAAV shmiR-expressing particles for each of the viral plasmids are purified by iodixanol (Sigma-Aldrich) step-gradient ultracentrifugation followed by cesium chloride ultracentrifugation. The number of vector genomes was quantified by quantitative polymerase chain reaction (Q-PCR).

Example 8—In Vivo Efficacy Studies in a Murine Model of OPMD

Animals

Pre-clinical efficacy studies were performed in the most common murine model of OPMD, the A17 mouse model. This mouse model was generated in the FvB background by over expressing a bovine expanded (17 alanine residues) PABPN1. Expression of this mutant PABPN1 in skeletal muscle was placed under control of the human alpha actin muscle-specific promoter (HSA1). Both endogenous murine PABPN1 alleles are functional and express normal murine PABPN1. Therefore, the mouse phenotype was due to the overexpression of the mutant PABPN1 over the normal protein. Most importantly, A17 mice display many of the clinical signs of OPMD including the presence of intranuclear inclusions (INIs), fibrosis, and loss of muscle strength. In vivo mouse efficacy studies focused on dosing and analyses of the Tibialis anterior (TA) muscles, amongst the largest muscles that can be easily manipulated and/or isolated from the mice, making it easier to observe phenotypic improvements.

Treatment

Adeno Associated Virus Serotype 9 (AAV9) capsid was selected for administration of the recombinant expression constructs via local intramuscular injection. In addition to AAV9, a number of different serotypes of AAV capsids, including AAV8, AAVRh74, were tested. Muscle transduction was assessed using a recombinant AAV9 construct that expressed the fluorescent protein GFP under the control of the Spc512 synthetic muscle promoter (AAV9-eGFP). Mice from both sexes were injected in each TA muscle with 50 µl of the single stranded vector at a dose of 2e11 total vector genomes. After twenty days, the mice were sacrificed and the injected limbs were examined by in vivo imaging.

Results

Figure 13:
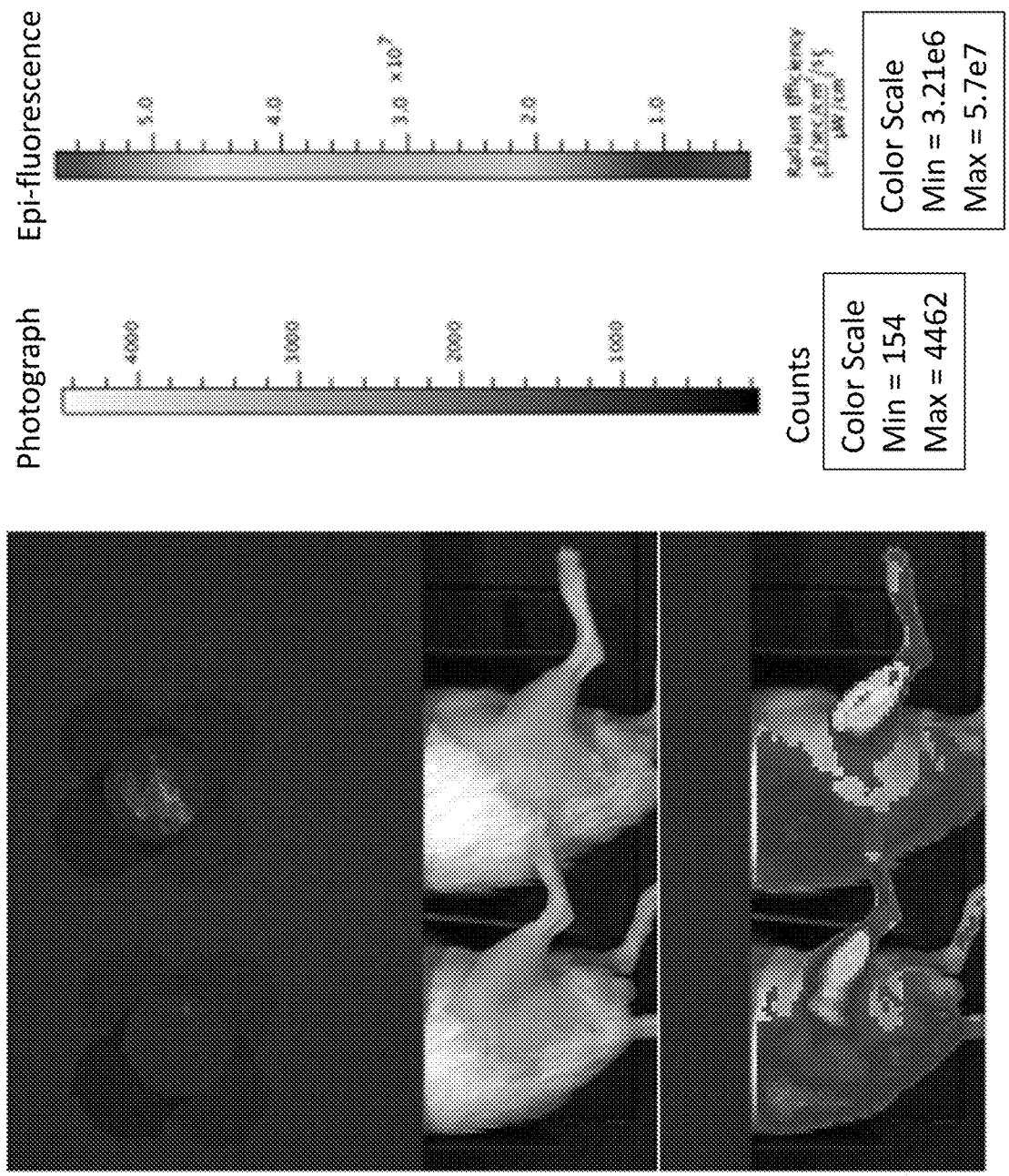
FIG. 13 shows in vivo fluorescence in mouse limb following injection with AAV9-eGFP.

As shown in FIG. 13, direct injection of the TA muscle with the AAV9-eGFP construct resulted in a significant amount of local fluorescence being detected in the limb, suggesting that both the vector is effective at transducing muscle cells and results in transgene expression following a direct injection.

Example 9—Generation of a Single "Silence and Replace Construct" for Simultaneous Gene Silencing of Endogenous PABPN1 and Replacement with Codon Optimised PABPN1

A single stranded adeno-associated virus type 2 (ssAAV2) plasmid expressing shmiR17 and shmiR13 (e.g., as described in Tables 3 and 4) in combination with the optPABPN1 sequence was created.

Figure 14:
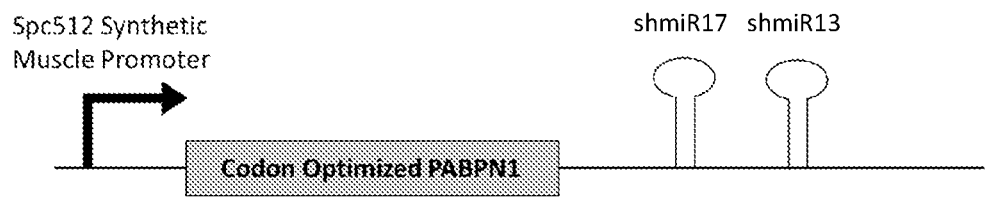
FIG. 14 is a schematic illustrating the SR-construct designed for simultaneous gene silencing of endogenous PABPN1 and replacement with codon optimised PABPN1 generated by subcloning two shmiRs targeting wtPABPN1 (shmiR17 and shmiR13) into the 3' untranslated region of the codon optimized PABPN1 transcript in the pAAV2 vector backbone.

The silence and replace construct (hereinafter "SR-construct") was generated by subcloning DNA sequences encoding shmiR17 and shmiR13 (as described in Table 4) into the 3' untranslated region of the optPABPN1 transcript in the pAAV2 vector backbone (pAAV-shmiR viral plasmid). Expression of both optPABPN1 and the two shmiRs in a single transcript is driven by the muscle specific promoter Spc512. A schematic of the SR-construct is provided in FIG. 14.

Recombinant pseudotyped AAV vector stocks were then generated. Briefly, HEK293T cells were cultured in cell factories in Dulbecco's modified Eagle's medium, supplemented with 10% FBS, and incubated at 37° C. and 5% $CO_2$. The pAAV-shmiR viral plasmid and a pAAVhelper and pAAVrepcap8 plasmid or pAAVhelper and pAAV repcap9 or pAAV helper and pAAVRH74 plasmid were complexed with Calcium Phosphate according to the manufacturer's instructions. Triple-transfections were then performed with the pAAV-shmiR plasmid in combination with the pAAVhelper and one of the following capsids; pAAVrepcap8, pAAVrepcap9 or pAAVRH74, in the HEK293T cells. The HEK293T cells were then cultured for a period of 72 hours at 37° C. and 5% $CO_2$, after which time the cells were lysed and ssAAV shmiR-expressing particles were purified by iodixanol (Sigma-Aldrich) step-gradient ultracentrifugation followed by cesium chloride ultracentrifugation. The number of vector genomes was quantified by quantitative polymerase chain reaction (Q-PCR).

Example 10—In Vivo Efficacy Studies with a Single Vector "Silence and Replace" Approach Treatment In order to test the in vivo efficacy of the SR-construct described in Example 9 in a relevant disease model of OPMD, the SR-construct was administered individually, at a high and low dose, via intramuscular injection into the TA muscle of 10-12 week old A17 mice. The low dose was set at $1 \times 10^{10}$ vector genomes per muscle. The high dose was set at $6 \times 10^{10}$ vector genomes per muscle. Saline injected age-matched A17 mice served as the untreated group whilst FVB wildtype mice were also included as healthy comparators. In addition to examining the impact of different doses of the SR-construct on disease, separate cohorts of mice were sacrificed at either 14 or 20 weeks post treatment to evaluate efficacy related to different time points. At sacrifice, the TA muscles were harvested and RNA and proteins extracted.

qPCR Analysis

Figure 15:
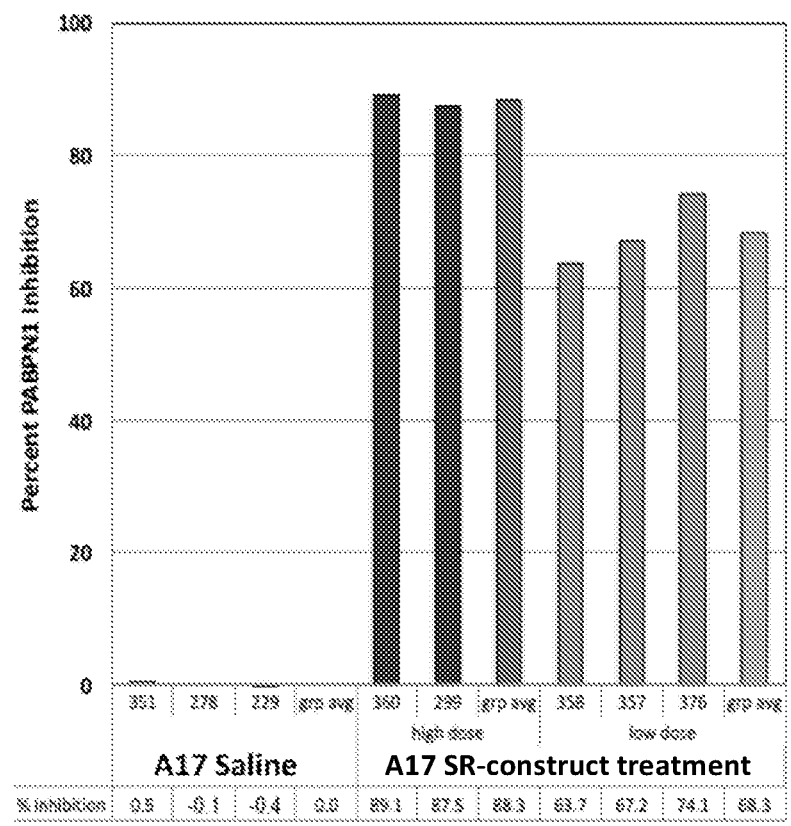
FIG. 15 illustrates percent inhibition of PABPN1 in A17 mice treated with the silence and replace construct (hereinafter the "SR-construct"), and shows that robust inhibition of PABPN1 is achieved at both high and low doses.

To verify knockdown of PABPN1 levels, RNA isolated from the TA muscles was evaluated by QPCR analysis. The QPCR primers used were unable to discriminate between the wildtype PABPN1 and the mutant PABPN1 transcripts, but did not recognize or amplify sequences corresponding to the codon optimized PABPN1 species. Robust knockdown was observed with the SR-construct at both the high and low doses resulting in the reduction of PABPN1 transcripts at 88.3% and 68.3% respectively (FIG. 15). Additional analyses from these tissues demonstrated the presence of the shmiR transgenes in ratios consistent with the different levels of administered vectors.

Similarly, QPCR analyses using a set of primers that can selectively amplify the codon optimized PABPN1 sequences and discriminate against the normal wildtype and mutant PABPN1 sequences were used to verify expression of the codon optimized PABPN1 moiety.

Figure 16:
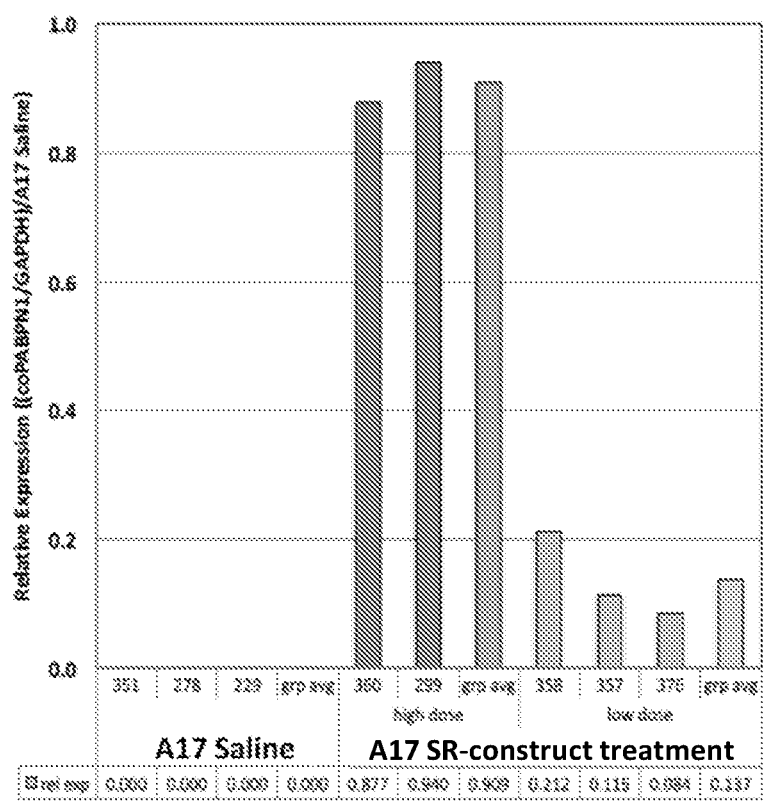
FIG. 16 illustrates the level of expression of codon-optimised PABPN1 relative to wildtype PABPN1 (including mutant form) in A17 mice treated with the SR-construct at high and low doses.

These QPCR analyses demonstrated that animals administered the SR-construct expressed codon optimized PABPN1 levels at 90.9% and 13.7%, on average, of normal PABPN1 levels in FvB mice in the high and low dose respectively (FIG. 16).

Combined, the analyses confirm that a single transcript can produce functional shmiRs that have the capability to knock down PABPN1 levels, including the mutant form, in the A17 mouse model. Likewise, these vectors simultaneously produce adequate levels of codon optimized PABPN1 as a replacement in order to restore PABPN1 function.

Intranuclear Inclusions (INIs)

Figure 17:
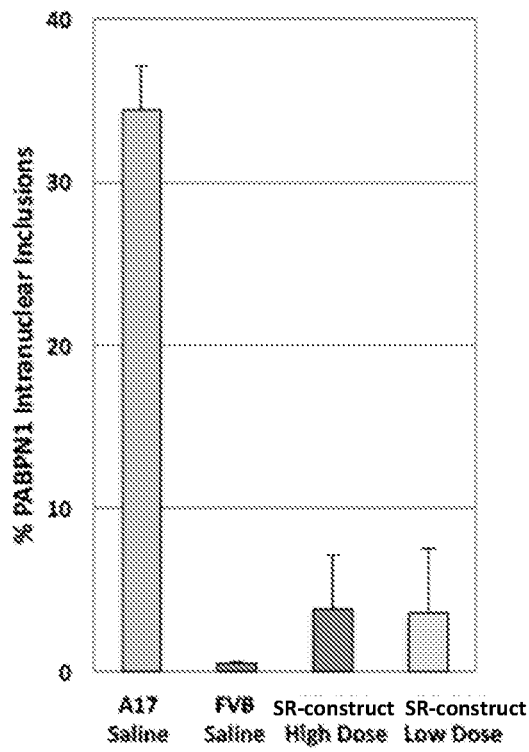
FIG. 17 shows immunofluorescence histochemistry for PABPN1 and laminin detection in sections of Tibialis anterior (TA) muscles from (i) A17 mice treated with saline, (ii) FvB mice treated with saline, (iii) A17 mice treated with the SR-construct at high and low doses. The number of PABPN1 positive intranuclear inclusions (INIs) is significantly reduced in muscles from mice treated with the SR-construct at both high and low doses.
Figure 18:
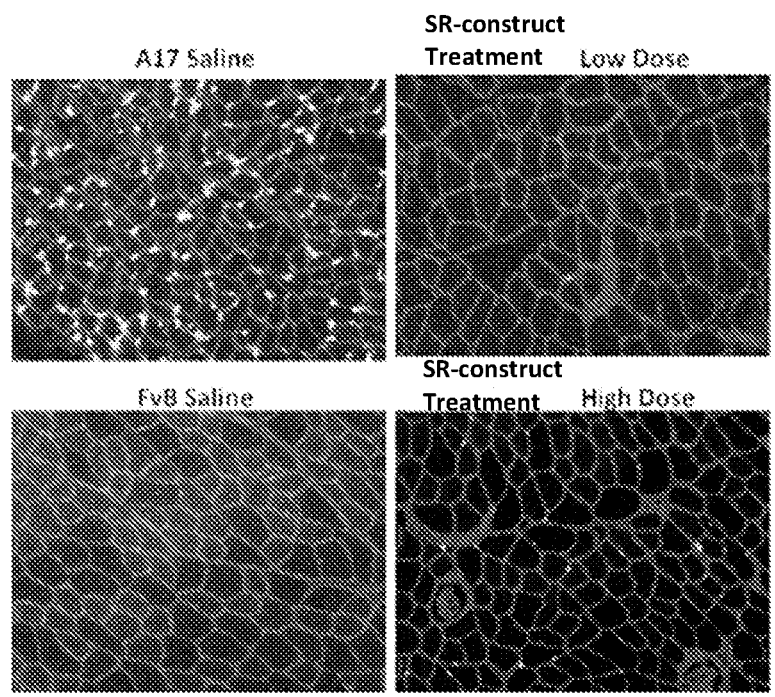
FIG. 18 illustrates the level of nuclei containing INIs (expressed as a percentage) in sections of Tibialis anterior (TA) muscles from (i) A17 mice treated with saline, (ii) FvB mice treated with saline, (iii) A17 mice treated with the SR-construct at high and low doses. This graph illustrates that treatment with the SR-construct at both high and low doses reduces the amount of INIs to about 10% compared to saline injected A17 muscles.

The impact of the SR-construct on the persistence of intranuclear inclusions (INIs) was tested in the week 14 animals. As is evident from FIG. 17, nearly 35% of all TA muscle cells in the A17 mice showed the green punctate staining representative of INIs. Red Laminin (an abundant protein in the extracellular matrix of muscle cells) and Blue DAPI counterstains were used to define cell shape and nuclei respectively (FIG. 18). Through a range of serial sections, treatment with both high and low doses of the SR-construct demonstrated a significant reduction of INIs.

Muscle Weight

The impact of the SR-construct on the restoration of muscle weight was also tested on week 20 animals.

Figure 19:
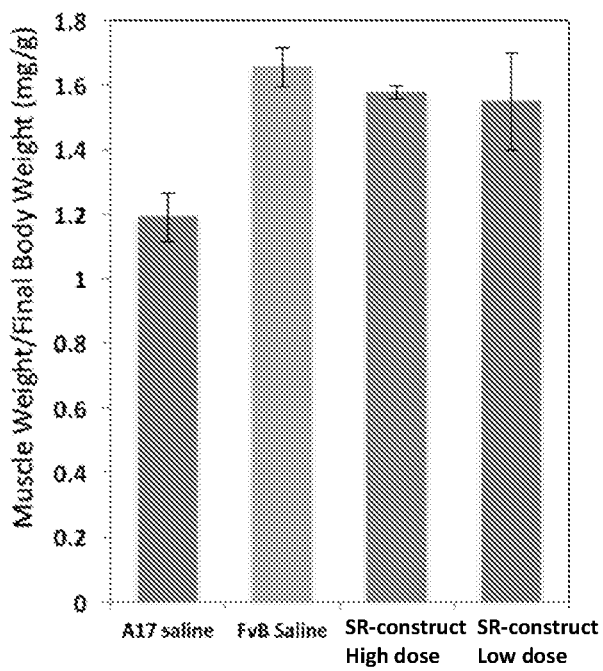
FIG. 19 shows weight of Tibialis anterior (TA) muscles excised from (i) A17 mice treated with saline, (ii) FvB mice treated with saline, (iii) A17 mice treated with the SR-construct at high and low doses. This graph shows that treatment with the SR-construct at both high and low doses restored muscle weight to near wildtype levels of the FvB animals. All muscle measurement were taken on the day of sacrifice, at 14 or 20 weeks post-injection.

The TA muscle cells from A17 mice weigh roughly 25% less than similar muscles from their FvB wildtype counterparts. At both doses tested, the SR-construct showed a significant restoration of muscle weight to near wild type levels of the FVB animals (FIG. 19).

Muscle Strength

Finally, the impact of SR-construct on restoration of muscle strength on week 20 animals was assessed by maximal force measurements.

Figure 20:
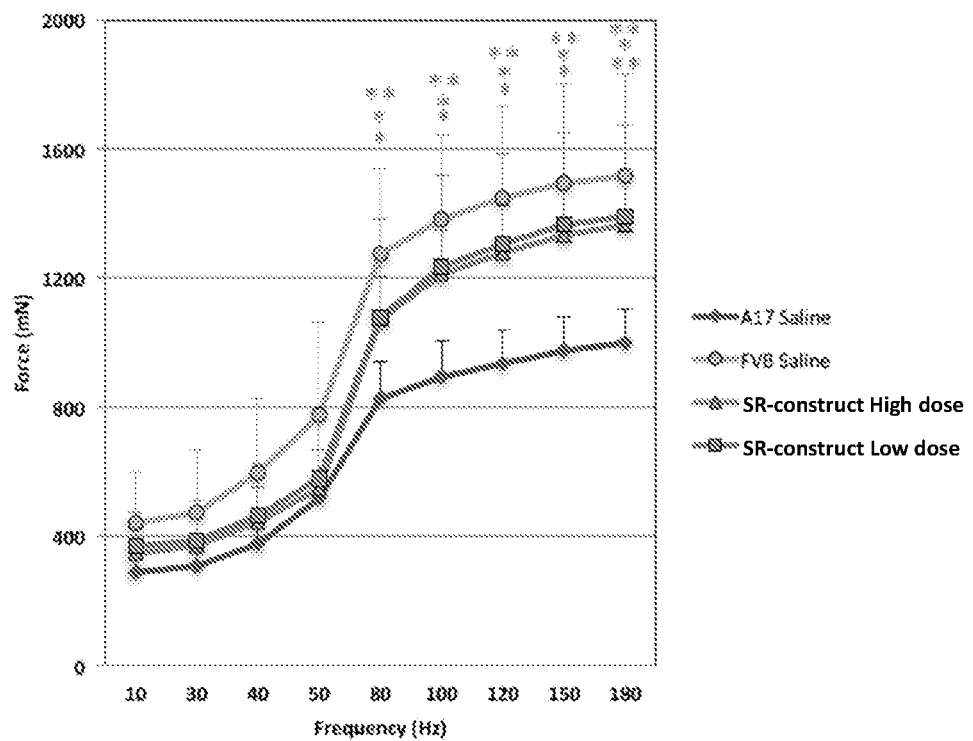
FIG. 20 shows isometric maximal force of Tibialis anterior (TA) muscles excised from (i) A17 mice treated with saline, (ii) FvB mice treated with saline, (iii) A17 mice treated with the SR-construct at high and low doses. This graph shows that treatment with the SR-construct at both high and low doses restored roughly 66% of the reduced strength difference noted in the A17 mice relative to FvB wildtype animals. All muscle measurement were taken on the day of sacrifice, at 14 or 20 weeks post-injection. Statistics shown as unpaired t-test relative to A17 Saline mice. $*p<0.05$, $**p<0.01$.

Using the 150 mHz frequency as a calibration point, A17 mice had roughly 30% less maximal force than their wildtype FvB counterparts at 1050 nm vs 1500 nm respectively. Treatment with the SR-construct led to modest increases in maximal force, restoring roughly 66% of the reduced strength difference noted in the A17 mouse versus FVB wildtype animals (FIG. 20). Statistics in FIG. 20 are shown as unpaired t-test relative to A17 Saline mice (*$p<0.05$, **$p<0.01$).

Collectively, the data presented herein from this in vivo study demonstrate that treatment with the SR-construct has an impact on physiological hallmark of the OPMD disease in the A17 model system.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

We claim:

1. A nucleic acid comprising a DNA sequence which encodes a short hairpin micro-RNA (shmiR) targeting a transcript of PABPN1, said shmiR comprising:
   an effector sequence of at least 17 nucleotides in length;
   an effector complement sequence;
   a stemloop sequence; and
   a primary micro RNA (pri-miRNA) backbone;
   wherein the effector sequence is complementary to a region of corresponding length in an RNA transcript set forth in SEQ ID NO: 13 or complementary to a region of corresponding length in an RNA transcript set forth in SEQ ID NO: 13 with the exception of 1, 2, 3 or 4 base mismatches relative to the RNA transcript set forth in SEQ ID NO: 13.

2. The nucleic acid according to claim 1, wherein the shmiR comprises an effector sequence set forth in SEQ ID NO: 39 and an effector complement sequence set forth in SEQ ID NO: 38.

3. The nucleic acid according to claim 1, wherein the shmiR comprises, in a 5' to 3' direction:
   (a) a 5' flanking sequence of the pri-miRNA backbone;
   the effector complement sequence;
   the stemloop sequence;
   the effector sequence; and
   a 3' flanking sequence of the pri-miRNA backbone; or
   (b) a 5' flanking sequence of the pri-miRNA backbone;
   the effector sequence;
   the stemloop sequence;
   the effector complement sequence; and
   a 3' flanking sequence of the pri-miRNA backbone.

4. The nucleic acid according to claim 1, wherein:
   (a) the stemloop sequence is the sequence set forth in SEQ ID NO: 40;
   (b) the pri-miRNA backbone is a pri-miR-30a backbone; and/or
   (c) the 5' flanking sequence of the pri-miRNA backbone is set forth in SEQ ID NO: 41 and the 3' flanking sequence of the pri-miRNA backbone is set forth in SEQ ID NO: 42.

5. The nucleic acid according to claim 1, wherein:
   (a) the shmiR comprises a sequence set forth in SEQ ID NO: 55; and/or
   (b) the DNA sequence which encodes the shmiR is set forth in SEQ ID NO: 68.

6. A plurality of nucleic acids, comprising:
   (a) at least one nucleic acid according to claim 1; and
   (b) at least one further nucleic acid comprising a DNA sequence which encodes a shmiR comprising:
   an effector sequence of at least 17 nucleotides in length;
   an effector complement sequence;
   a stemloop sequence; and
   a pri-miRNA backbone;
   wherein the effector sequence is substantially complementary to a region of corresponding length in an RNA transcript set forth in any one of SEQ ID NOs: 1-12.

7. An expression vector comprising:
   (a) a nucleic acid according to claim 1;
   (b) a ddRNAi construct comprising the nucleic acid of (a); or
   (c) a DNA construct comprising a ddRNAi construct of (b) and a PABPN1 construct comprising a DNA sequence encoding a functional PABPN1 protein having a mRNA transcript which is not targeted by the shmiR(s) encoded by the ddRNAi construct.

8. The expression vector of claim 7, wherein the expression vector is a viral vector selected from the group consisting of an adeno-associated viral (AAV) vector, a retroviral vector, an adenoviral (AdV) vector and a lentiviral (LV) vector.

9. A composition comprising:
(a) a nucleic acid according to claim 1;
(b) a ddRNAi construct comprising the nucleic acid of (a);
(c) a DNA construct comprising the ddRNAi construct of (b) and a PABPN1 construct comprising a DNA sequence encoding a functional PABPN1 protein having a mRNA transcript which is not targeted by the shmiR(s) encoded by the ddRNAi construct;
(d) an expression vector comprising (a), (b) or (c); or (e) a plurality of expression vectors comprising at least one expression vector comprising the ddRNAi construct of (b) and at least one expression vector comprising a PABPN1 construct comprising a DNA sequence encoding a functional PABPN1 protein having a mRNA transcript which is not targeted by the shmiR(s) encoded by the ddRNAi construct;
optionally wherein the composition further comprises one or more pharmaceutically acceptable carriers.

10. A method of inhibiting expression of a PABPN1 protein which is causative of oculopharyngeal muscular dystrophy (OPMD) in a subject, said method comprising administering to the subject:
(a) a nucleic acid according to claim 1;
(b) a ddRNAi construct comprising the nucleic acid of (a);
(c) a DNA construct comprising a ddRNAi construct of (b) and a PABPN1 construct comprising a DNA sequence encoding a functional PABPN1 protein having a mRNA transcript which is not targeted by the shmiR(s) encoded by the ddRNAi construct;
(d) an expression vector comprising (a), (b) or (c);
(e) a plurality of expression vectors comprising at least one expression vector comprising the ddRNAi construct of (b) and at least one expression vector comprising a PABPN1 construct comprising a DNA sequence encoding a functional PABPN1 protein having a mRNA transcript which is not targeted by the shmiR(s) encoded by the ddRNAi construct; or
a composition comprising any one of (a)-(e).

11. A method of treating oculopharyngeal muscular dystrophy (OPMD) in a subject suffering therefrom, said method comprising administering to the subject:
(a) a nucleic acid according to claim 1;
(b) a ddRNAi construct comprising the nucleic acid of (a);
(c) a DNA construct comprising a ddRNAi construct of (b) and a PABPN1 construct comprising a DNA sequence encoding a functional PABPN1 protein having a mRNA transcript which is not targeted by the shmiR(s) encoded by the ddRNAi construct;
(d) an expression vector comprising (a), (b) or (c);
(e) a plurality of expression vectors comprising at least one expression vector comprising the ddRNAi construct of (b) and at least one expression vector comprising a PABPN1 construct comprising a DNA sequence encoding a functional PABPN1 protein having a mRNA transcript which is not targeted by the shmiR(s) encoded by the ddRNAi construct; or
(f) a composition comprising any one of (a)-(e).

12. A DNA-directed RNA interference (ddRNAi) construct comprising a nucleic acid according to claim 1.

13. The ddRNAi construct according to claim 12, comprising a further nucleic acid comprising a DNA sequence which encodes a shmiR comprising:
an effector sequence of at least 17 nucleotides in length;
an effector complement sequence;
a stemloop sequence; and
a pri-miRNA backbone;
wherein the effector sequence is substantially complementary to a region of corresponding length in an RNA transcript set forth in any one of SEQ ID NOs: 1-12.

14. The ddRNAi construct according to claim 13, wherein:
(a) the further nucleic acid encodes a shmiR comprising an effector sequence which is substantially complementary to a region of corresponding length in an RNA transcript set forth in one of SEQ ID NOs: 1, 2, 4, 7, 9 and 10;
(b) the ddRNAi construct comprises a nucleic acid comprising or consisting of a DNA sequence encoding a shmiR comprising an effector sequence set forth in SEQ ID NO: 39 and an effector complement sequence set forth in SEQ ID NO: 38 (shmiR17) and a further nucleic acid selected from the group consisting of:
a nucleic acid comprising or consisting of a DNA sequence encoding a shmiR comprising an effector sequence set forth in SEQ ID NO: 15 and an effector complement sequence set forth in SEQ ID NO: 14 (shmiR2);
a nucleic acid comprising or consisting of a DNA sequence encoding a shmiR comprising an effector sequence set forth in SEQ ID NO: 17 and an effector complement sequence set forth in SEQ ID NO: 16 (shmiR3);
a nucleic acid comprising or consisting of a DNA sequence encoding a shmiR comprising an effector sequence set forth in SEQ ID NO: 21 and an effector complement sequence set forth in SEQ ID NO: 20 (shmiR5);
a nucleic acid comprising or consisting of a DNA sequence encoding a shmiR comprising an effector sequence set forth in SEQ ID NO: 27 and an effector complement sequence set forth in SEQ ID NO: 26 (shmiR9);
a nucleic acid comprising or consisting of a DNA sequence encoding a shmiR comprising an effector sequence set forth in SEQ ID NO: 31 and an effector complement sequence set forth in SEQ ID NO: 30 (shmiR13); and
a nucleic acid comprising or consisting of a DNA sequence encoding a shmiR comprising an effector sequence set forth in SEQ ID NO: 33 and an effector complement sequence set forth in SEQ ID NO: 32 (shmiR14);
and/or
(c) the ddRNAi construct comprises a nucleic acid comprising or consisting of a DNA sequence set forth in SEQ ID NO: 68 (shmiR17) and a further nucleic acid selected from the group consisting of:
a nucleic acid comprising or consisting of a DNA sequence set forth in SEQ ID NO: 56 (shmiR2);
a nucleic acid comprising or consisting of a DNA sequence set forth in SEQ ID NO: 57 (shmiR3);
a nucleic acid comprising or consisting of a DNA sequence set forth in SEQ ID NO: 59 (shmiR5);
a nucleic acid comprising or consisting of a DNA sequence set forth in SEQ ID NO: 62 (shmiR9);
a nucleic acid comprising or consisting of a DNA sequence set forth in SEQ ID NO: 64 (shmiR13); and
a nucleic acid comprising or consisting of a DNA sequence set forth in SEQ ID NO: 65 (shmiR14).

15. The ddRNAi construct according to claim 13, said ddRNAi construct comprising:
(a) a nucleic acid comprising or consisting of a DNA sequence encoding a shmiR comprising an effector sequence set forth in SEQ ID NO: 31 and an effector complement sequence set forth in SEQ ID NO: 30 (shmiR13); and (b) a nucleic acid comprising or consisting of a DNA sequence encoding a shmiR comprising an effector sequence set forth in SEQ ID NO: 39 and an effector complement sequence set forth in SEQ ID NO: 38 (shmiR17).

16. The ddRNAi construct according to claim 15, said ddRNAi construct comprising:
    (a) a nucleic acid comprising or consisting of the DNA sequence set forth in SEQ ID NO: 64 (shmiR13); and
    (b) a nucleic acid comprising or consisting of the DNA sequence set forth in SEQ ID NO: 68 (shmiR17).

17. The ddRNAi construct according to claim 12, comprising a RNA pol III promoter upstream of the or each nucleic acid encoding a shmiR, optionally wherein the or each RNA pol III promoter is a U6 promoter selected from U6-9 promoter, a U6-1 promoter and U6-8 promoter, or a H1 promoter.

18. A DNA construct comprising:
    (a) a ddRNAi construct according to claim 12; and
    (b) a PABPN1 construct comprising a DNA sequence encoding a functional PABPN1 protein having a mRNA transcript which is not targeted by the shmiR(s) encoded by the ddRNAi construct.

19. The DNA construct according to claim 18, wherein the DNA sequence encoding the functional PABPN1 protein is codon optimised such that its mRNA transcript is not targeted by the shmiRs of the ddRNAi construct, optionally wherein the codon optimised DNA sequence encoding the functional PABPN1 protein is set forth in SEQ ID NO: 73.

20. The DNA construct according to claim 18, wherein the DNA sequence encoding the functional PABPN1 protein is operably-linked to a promoter comprised within the PABPN1 construct and positioned upstream of the DNA sequence encoding the functional PABPN1 protein, optionally wherein the promoter comprised within the PABPN1 construct is a muscle-specific promoter.

21. The DNA construct according to claim 18, wherein:
    (a) the DNA construct comprises, in a 5' to 3' direction, the ddRNAi construct and the PABPN1 construct; or
    (b) the DNA construct comprises, in a 5' to 3' direction, the PABPN1 construct and the ddRNAi construct.

22. A plurality of expression vectors comprising:
    (a) an expression vector comprising the ddRNAi construct of claim 12; and
    (b) an expression vector comprising a PABPN1 construct comprising a DNA sequence encoding a functional PABPN1 protein having a mRNA transcript which is not targeted by the shmiR(s) encoded by the ddRNAi construct.

23. The plurality of expression vectors according to claim 22, wherein the DNA sequence encoding the functional PABPN1 protein is codon optimised such that its mRNA transcript is not targeted by the shmiRs of the ddRNAi construct, optionally wherein the codon optimised DNA sequence encoding the functional PABPN1 protein is set forth in SEQ ID NO: 73.

24. The plurality of expression vectors according to claim 22, wherein the DNA sequence encoding the functional PABPN1 protein is operably-linked to a promoter comprised within the PABPN1 construct and positioned upstream of the DNA sequence encoding the functional PABPN1 protein, optionally wherein the promoter comprised within the PABPN1 construct is a muscle-specific promoter.

25. An adeno-associated virus (AAV) comprising a DNA construct comprising:
    (a) a muscle-specific promoter;
    (b) a ddRNAi construct comprising: a nucleic acid comprising a DNA sequence encoding a shmiR comprising an effector sequence set forth in SEQ ID NO: 39 and an effector complement sequence set forth in SEQ ID NO: 38; and a nucleic acid comprising a DNA sequence encoding a shmiR comprising an effector sequence set forth in SEQ ID NO: 31 and an effector complement sequence set forth in SEQ ID NO: 30; and
    (c) a PABPN1 construct comprising a DNA sequence encoding a functional PABPN1 protein having a mRNA transcript which is not targeted by the shmiRs encoded by the ddRNAi construct.

26. The AAV of claim 25, wherein the DNA construct comprises, in a 5' to 3' direction, the muscle-specific promoter, the PABPN1 construct, and the ddRNAi construct.

27. The AAV of claim 26, wherein:
    the muscle-specific promoter is a Spc512 promoter;
    the ddRNAi construct comprises a nucleic acid comprising or consisting of the DNA sequence set forth in SEQ ID NO: 68 and a nucleic acid comprising or consisting of the DNA sequence set forth in SEQ ID NO: 64; and
    wherein the DNA sequence encoding the functional PABPN1 protein is codon optimised and its mRNA transcript is not targeted by the shmiRs of the ddRNAi construct, optionally wherein the codon optimised DNA sequence encoding the functional PABPN1 protein is set forth in SEQ ID NO: 73.

* * * * *